US012790374B2

(12) United States Patent
Bettoun

(10) Patent No.: US 12,790,374 B2

(45) Date of Patent: Nov. 10, 2026

(54) METHODS FOR TREATING MYELIN ASSOCIATED DISEASES AND MITOCHONDRIA ASSOCIATED DISEASES

(71) Applicant: Larimar Therapeutics, Inc., Bala Cynwyd, PA (US)

(72) Inventor: Joan David Bettoun, Elkins Park, PA (US)

(73) Assignee: Larimar Therapeutics, Inc., Bala Cynwyd, PA (US)

( * ) Notice: Subject to any disclaimer, the term of this patent is extended or adjusted under 35 U.S.C. 154(b) by 0 days.

(21) Appl. No.: 18/433,336

(22) Filed: Feb. 5, 2024

(65) Prior Publication Data

US 2024/0343766 A1 Oct. 17, 2024

Related U.S. Application Data

(63) Continuation of application No. 17/246,549, filed on Apr. 30, 2021, now Pat. No. 11,976,100.

(60) Provisional application No. 63/018,451, filed on Apr. 30, 2020.

(51) Int. Cl.
*C07K 14/47* (2006.01)
*A61K 38/00* (2006.01)

(52) U.S. Cl.
CPC .......... *C07K 14/4702* (2013.01); *A61K 38/00* (2013.01); *C07K 2319/095* (2013.01); *C07K 2319/10* (2013.01); *C07K 2319/50* (2013.01)

(58) Field of Classification Search
None
See application file for complete search history.

(56) References Cited

U.S. PATENT DOCUMENTS

| | | | | |
|---|---|---|---|---|
| 8,283,444 | B2 | 10/2012 | Payne | |
| 9,260,495 | B2 | 2/2016 | Keefe et al. | |
| 11,459,363 | B2 | 10/2022 | Payne | |
| 11,891,420 | B2 * | 2/2024 | Bettoun | A61P 25/28 |
| 11,976,100 | B2 * | 5/2024 | Bettoun | A61K 38/1709 |
| 11,988,675 | B2 | 5/2024 | Bettoun | |
| 2004/0101874 | A1 | 5/2004 | Ghosh et al. | |
| 2005/0169904 | A1 | 8/2005 | Payne | |
| 2011/0190224 | A1 | 8/2011 | Payne | |
| 2012/0196328 | A1 | 8/2012 | Liu et al. | |
| 2014/0135275 | A1 | 5/2014 | Keefe et al. | |
| 2014/0187606 | A1 | 7/2014 | Collard et al. | |
| 2014/0308262 | A1 | 10/2014 | Lorberboum-Galski | |
| 2015/0132769 | A1 | 5/2015 | Payne et al. | |
| 2015/0353616 | A1 | 12/2015 | Wraith et al. | |
| 2016/0060605 | A1 | 3/2016 | Testi | |
| 2016/0178610 | A1 | 6/2016 | Buehler et al. | |
| 2017/0320968 | A1 | 11/2017 | Tremblay et al. | |
| 2017/0327847 | A1 | 11/2017 | Ghadessy et al. | |
| 2018/0333386 | A1 | 11/2018 | Cortopassi et al. | |
| 2019/0002876 | A1 | 1/2019 | Corey et al. | |
| 2019/0076429 | A1 | 3/2019 | Rufini et al. | |
| 2020/0377951 | A1 | 12/2020 | Bettoun | |
| 2022/0193190 | A1 | 6/2022 | Boyle et al. | |
| 2022/0276258 | A1 | 9/2022 | Bettoun et al. | |
| 2022/0378869 | A1 | 12/2022 | Bettoun | |
| 2023/0242600 | A1 | 8/2023 | Payne | |
| 2024/0391966 | A1 | 11/2024 | Payne | |
| 2025/0085297 | A1 | 3/2025 | Bettoun | |
| 2026/0055149 | A1 | 2/2026 | Payne | |

FOREIGN PATENT DOCUMENTS

| | | | | |
|---|---|---|---|---|
| AU | 2003279903 | A1 | 5/2004 | |
| CA | 2649538 | A1 | 11/2007 | |
| CA | 3147742 | A1 | 1/2021 | |
| CN | 103620036 | A | 3/2014 | |
| CN | 114450309 | A | 5/2022 | |
| EP | 2718439 | A1 | 4/2014 | |
| EP | 2750686 | A1 | 7/2014 | |
| JP | 2016-520557 | A | 7/2016 | |
| JP | 2023-518996 | A | 5/2023 | |
| WO | 2004/032863 | A2 | 4/2004 | |
| WO | 2007/124082 | A2 | 11/2007 | |
| WO | 2009/098682 | A2 | 8/2009 | |
| WO | 2011/103536 | A1 | 8/2011 | |
| WO | 2012/014083 | A2 | 2/2012 | |
| WO | 2012/050402 | A2 | 4/2012 | |
| WO | 2012/170771 | A1 | 12/2012 | |
| WO | WO-2012174452 | A1 * | 12/2012 | A61K 38/1709 |
| WO | 2013/071440 | A1 | 5/2013 | |
| WO | 2016/115632 | A1 | 7/2016 | |
| WO | WO-2016119856 | A1 * | 8/2016 | A61K 38/1703 |
| WO | 2016/172659 | A1 | 10/2016 | |
| WO | WO-2017165167 | A1 * | 9/2017 | A01K 67/0276 |
| WO | 2018/085436 | A1 | 5/2018 | |
| WO | 2021/011929 | A1 | 1/2021 | |

(Continued)

OTHER PUBLICATIONS

U.S. Appl. No. 16/942,276, filed Jul. 29, 2020, now U.S. Pat. No. 11,459,363, Issued.
U.S. Appl. No. 17/900,450, filed Aug. 31, 2022, 2023-0242600, Published.
U.S. Appl. No. 18/802,840, filed Aug. 13, 2024, Pending.
U.S. Appl. No. 17/627,638, filed Jan. 14, 2022, 2022-0378869, Published.
U.S. Appl. No. 17/631,414, filed Jan. 28, 2022, 2022-0276258, Published.
U.S. Appl. No. 17/105,149, filed Nov. 25, 2020, now U.S. Pat. No. 11,988,675, Issued.
U.S. Appl. No. 17/246,549, filed Apr. 30, 2021, now U.S. Pat. No. 11,976,100, Issued.

(Continued)

*Primary Examiner* — Sergio Coffa
(74) *Attorney, Agent, or Firm* — McCarter & English, LLP; Yelena Margolin; Jill Mello

(57) ABSTRACT

The present disclosure provides methods for treating or ameliorating a myelin associated disease or a mitochondria associated disease that comprising administering to a subject in need thereof a frataxin replacement therapeutic compound, e.g., a fusion protein comprising frataxin.

17 Claims, 21 Drawing Sheets

Specification includes a Sequence Listing.

(56) References Cited

FOREIGN PATENT DOCUMENTS

| | | | |
|---|---|---|---|
| WO | 2021/021931 | A1 | 2/2021 |
| WO | 2021/195597 | A2 | 9/2021 |

OTHER PUBLICATIONS

U.S. Appl. No. 18/433,336, filed Feb. 5, 2024, 2024-0343766, Published.

U.S. Appl. No. 17/549,770, filed Dec. 13, 2021, 2022-0193190, Published.

Abrahao et al., Milestones in Friedreich ataxia: more than a century and still learning. Neurogenetics. Jul. 2015;16(3):151-60.

Belbellaa et al., High Levels of Frataxin Overexpression Lead to Mitochondrial and Cardiac Toxicity in Mouse Models. Mol Ther Methods Clin Dev. Sep. 1, 2020;19:120-138.

Bencze et al., The structure and function of frataxin. Crit Rev Biochem Mol Biol. Sep.-Oct. 2006;41(5):269-91.

Bou-Abdallah et al., Iron binding and oxidation kinetics in frataxin CyaY of *Escherichia coli*. J Mol Biol. Aug. 6, 2004;341(2):605-15.

Chauhan et al., The taming of the cell penetrating domain of the HIV Tat: myths and realities. J Control Release. Feb. 12, 2007;117(2):148-62.

Correia et al., Conformational stability of human frataxin and effect of Friedreich's ataxia-related mutations on protein folding. Biochem J. Sep. 15, 2006;398(3):605-11.

European Medicines Agency, Public summary of opinion on orphan designation: Human Frataxin fused to TAT cell-penetrating peptide for the treatment of Friedreich's ataxia. Nov. 13, 2020. One page.

Gonzalez et al., Characterization of in vivo disposition of CTI-1601: a mitochondria targeted therapy for Friedreich's Ataxia. Drug Metabolism and Pharmacokinetics. 2020;35:S38, Abstract P55.

Guo et al., Liquid Chromatography-High Resolution Mass Spectrometry Analysis of Platelet Frataxin as a Protein Biomarker for the Rare Disease Friedreich's Ataxia. Anal Chem. Feb. 6, 2018;90(3):2216-2223.

Han et al., Mechanisms of iron and copper-frataxin interactions. Metallomics. Aug. 16, 2017;9(8):1073-85.

Hayashi et al., Oxidative stress in inherited mitochondrial diseases. Free Radic Biol Med. Nov. 2015;88(Pt A):10-7.

Jiang et al., Frataxin and Friedreich's Ataxia. Chinese Journal of Neuroscience. Oct. 31, 2003;36(5):385-387.

Khdour et al., Lipophilic methylene blue analogues enhance mitochondrial function and increase frataxin levels in a cellular model of Friedreich's ataxia. Bioorg Med Chem. Jul. 23, 2018;26(12):3359-3369.

Lazaropoulos et al., Frataxin levels in peripheral tissue in Friedreich ataxia. Ann Clin Transl Neurol. Aug. 2015;2(8):831-42.

Lu et al., Frataxin deficiency induces Schwann cell inflammation and death. Biochim Biophys Acta. Nov. 2009;1792(11):1052-61.

Mastrangelo, Clinical approach to neurodegenerative disorders in childhood: an updated overview. Acta Neurol Belg. Dec. 2019;119(4):511-21.

Mathis et al., The ataxic neuropathies. J Neurol. Oct. 2021;268(10):3675-3689.

Pandolfo, Drug Insight: antioxidant therapy in inherited ataxias. Nat Clin Pract Neurol. Feb. 2008;4(2):86-96.

Raynal et al., Quality assessment and optimization of purified protein samples: why and how? Microb Cell Fact. Dec. 30, 2014;13:180, 10 pages.

Sasarman et al., Tissue-specific responses to the LRPPRC founder mutation in French Canadian Leigh Syndrome. Hum Mol Genet. Jan. 15, 2015;24(2):480-91.

Shoichet et al., Frataxin promotes antioxidant defense in a thiol-dependent manner resulting in diminished malignant transformation in vitro. Hum Mol Genet. Apr. 1, 2002;11(7):815-21.

Stauber et al., Intracellular trafficking and interactions of the HIV-1 Tat protein. Virology. Dec. 5, 1998;252(1):126-36.

Vitte et al., Intracellular delivery of peptides via association with ubiquitin or SUMO-1 coupled to protein transduction domains. BMC Biotechnol. Feb. 29, 2008;8:24, 11 pages.

Vyas et al., A TAT-frataxin fusion protein increases lifespan and cardiac function in a conditional Friedreich's ataxia mouse model. Hum Mol Genet. Mar. 15, 2012;21(6):1230-47.

International Search Report and Written Opinion for Application No. PCT/US2020/044069, dated Oct. 28, 2020, 12 pages.

International Preliminary Report on Patentability for Application No. PCT/US2020/044069, dated Feb. 10, 2022, 9 pages.

International Search Report and Written Opinion for Application No. PCT/US2020/062355, dated Mar. 12, 2021, 13 pages.

International Search Report and Written Opinion for Application No. PCT/US2021/030348, dated Aug. 9, 2021, 24 pages.

International Search Report and Written Opinion for Application No. PCT/US2021/063163, dated Apr. 11, 2022, 16 pages.

Internatonal Search Report and Written Opinion for Application No. PCT/US2020/042683, dated Nov. 4, 2020, 12 pages.

International Search Report and Written Opinion for Application No. PCT/US2021/024534, dated Oct. 6, 2021, 15 pages.

International Search Report and Written Opinion for Application No. PCT/US2020/044118, dated Feb. 22, 2021, 20 pages.

Agrawal et al., CPPsite 2.0: a repository of experimentally validated cell-penetrating peptides. Nucleic Acids Res. Jan. 4, 2016;44(D1):D1098-103.

CPPsite2.0, Welcome to Statistics page CPPsite 2.0. Retrieved online at: <https://webs.iiitd.edu.in/raghava/cppsite/stats1.php.> 2 pages, Retrieved Jan. 2, 2025.

Guo et al., Protein tolerance to random amino acid change. Proc Natl Acad Sci U S A. Jun. 22, 2004;101(25):9205-10.

Lake et al., Leigh syndrome: One disorder, more than 75 monogenic causes. Ann Neurol. Feb. 2016;79(2):190-203.

Lowe, Not AlphaFold's Fault. In the pipeline. 6 pages. Sep. 7, 2022.

Massodi et al., Application of thermally responsive elastin-like polypeptide fused to a lactoferrin-derived peptide for treatment of pancreatic cancer. Molecules. Jun. 4, 2009;14(6):1999-2015.

Scopes, Enzyme Activity and Assays. Encyclopedia of Life Sciences. pp. 1-6, (2002).

Sutton et al., DIRAS3-Derived Peptide Inhibits Autophagy in Ovarian Cancer Cells by Binding to Beclin1. Cancers (Basel). Apr. 18, 2019;11(4):557, 14 pages.

Yampolsky et al., The exchangeability of amino acids in proteins. Genetics. Aug. 2005; 170(4):1459-72.

Carvalho et al., Mitochondrial dysfunction in demyelinating diseases. Semin Pediatr Neurol. Sep. 2013;20(3):194-201.

Kuramoto et al., A mutation in the gene encoding mitochondrial $Mg^{2+}$channel MRS2 results in demyelination in the rat. PLoS Genet. Jan. 6, 2011;7(1):e1001262, 10 pages.

Robinson et al., Lactic acidemia and mitochondrial disease. Mol Genet Metab. Sep.-Oct. 2006;89(1-2):3-13.

Wingfield, N-Terminal Methionine Processing. Curr Protoc Protein Sci. Apr. 3, 2018;88:6.14.1-6.14.3, 4 pages.

* cited by examiner

A

B

A

B

| | | | | | |
|---|---|---|---|---|---|
| ABCE1 | EGR2 | MT-CO2 | PTGS2 | Rpl39 | TMEM126A |
| ADAMTS1 | EGR3 | MT-CO3 | RNF2 | Rps15a | UBE2D3 |
| ARC | FXN | MT-ND1 | Rpl10 | Rps27l | UQCRC1 |
| ATF3 | IGF1 | MT-ND2 | Rpl24 | RTN4 | UQCRC2 |
| BTG2 | LOX | MT-ND3 | Rpl26 | RTN4IP1 (OPA10) | |
| CYCS | LRPPRC | MT-ND4 | Rpl32 | SERPINE1 | |
| CYR61 | MT-ATP6 | NR4A1 | Rpl37rt | SLIRP | |
| EGR1 | MT-ATP8 | PSMA3 | Rpl38 | THBS1 | |

Figure 2 (continued).

Control (SCRAMBLE KD #5)

B

LRPPRC KD (#21C)

C

D

A

B

A

* = p<0.05
*** = p<0.01
ns = not significant

B

* = p<0.05
*** = p<0.01
ns = not significant

A

B

A

Expression of Frataxin Sensitive Gene Markers (FSGMs) after treatment with vehicle or 20 μM exemplary TAT-FXN fusion protein

B

Expression of mature oligodendrocyte gene markers after treatment with vehicle or 20 μM exemplary TAT-FXN fusion protein

A

B

Expression of Schwann cell gene markers following treatment with vehicle or 20 μM exemplary TAT-FXN fusion protein

METHODS FOR TREATING MYELIN ASSOCIATED DISEASES AND MITOCHONDRIA ASSOCIATED DISEASES

RELATED APPLICATIONS

This application is a continuation of U.S. patent application Ser. No. 17/246,549, filed on Apr. 30, 2021; which claims priority to U.S. Provisional Application No. 63/018,451, filed on Apr. 30, 2020. The entire contents of each of the foregoing applications are hereby incorporated herein by reference.

SEQUENCE LISTING

The application contains a Sequence Listing which has been submitted electronically in .XML format and is hereby incorporated by reference in its entirety. Said .XML copy, created on Feb. 2, 2024, is named "130197-01103.xml" and is 76,601 bytes in size. The sequence listing contained in this .XML file is part of the specification and is hereby incorporated by reference herein in its entirety.

BACKGROUND

Myelin associated diseases are characterized by the presence of abnormal, e.g., defective or damaged, myelin. Myelin is a lipid rich substance that forms a white insulating sheath around axons of neurons. Myelin is deposited in layers around axons by oligodendrocytes in the central nervous system (CNS) and by Schwann cells in the peripheral nervous system (PNS). Damage or deficit in the myelin layer impairs the conduction of signals in the affected nerves and causes deficiencies in sensation, movement, cognition and other functions. Myelin associated diseases may result from genetic mutations or from the damage to myelin layer mediated by an immune reaction or exogenous or endogenous agents.

Mitochondria associated diseases are characterized by abnormal, e.g., defective, mitochondrial function. In subjects with a mitochondria associated disease, mitochondria fail to produce enough energy for proper functioning of various organs, such as brain, heart, liver, kidneys, eyes and ears. Mitochondria associated diseases are often inherited.

Currently, limited therapeutic options are available for treating myelin associated diseases and mitochondria associated diseases. Accordingly, new therapeutic methods for treating myelin associated diseases and mitochondria associated diseases are needed.

SUMMARY OF THE INVENTION

In some aspects, the present disclosure provides a method of treating a myelin associated disease, the method comprising administering to a subject in need thereof an effective amount of a frataxin (FXN) replacement therapeutic compound, such that the myelin associated disease in the subject is treated.

In some embodiments, administration of the FXN replacement therapeutic compound causes modulation of at least one a protein in said subject, wherein said at least one protein is selected from the group consisting of ABCE1, EIF1A, EGR 1, EGR2 (KROX20), EGR3, SERPINE1, CCN1 (CYR61), THBS1, NR41(Nurr77), RTN4 (NOGO), RTN4IP1 and TMEM126A.

In some aspects, the present disclosure provides a method of increasing the amount of myelin in a subject with a myelin associated disease, the method comprising administering to the subject an effective amount of a frataxin replacement therapeutic compound, such that the amount of myelin in the subject is increased.

In some aspects, the present disclosure provides a method of promoting oligodendrocyte maturation in a subject with a myelin associated disease, the method comprising administering to the subject an effective amount of a frataxin replacement therapeutic compound, such that oligodendrocyte maturation in the subject is increased.

In some aspects, the present disclosure provides a method of modulating a protein in a subject affected by a myelin associated disease, the method comprising administering to the subject an effective amount of a frataxin (FXN) replacement therapeutic compound such that the protein in the subject is modulated; wherein the protein is selected from the group consisting of ABCE1, EIF1A, EGR 1, EGR2 (KROX20), EGR3, SERPINE1, CCN1 (CYR61), THBS1, NR41(Nurr77), RTN4 (NOGO), RTN4IP1 and TMEM126A.

In some embodiments, the myelin associated disease is not Friedreich's Ataxia.

In some embodiments, the myelin associated disease is not Leigh Syndrome, French Canadian Type (LSFC).

In some embodiments, the myelin associated disease is a dysmyelination disease characterized by a malformed and/or defective myelin sheath present in the subject.

In some embodiments, the dysmyelination disease is a leukodystrophy.

In some embodiments, the leukodystrophy is selected from the group consisting of Vanishing White Matter Disease (VWMD) and X-Linked adrenoleukodystrophy (ALD).

In some embodiments, the myelin associated disease is a demyelination disease characterized by the destruction of previously normal myelin in the subject.

In some embodiments, the demyelination disease is a central demyelination disease.

In some embodiments, the central demyelination disease is an inflammatory or an immune central demyelination disease.

In some embodiments, the inflammatory or said immune central demyelination disease is selected from the group consisting of multiple sclerosis (MS), myelinoclastic diffuse sclerosis (Schilder's Disease), optic neuritis, acute disseminated encephalomyelitis (ADEM), acute hemorrhagic leucoencephalitis (AHL), paraneoplastic encephalomyelitis, rheumatoid arthritis, systemic lupus erythematosus, Behçet's disease and Sjörgen disease.

In some embodiments, the central demyelination disease is a toxic or metabolic central demyelination disease.

In some embodiments, the toxic or metabolic central demyelination disease is selected from the group consisting of a disorder associated with a vitamin B12 deficiency; central pontine myelinolysis, carbon monoxide poisoning; exposure to radiation and posterior reversible encephalopathy syndrome (PRES).

In some embodiments, the demyelination disease is a peripheral demyelination disease. In some embodiments, the peripheral demyelinating disease is selected from the group consisting of: Guillain-Barré Syndrome, chronic inflammatory demyelinating polyradiculoneuropathy (CIDP), paraproteinemic demyelinating neuropathy, progressive inflammatory neuropathy (PIN), Anti-Myelin Associated Glycoprotein (MAG) neuropathy, POEMS Syndrome, Charcot Marie Tooth Disease, and a copper deficiency associated disorder.

In some embodiments, the at least one symptom of the myelin associated disease is alleviated in the subject. In some embodiments, the at least one symptom is selected from the group consisting of ataxia, blurred vision, muscle weakness, muscle stiffness, muscle spasms, heart palpitations, dizziness, uncoordinated movements and fatigue.

In some aspects, the present disclosure also provides a method of treating a mitochondria associated disease, the method comprising administering to a subject in need thereof an effective amount of a frataxin (FXN) replacement therapeutic compound, such that the mitochondria associated disease in said subject is treated. In some embodiments, the administration of the FXN replacement therapeutic compound causes modulation of at least one a protein in said subject, wherein said protein is selected from the group consisting of MT-ND1, MT-ND2, MT-ND3, MT-ND4, MT-CO2, MT-CO3, MT-ATP6, MT-ATP8, CYCS, SLIRP, RTN4, and TMEM-126A.

In some aspects, the present disclosure provides a method of modulating a protein in a subject affected by a mitochondria associated disease, said method comprising administering to said subject an effective amount of a frataxin (FXN) replacement therapeutic compound such that said protein in said subject is modulated; wherein the protein is selected from the group consisting of MT-ND1, MT-ND2, MT-ND3, MT-ND4, MT-CO2, MT-CO3, MT-ATP6, MT-ATP8, CYCS, SLIRP, RTN4, and TMEM-126A.

In some embodiments, the mitochondria associated disease is not one or more of Friedreich's Ataxia, human mitochondrial trifunctional protein deficiency, sudden infant death syndrome, Kearns-Sayre syndrome, and Leber's Hereditary Optic Neuropathy.

In some embodiments, the mitochondria associated disease is not Leigh Syndrome, French Canadian Type (LSFC).

In some embodiments, the mitochondria associated disease is associated with a defect in the respiratory chain.

In some embodiments, the mitochondria associated disease is associated with a defect in mitochondrial DNA (mtDNA).

In some embodiments, the mitochondria associated disease is selected from the group consisting of Complex I Deficiency, Complex II Deficiency, Complex III Deficiency, Complex IV Deficiency, Complex V Deficiency, MELAS and Leigh Disease.

In some embodiments, at least one symptom of the mitochondria associated disease is alleviated in the subject. In some embodiments, the at least one symptom is selected from the group consisting of: fatigue, weakness, metabolic strokes, seizure, cardiomyopathy, arrhythmia, developmental disability, cognitive disability, diabetes mellitus, impaired hearing, impaired vision, impaired growth, impaired liver function, impaired gastrointestinal function, and impaired kidney function.

In some embodiments, the disease is a myelin and mitochondria associated disease.

In some aspects, the present disclosure provides a method of treating lactic acidosis in a subject with a mitochondria associated disease, the method comprising administering to the subject an effective amount of a frataxin (FXN) replacement therapeutic compound, such that the lactic acidosis in the subject is treated.

In some aspects, the present disclosure provides a method of treating lactic acidosis in a subject with a myelin and mitochondria associated disease, the method comprising administering to the subject an effective amount of a frataxin (FXN) replacement therapeutic compound, such that the lactic acidosis in the subject is treated.

In some aspects, the present disclosure provides a method of treating Charcot Marie Tooth Disease (CMT), the method comprising administering to a subject in need thereof an effective amount of a frataxin (FXN) replacement therapeutic compound, such that the lactic acidosis in the subject is treated.

In some embodiments, the CMT is selected from the group consisting of CMT type 1A (CMT1A) associated with the duplication the PMP22 gene; CMT type 2A2 (CMT2A2) associated with mutations in the gene MFN2 gene; X-linked CMT (CMTX) associated with a mutation in the GJB1 gene; CMT type 1B (CMT1B) associated with a mutation in the MPZ gene; and CMT type 4 (CMT4) associated with a mutation in the GDAP1 gene or a SURF1 gene.

In some aspects, the present disclosure provides a method of promoting neuronal survival in a subject in with, the method comprising administering to said subject an effective amount of a frataxin (FXN) replacement therapeutic compound, such that neuronal survival in the subject is promoted.

In some embodiments, the subject has a myelin associated disease. In some embodiments, the subject has a myelin and a mitochondria associated disease.

In some embodiments, administering of the FXN replacement therapeutic compound to said subject modulates at least one protein in said subject, wherein said at least one protein is selected from the group consisting of CYR61, EGR1 and NR4A1.

In some embodiments, the frataxin replacement therapeutic compound comprises a frataxin protein or a nucleic acid sequence encoding a frataxin protein. In some embodiments, the frataxin replacement therapeutic compound comprises a frataxin fusion protein comprising a frataxin protein, or a fragment or variant thereof, and an additional amino acid sequence.

In some embodiments, the frataxin fusion protein comprises a frataxin protein comprising an amino acid sequence of SEQ ID NO: 1, or a fragment, variant or derivative of SEQ ID NO: 1. In some embodiments, the frataxin fusion protein comprises a frataxin protein comprising an amino acid sequence having at least about 85% sequence identity to SEQ ID NO: 1. In some embodiments, the frataxin fusion protein comprises a frataxin protein comprising an amino acid sequence having at least about 90%, at least about 95% or at least about 99% sequence identity to SEQ ID NO: 1.

In some embodiments, the additional amino acid sequence comprises a cell penetrating peptide (CPP). In some embodiments, the CPP comprises a peptide selected from the group of CPPs listed in the Database of Cell-Penetrating Peptides CPPsite 2.0. In some embodiments, the CPP comprises a peptide selected from the group consisting of a transduction domain of HIV-TAT, galanin, mastoparan, transportan, penetratin, polyarginine, VP22, and a variant or derivative thereof.

In some embodiments, the CPP comprises the transduction domain of HIV-TAT comprising or consisting of the amino acid sequence of SEQ ID NO: 3, or a fragment, variant or derivative of SEQ ID NO: 3. In some embodiments, the frataxin replacement therapeutic compound comprises a frataxin fusion protein comprising or consisting of the amino acid sequence of SEQ ID NO: 22.

In some embodiments, the frataxin replacement therapeutic compound comprises a frataxin fusion protein comprising or consisting of an amino acid sequence having at least about 85% sequence identity to SEQ ID NO: 22. In some embodiments, the FXN replacement therapeutic compound comprises a frataxin fusion protein comprising or consisting of an amino acid sequence having at least about 90%, at least about 95% or at least about 99% sequence identity to SEQ ID NO: 22.

In some embodiments, the frataxin fusion protein further comprises a target enhancing sequence (TES). In some embodiments, the CPP is located at the N-terminus of the frataxin fusion protein and wherein the TES is fused at the C-terminus of the CPP.

In some embodiments, the frataxin fusion protein comprises or consists of, starting at the N-terminus: CPP; TES; and full-length frataxin (SEQ ID NO: 1).

In some embodiments, the CPP is located at the C-terminus of the fusion protein and wherein the TES is fused at the N-terminus of the CPP. In some embodiments, the frataxin fusion protein comprises or consists of, starting at the N-terminus: full-length FXN (SEQ ID NO: 1); TES; and CPP.

In some embodiments, the TES comprises a nuclear export signal peptide. In some embodiments, the nuclear export signal peptide comprises a sequence having at least 85% sequence identity to any one of SEQ ID NOs. 42-49. In some embodiments, the nuclear export signal peptide comprises a peptide selected from the group consisting of NES1, NES2, NES3, NES4, NES5, NES6, NES7, NES8, and a variant or derivative thereof. In some embodiments, the nuclear export signal peptide comprises a peptide selected from the group consisting of NES1 and NES2, or a variant or derivative thereof.

In some embodiments, the TES comprises a protease sensitive peptide. In some embodiments, the protease sensitive peptide comprises a ubiquitin-like modifier. In some embodiments, the protease sensitive peptide comprises an amino acid sequence having at least 85% sequence identity to any one of SEQ ID NOs. 23-41. In some embodiments, the protease sensitive peptide comprises an amino acid sequence having at least 85% sequence identity to human ubiquitin (SEQ ID NO: 23). In some embodiments, the protease sensitive peptide comprises an amino acid sequence having at least 85% sequence identity to a calpain cleavage domain EPLFAERK (SEQ ID NO: 25). In some embodiments, the protease sensitive peptide comprises a peptide selected from the group consisting of ubiquitin, a caspase cleavage domain, a calpain cleavage domain, SUMO1, SUMO2, SUMO3, SUMO4, ISG15, Atg8, Atg12, NEDD8, and a variant or derivative thereof.

In some embodiments, the frataxin fusion protein comprises an amino acid sequence having at least 85%, 90%, or 95% sequence identity to any of SEQ ID NOs. 50-57.

In some embodiments, the subject is a human.

In some embodiments, the present disclosure provides methods for treating a myelin associated disease, that comprise administering to a subject in need thereof an effective amount of a frataxin (FXN) replacement therapeutic compound, such that the myelin associated disease in the subject is treated.

In some embodiments, the present disclosure also provides methods of modulating a protein in a subject affected by a myelin associated disease, that comprise administering to the subject an effective amount of a frataxin (FXN) replacement therapeutic compound such that the protein in the subject is modulated; wherein the protein is selected from the group consisting of ABCE1, EIF1A, EGR 1, EGR2 (KROX20), EGR3, SERPINE1, CCN1 (CYR61), THBS1, NR41(Nurr77), RTN4 (NOGO), RTN4IP1 and TMEM126A.

In some aspects, the myelin associated disease is not Friedreich's Ataxia. In some aspects, the myelin associated disease is not Leigh Syndrome, French Canadian Type (LSFC).

In some aspects, the myelin associated disease is a dysmyelination disease characterized by a malformed and/or defective myelin sheath present in the subject. In one aspect, the dysmyelination disease is a leukodystrophy, e.g., selected from the group consisting of Vanishing White Matter Disease (VWMD) and X-Linked adrenoleukodystrophy (ALD).

In some embodiments, the myelin associated disease is a demyelination disease characterized by the destruction of previously normal myelin in the subject. In a further embodiment, the demyelination disease is a central demyelination disease, e.g., an inflammatory or an immune central demyelination disease. In one aspect, the inflammatory or the immune central demyelination disease is selected from the group consisting of multiple sclerosis (MS), myelinoclastic diffuse sclerosis (Schilder's Disease), optic neuritis, acute disseminated encephalomyelitis (ADEM), acute hemorrhagic leucoencephalitis (AHL), paraneoplastic encephalomyelitis, rheumatoid arthritis, systemic lupus erythematosus, Behçet's disease and Sjörgen disease.

In some embodiments, the central demyelination disease is a toxic or metabolic central demyelination disease, e.g., selected from the group consisting of a disorder associated with a vitamin B12 deficiency; central pontine myelinolysis, carbon monoxide poisoning; exposure to radiation and posterior reversible encephalopathy syndrome (PRES).

In some embodiments, the demyelination disease is a peripheral demyelination disease, e.g., selected from the group consisting of: Guillain-Barré Syndrome, chronic inflammatory demyelinating polyradiculoneuropathy (CIDP), paraproteinemic demyelinating neuropathy, progressive inflammatory neuropathy (PIN), Anti-Myelin Associated Glycoprotein (MAG) neuropathy, POEMS Syndrome, Charcot Marie Tooth Disease, and a copper deficiency associated disorder.

In some aspects, at least one symptom of the myelin associated disease is alleviated in the subject. In further aspects, the at least one symptom is selected from the group consisting of ataxia, blurred vision, muscle weakness, muscle stiffness, muscle spasms, heart palpitations, dizziness, uncoordinated movements and fatigue.

In some embodiments, the present disclosure also provides methods for treating a mitochondria associated disease that comprise administering to a subject in need thereof an effective amount of a frataxin (FXN) replacement therapeutic compound, such that the mitochondria associated disease in the subject is treated.

In some embodiments, the present disclosure also provides a method of modulating a protein in a subject affected by a mitochondria associated disease that comprises administering to the subject an effective amount of a frataxin (FXN) replacement therapeutic compound such that the protein in the subject is modulated; wherein the protein is selected from the group consisting of MT-ND1, MT-ND2, MT-ND3, MT-ND4, MT-CO2, MT-CO3, MT-ATP6, MT-ATP8, CYCS, SLIRP, RTN4, and TMEM-126A.

In some aspects, the mitochondria associated disease is not one or more of Friedreich's Ataxia, human mitochondrial trifunctional protein deficiency, sudden infant death syndrome, Kearns-Sayre syndrome, and Leber's Hereditary Optic Neuropathy. In some aspects, the mitochondria associated disease is not Leigh Syndrome, French Canadian Type (LSFC).

In some embodiments, the mitochondria associated disease is associated with a defect in the respiratory chain. In some embodiments, the mitochondria associated disease is associated with a defect in mitochondrial DNA (mtDNA).

In some aspects, the mitochondria associated disease is selected from the group consisting of Complex I Deficiency, Complex II Deficiency, Complex III Deficiency, Complex IV Deficiency, Complex V Deficiency, MELAS and Leigh Disease.

In some embodiments, at least one symptom of the mitochondria associated disease is alleviated in the subject. In some embodiments, the at least one symptom is selected from the group consisting of: fatigue, weakness, metabolic strokes, seizure, cardiomyopathy, arrhythmia, developmental disability, cognitive disability, diabetes mellitus, impaired hearing, impaired vision, impaired growth, impaired liver function, impaired gastrointestinal function, and impaired kidney function.

In some aspects, the frataxin replacement therapeutic compound comprises a frataxin protein or a nucleic acid sequence encoding a frataxin protein. In some aspects, the frataxin replacement therapeutic compound comprises a frataxin fusion protein comprising a frataxin protein, or a fragment or variant thereof, and an additional amino acid sequence.

In some embodiments, the frataxin fusion protein comprises a frataxin protein comprising an amino acid sequence of SEQ ID NO: 1, or a fragment, variant or derivative of SEQ ID NO: 1.

In some embodiments, the frataxin fusion protein comprises a frataxin protein comprising an amino acid sequence having at least about 85% sequence identity to SEQ ID NO: 1.

In some embodiments, the frataxin fusion protein comprises a frataxin protein comprising an amino acid sequence having at least about 90%, at least about 95% or at least about 99% sequence identity to SEQ ID NO: 1.

In some aspects, the additional amino acid sequence comprises a cell penetrating peptide (CPP). In further aspects, the CPP comprises a peptide selected from the group of CPPs listed in the Database of Cell-Penetrating Peptides CPPsite 2.0. In other aspects, the CPP comprises a peptide selected from the group consisting of a transduction domain of HIV-TAT, galanin, mastoparan, transportan, penetratin, polyarginine, VP22, and a variant or derivative thereof.

In one embodiment, the CPP comprises the transduction domain of HIV-TAT comprising or consisting of the amino acid sequence of SEQ ID NO: 3, or a fragment, variant or derivative of SEQ ID NO:3.

In some embodiments, the frataxin replacement therapeutic compound comprises a frataxin fusion protein comprising or consisting of the amino acid sequence of SEQ ID NO: 22. In some embodiments, the frataxin replacement therapeutic compound comprises a frataxin fusion protein comprising or consisting of an amino acid sequence having at least about 85% sequence identity to SEQ ID NO: 22. In some embodiments, the FXN replacement therapeutic compound comprises a frataxin fusion protein comprising or consisting of an amino acid sequence having at least about 90%, at least about 95% or at least about 99% sequence identity to SEQ ID NO: 22.

BRIEF DESCRIPTION OF THE FIGURES

FIG. 1, panel B is a bar graph illustrating the fold change in gene expression in the heart tissue of KO mice treated with Vehicle vs. the heart tissue of KO mice treated with an exemplary TAT-hFXN fusion protein.

FIG. 2, panel B shows the list of genes that were used to generate the String Model shown in FIG. 2, panel A.

FIG. 3, panel B shows the effect of NGF and EGF treatment on the expression of selected FSGMs in PC12 cells.

FIG. 4, panel B is a picture of culture dishes containing LRPPRC-KD cells treated with different concentrations (0-20 μM) of the exemplary TAT-hFXN fusion protein. FIG. 4, panel C is a bar graph showing the amount of lactate in the media from scramble control and LRPPRC-KD cells after treatment with 0 μM and 20 μM exemplary TAT-hFXN fusion protein. FIG. 4, panel D is a series of microscopic images showing scramble control cells (labeled as "SCR-5") and LRPPRC-KD cells (labeled as "21C") after treatment with vehicle or the exemplary TAT-hFXN fusion protein.

FIG. 5, panel B is a dot plot showing plasma levels of pNfH in wild-type and Ndufs4 KO mouse model of Leigh Syndrome and demyelination following treatment with vehicle (as a negative control) and the exemplary TAT-hFXN fusion protein.

FIG. 6, panel B is a dot plot showing plasma levels of NfL in cuprizone/rapamycin treated mouse model of demyelination following treatment with vehicle, T3 and the exemplary TAT-hFXN fusion protein.

FIG. 7, panel B is bar graph showing relative expression levels of certain FSGMS in differentiated and undifferentiated oligodendrocytes.

FIG. 8, panel B is a bar graph showing relative expression levels in mature oligodendrocytes of certain mature oligodendrocyte gene markers after treatment with vehicle or 20 μM exemplary TAT-hFXN fusion protein.

FIG. 9, panel B is a bar graph showing relative expression levels in Schwann cells of certain Schwann cells gene markers after treatment with vehicle or 20 μM exemplary TAT-hFXN fusion protein.

DETAILED DESCRIPTION

Figure 1:
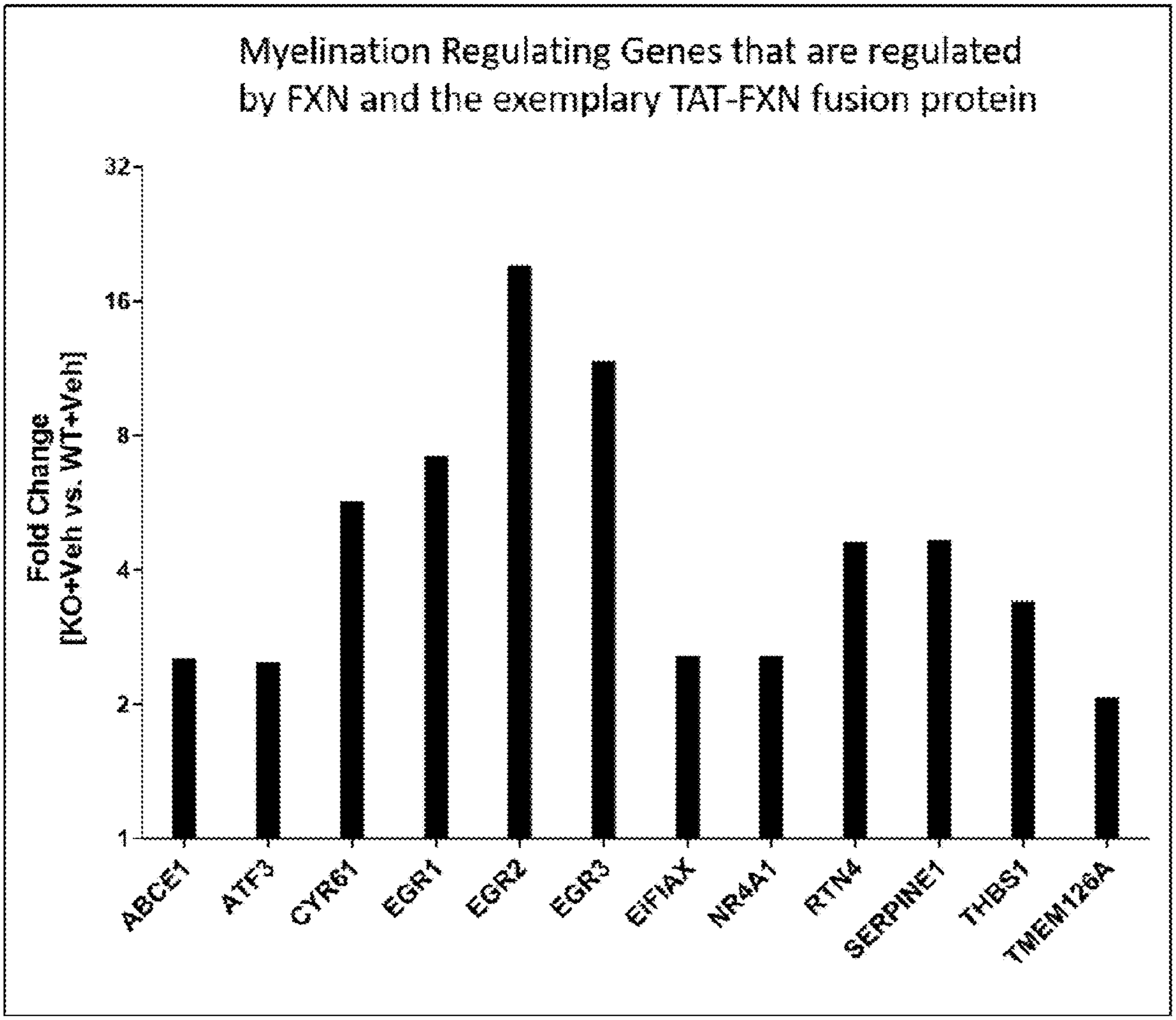
FIG. 1 is a series of bar graphs showing 12 FXN-sensitive genomic markers (FSGMs) selected from Table 11. Specifically, FIG. 1, panel A is a bar graph illustrating the fold change in gene expression in the heart tissue of WT mice treated with Vehicle vs. the heart tissue of KO mice treated with Vehicle.
Figure 1:
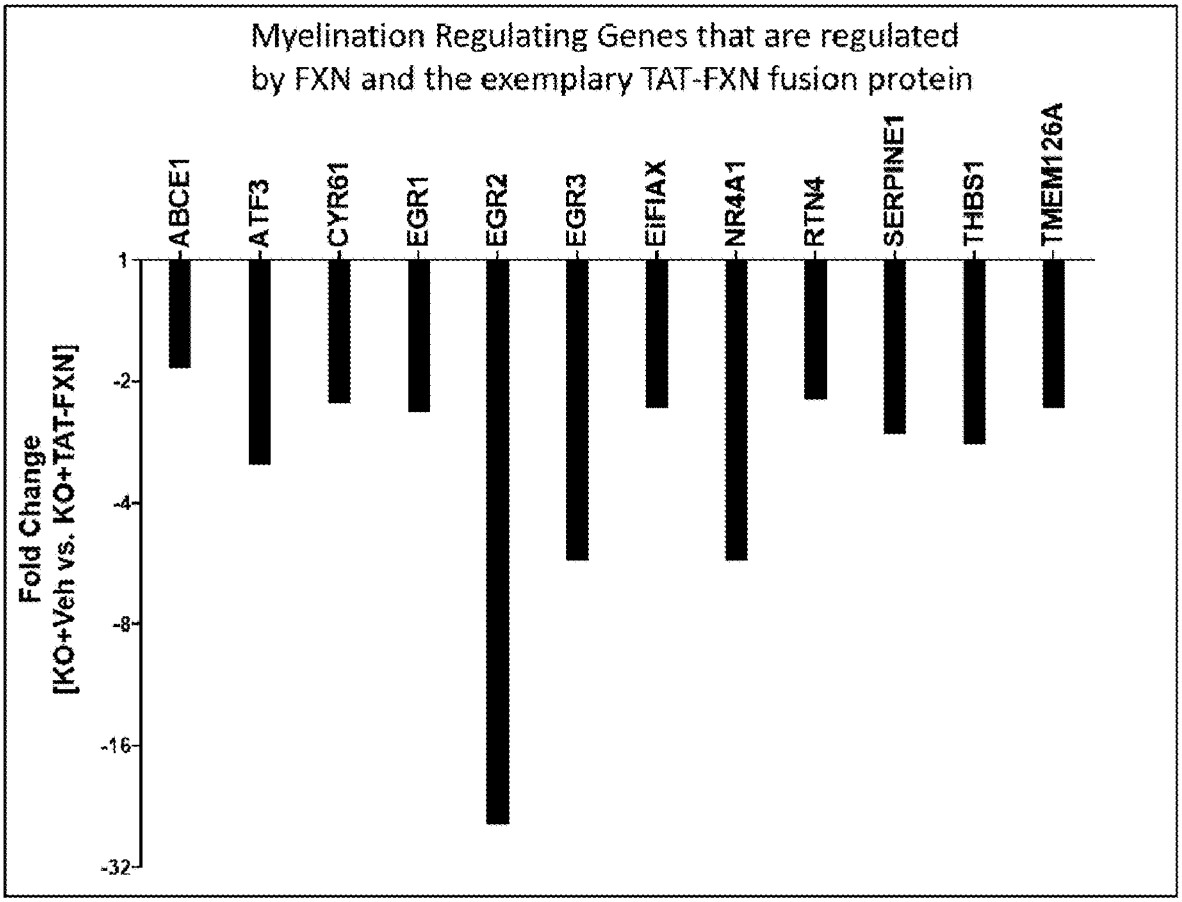

The present disclosure provides methods for treating or ameliorating a myelin associated disease that comprise administering to a subject in need thereof a frataxin replacement therapeutic compound. The present disclosure also provides methods for treating or ameliorating a mitochondria associated disease, e.g., a myelin and mitochondria associated disease, that comprise administering to a subject in need thereof a frataxin replacement therapeutic compound. The present disclosure is based on a surprising discovery that administration of a frataxin replacement therapeutic compound, such as a fusion protein comprising frataxin, e.g., TAT-hFXN fusion protein as described below, can modulate the expression of genes involved in myelination and/or mitochondrial function. Modulating the expression of genes involved in myelination and/or mitochondrial function is expected to have a beneficial effect on myelination and/or mitochondrial function and to help treat or ameliorate a myelin associated disease or a mitochondria associated disease. For example, the present inventors have demonstrated that administration of a frataxin replacement therapeutic compound to two different mouse models of demyelination can decrease levels of neurodegeneration biomarkers in the mouse models, indicating a decrease in the levels of neurodegeneration. The present inventors have also demonstrated that administration of a frataxin replacement therapeutic compound to oligodendrocytes and Schwann cells causes an increase in the levels of mature maturation markers in these cells, indicating that administration of a frataxin replacement therapeutic compound can lead to an increase in myelination.

The present disclosure is also based on a surprising discovery that administration of a frataxin replacement therapeutic compound, such as a fusion protein comprising frataxin, e.g., TAT-hFXN fusion protein, to cells exhibiting a deficiency in the mitochondrial function can reverse the effect of mitochondrial function impairment.

I. Frataxin (FXN) Replacement Therapeutics

Methods provided by the present disclosure involve frataxin replacement therapy, and comprise administering to a subject in need thereof an effective amount of a frataxin (FXN) replacement therapeutic compound.

As used herein, the term "frataxin replacement therapy" or "FXN replacement therapy" refers to replacement of frataxin in a subject which results in increased expression or activity of frataxin in the subject. FXN replacement therapy involves the administration of an FXN replacement therapeutic compound to a subject in need. The FXN replacement therapeutic compound may be provided by FXN protein delivery or through delivery of a nucleic acid encoding FXN to a subject. FXN protein delivery to the subject can include delivery of FXN protein or delivery of a FXN fusion protein. An "FXN protein", as used herein, encompasses full length or mature FXN (e.g., human FXN, e.g., full-length or mature hFXN) or a variant or a fragment of FXN (e.g., biologically active fragment of FXN). In some embodiments, an FXN protein is full-length hFXN (SEQ ID NO: 1) or mature hFXN (SEQ ID NO: 2), as described herein, or a variant or fragment thereof.

As used herein, the term "FXN fusion protein" refers to full length FXN protein or a variant or fragment of FXN (e.g., a biologically active fragment of FXN) fused to a full length or a fragment of a different protein, or to a peptide. In some embodiments, an FXN fusion protein comprises full-length hFXN (SEQ ID NO: 1) or mature hFXN (SEQ ID NO: 2), as described herein. In some embodiments, the FXN protein or fragment thereof is fused to a cell penetrating peptide (CPP). In some embodiments, the CPP is an HIV-TAT polypeptide.

Frataxin, or FXN, e.g., human FXN (hFXN), is associated with a disorder Friedreich's Ataxia (FRDA). FRDA is a genetic, progressive neurodegenerative disorder caused by a mutation in the gene FXN encoding frataxin. Frataxin is an essential and phylogenetically conserved protein that is found in cells throughout the body, with the highest levels in the heart, spinal cord, liver, pancreas, and skeletal muscle. Frataxin is encoded in the nucleus, expressed in the cytoplasm and imported into the mitochondria where it is processed to the mature form. In humans, the 210-amino acid full-length frataxin protein ($hFXN_{1-210}$, 23.1 kDa) contains a typical mitochondrial targeting sequence (MTS) at the amino terminus that is processed in a 2-step cleavage by the mitochondrial matrix processing peptidase (MPP) as it is imported into the mitochondrial matrix. The resulting protein is a 130-amino acid, 14.2 kDa mature frataxin protein ($hFXN_{81-210}$). Amino acid sequences of the full-length frataxin and mature frataxin are shown in Table 1 below.

The term "frataxin" or "FXN", as used herein, encompasses full-length frataxin and mature frataxin from any subject and encompasses, e.g., human frataxin. The term "human frataxin" or "hFXN", as used herein, encompasses the full-length human frataxin (SEQ ID NO: 1) and mature human frataxin (SEQ ID NO: 2).

TABLE 1

Amino acid sequences of human frataxin

| SEQ ID NO. | Protein | Amino Acid Sequence |
|---|---|---|
| 1 | Full-length hFXN $hFXN_{1-210}$ | MWTLGRRAVAGLLASPSPAQAQTLTRVPRPAELAPLCGRRGL RTDIDATCTPRRASSNQRGLNQIWNVKKQSVYLMNLRKSGTL GHPGSLDETTYERLAEETLDSLAEFFEDLADKPYTFEDYDVSFG SGVLTVKLGGDLGTYVINKQTPNKQIWLSSPSSGPKRYDWTGK NWVYSHDGVSLHELLAAELTKALKTKLDLSSLAYSGKDA |
| 2 | Mature hFXN $hFXN_{81-210}$ | SGTLGHPGSLDETTYERLAEETLDSLAEFFEDLADKPYTFEDYD VSFGSGVLTVKLGGDLGTYVINKQTPNKQIWLSSPSSGPKRYD WTGKNWVYSHDGVSLHELLAAELTKALKTKLDLSSLAYSGK DA |

In some embodiments, the term "frataxin replacement therapeutic compound" or "FXN replacement therapeutic compound" refers to a frataxin replacement therapeutic comprising a polypeptide comprising or consisting of frataxin, such as human frataxin, e.g., full-length human frataxin (SEQ ID NO: 1) or mature human frataxin (SEQ ID NO: 2), or a fragment or variant thereof. The term "frataxin replacement therapeutic" or "FXN replacement therapeutic", as used herein, also encompasses a frataxin replacement therapeutic comprising a polypeptide comprising or consisting of an amino acid sequence having at least 85%, at least 90%, at least 95% or at least 99% sequence identity to SEQ ID NO: 1 or SEQ ID NO: 2, or a fragment thereof.

In other embodiments, the term "frataxin replacement therapeutic compound" or "FXN replacement therapeutic compound" may also refer to a frataxin replacement therapeutic comprising a nucleic acid sequence encoding a polypeptide comprising or consisting of frataxin, such as human frataxin, e.g., the full-length hFXN (SEQ ID NO: 1) or mature human frataxin (SEQ ID NO: 2), or a fragment or variant thereof. The term "frataxin replacement therapeutic" or "FXN replacement therapeutic", as used herein, may also encompass a frataxin replacement therapeutic comprising a nucleic acid sequence encoding a polypeptide that comprises or consists of an amino acid sequence having at least 85%, at least 90%, at least 95% or at least 99% sequence identity to SEQ ID NO: 1 or SEQ ID NO: 2, or a fragment.

As used herein, the term "nucleic acid" is interchangeable with the term "polynucleotide(s)" and generally refers to any polyribonucleotide or poly-deoxyribonucleotide, which may be unmodified RNA or DNA or modified RNA or DNA or any combination thereof. The term "nucleic acid" encompasses, without limitation, single- and double-stranded nucleic acids.

In some embodiments, the term "frataxin replacement therapeutic compound" or "FXN replacement therapeutic compound", as used herein, may also encompass a frataxin replacement therapeutic comprising a polypeptide comprising or consisting of a frataxin fragment. In other embodiments, the term "frataxin replacement therapeutic compound" or "FXN replacement therapeutic compound" may encompass a frataxin replacement therapeutic comprising a nucleic acid sequence that encodes a polypeptide comprising or consisting of a frataxin fragment. The term "frataxin fragment", which may be used herein interchangeably with the terms "fragment of frataxin" and "a portion of frataxin", encompasses any polypeptide that is shorter than a full-length frataxin or mature frataxin, e.g., shorter than human full-length frataxin (SEQ ID NO: 1) or human mature frataxin (SEQ ID NO: 2).

In preferred embodiments, a frataxin fragment may have a biological activity of frataxin, i.e., a biologically active fragment of frataxin. For example, in some embodiments, a frataxin fragment may have substantially the same biological activity as full length or mature frataxin, e.g., human full-length frataxin (SEQ ID NO: 1) or human mature frataxin (SEQ ID NO: 2). In other embodiments, a frataxin fragment may have partial biological activity of frataxin, for example, about 30% to about 100%, e.g., about 30% to about 60%, about 50% to about 80% or about 60% to about 95% of the biological activity of full length or mature frataxin, e.g., human full-length frataxin (SEQ ID NO; 1) or human mature frataxin (SEQ ID NO: 2).

The term "frataxin replacement therapeutic compound", as used herein, also encompasses a frataxin replacement therapeutic comprising an FXN fusion protein comprising full length or mature frataxin, or a fragment or a variant thereof, e.g., human frataxin, and an additional amino acid sequence. For example, the fusion protein may comprise the amino acid sequence of SEQ ID NO: 1, or SEQ ID NO: 2, or an amino acid sequence having at least 85%, at least 90%, at least 95% or at least 99% sequence identity to SEQ ID NO: 1 or SEQ ID NO: 2, and an additional amino acid sequence.

In some embodiments, the additional amino acid sequence of the fusion protein may comprise a cell penetrating peptide (CPP). Cell penetrating peptides (CPPs) are short peptide sequences, typically between 5 and 30 amino acids long, that can facilitate cellular intake of various molecular cargo, such as proteins. When present in a fusion protein, a CPP facilitates the delivery of the fusion protein to a cell, e.g., a recipient cell. A CPP comprised in a fusion protein comprising frataxin as described herein may be any CPP known to the person skilled in the art, such as for example a transduction domain of HIV-TAT (also referred to herein as TAT), galanin, mastoparan, transportan, penetratin, polyarginine, or VP22. In one specific embodiment, the CPP comprises or consists of a transduction domain of HIV-TAT protein having the amino acid sequence YGRKKRRQRRR (SEQ ID NO: 3) or an amino acid sequence MYGRKKRRQRRR (SEQ ID NO: 4). In other embodiments, the CPP may comprise or consist of an amino acid sequence having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 3 or SEQ ID NO: 4. Table 2 below lists amino acid sequences of exemplary CPPs.

TABLE 2

Exemplary CPPs and corresponding amino acid sequences

| SEQ ID NO. | CPP | Amino Acid Sequence |
|---|---|---|
| 3 | HIV-TAT | YGRKKRRQRRR |
| 4 | HIV-TAT + M | MYGRKKRRQRRR |
| 5 | Galanin | GWTLNSAGYLLGPHAVGNHRSFSDKNGLTS |
| 6 | Mastoparan | INLKALAALAKKIL-$NH_2$ |
| 7 | Transportan | GWTLNSAGYLLGKINLKALAALAKKIL |
| 8 | Penetratin | RQIKIWFQNRRMKWKK |
| 9 | Polyarginine | RRRRRRRRR |
| 10 | VP22 | DAATATRGRSAASRPTERPRAPARSASRPRRPVE |

In some examples, the CPP comprised in a fusion protein of the present disclosure may comprise an amino acid sequence having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of the amino acid sequences listed in Table 2, i.e., SEQ ID NO: 5, SEQ ID NO: 6, SEQ ID NO: 7, SEQ ID NO: 8, SEQ ID NO: 9, or SEQ ID NO: 10. In some examples, the CPP comprised in a fusion proteins of the present disclosure may comprise a functional analogue, derivative or a fragment of SEQ ID NO: 1 or SEQ ID NO: 2 and any CPP listed in Table 2, i.e., SEQ ID NO: 6, SEQ ID NO: 7, SEQ ID NO: 8, SEQ ID NO: 9, or SEQ ID NO: 10.

The additional amino acid sequence present in the fusion protein may also comprise a peptide useful in protein delivery, such as a protein transduction domain, an amphipathic peptide, e.g., MAP, KALA, ppTG20, a proline-rich peptide, an MPG-derived peptide, Pep-1, and also a loligomer, an arginine-rich peptide, or a calcitonin-derived peptide.

In the fusion protein comprising frataxin, the different (heterologous) protein or peptide, e.g., CPP or a peptide useful in protein delivery as described above, may be directly or indirectly (through a linker) linked to either the N- or the C-terminus of frataxin. As used herein, the term "directly" means that the (first or last) amino acid at the terminal end (N or C-terminal end) of the polypeptide is fused to the (first or last) amino acid at the terminal end (N or C-terminal end) of the heterologous polypeptide. In other words, in this embodiment, the last amino acid of the C-terminal end of said polypeptide is directly linked by a covalent bond to the first amino acid of the N-terminal end of said heterologous polypeptide, or the first amino acid of the N-terminal end of said polypeptide is directly linked by a covalent bond to the last amino acid of the C-terminal end of said heterologous polypeptide.

As used herein, the term "linker", which may be used interchangeably with the term "spacer", refers to a sequence of at least one amino acid that links the polypeptides and proteins comprised in the fusion protein described in the present disclosure. Such a linker may be useful to prevent steric hindrances. The length of a linker may vary from 2 to 31 amino acids, optimized for each condition so that the linker does not impose any constraints on the conformation or interactions of the linked partners of the fusion protein. Linkers have been described in the literature both as endogenous, naturally occurring, playing a role in separating domains within a protein or for the formation of dimers. Alternatively, linkers have been described in recombinant technology for the generation of fusion proteins. Exemplary linkers that may be comprised in the fusion protein of the present disclosure are shown in Table 3 below.

TABLE 3

Linkers

| SEQ ID NO. | Linker Amino Acid Sequence |
|---|---|
| 11 | GGGGSLVPRGSGGGGS |
| 12 | GSGSGS |
| 13 | GSGSGSGS |
| 14 | GGSGGHMGSGG |
| 15 | GGSGGSGGSGG |
| 16 | GGSGG |
| 17 | GGGSEGGGSEGGGSEGGG |
| 18 | AAGAATAA |
| 19 | GGGGG |
| 20 | GGSSG |
| 21 | GSGGGTGGGSG<br>GT<br>GG |

In some embodiments, the frataxin replacement therapeutic compound, as used herein, comprises a fusion protein described, e.g., in WO2021021931A1, the entire contents of which are hereby incorporated herein by reference. This fusion protein, which may also be referred herein as "an exemplary TAT-hFXN fusion protein", comprises the transduction domain of HIV-TAT protein (SEQ ID NO: 3) as CPP, linked through a GG linker to the N-terminus of human frataxin. The human frataxin comprised in the exemplary TAT-hFXN fusion protein is the full-length human frataxin ($hFXN_{1-210}$; SEQ ID NO: 1) as described herein. As the exemplary TAT-hFXN fusion protein is imported into the mitochondrial matrix, it is cleaved at amino acid 81, yielding the mature human frataxin (hFXN81-210; SEQ ID NO: 2). The exemplary TAT-hFXN fusion protein has the amino acid sequence as shown in Table 4 below (SEQ ID NO: 22):

TABLE 4

Amino acid sequence of the exemplary TAT-hFXN fusion protein

| SEQ ID NO. | Protein | Amino Acid Sequence |
|---|---|---|
| 22 | Exemplary TAT-hFXN fusion protein | MYGRKKRRQRRRGGMWTLGRRAVAGLLASPS<br>PAQAQTLTRVPRPAELAPLCGRRGLRTDIDA<br>TCTPRRASSNQRGLNQIWNVKKQSVYLMNLR<br>KSGTLGHPGSLDETTYERLAEETLDSLAEFF<br>EDLADKPYTFEDYDVSFGSGVLTVKLGGDLG<br>TYVINKQTPNKQIWLSSPSSGPKRYDWTGKN<br>WVYSHDGVSLHELLAAELTKALKTKLDLSSL<br>AYSGKDA |

In some embodiments, the frataxin replacement therapeutic compound, as used herein, comprises, or consists of, an amino acid sequence having at least 85%, e.g., at least 90%, at least 95%, at least 99% or 100% sequence identity to SEQ ID NO: 22.

In some embodiments, the term "frataxin replacement therapeutic compound" also encompasses a frataxin replacement therapeutic comprising a nucleic acid sequence (e.g., a vector) that encodes a frataxin protein, e.g., human frataxin (hFXN). For example, the nucleic acid sequence may encode an amino acid sequence comprising full length frataxin or mature frataxin (e.g., human frataxin), or a fragment of frataxin (e.g., human frataxin), as described above. The nucleic acid sequence may also encode an amino acid sequence comprising an amino acid sequence having at least 85%, at least 90%, at least 95% or at least 99% sequence identity to SEQ ID NO: 1 or SEQ ID NO: 2.

The variants referred to in this disclosure optionally include conservatively substituted variants that apply to both amino acid and nucleic acid sequences. With respect to nucleic acid sequences, conservatively modified variants refer to those nucleic acids which encode identical or essentially identical amino acid sequences. Specifically, degenerate codon substitutions may be achieved by generating sequences in which the third position of one or more selected (or all) codons is substituted with mixed base and/or deoxyinosine residues. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are silent variations, which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

With regard to conservative substitution of amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a conservatively modified variant where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

The following groups each contain amino acids that are conservative substitutions for one another: 1) Alanine (A), Glycine (G); 2) Serine (S), Threonine (T); 3) Aspartic acid (D), Glutamic acid (E); 4) Asparagine (N), Glutamine (Q); 5) Cysteine (C), Methionine (M); 6) Arginine (R), Lysine (K), Histidine (H); 7) Isoleucine (1), Leucine (L), Valine (V); and 8) Phenylalanine (F), Tyrosine (Y), Tryptophan (W).

The term "derivative", as used herein, refers to amino acid sequences (polypeptides), which differ from the polypeptides specifically defined in the present disclosure by insertions, deletions, substitutions and modifications of amino acid residues that do not alter the activity of the original polypeptides. It should be appreciated that by the terms "insertion/s", "deletion/s" or "substitution/s", as used herein it is meant any addition, deletion or replacement, respectively, of amino acid residues to the polypeptides of between 1 to 50 amino acid residues, or between 1 to 10 amino acid residues. More particularly, insertion/s, deletion/s or substitution/s may be of any one of 1, 2, 3, 4, 5, 6, 7, 8, 9, or 10 amino acid residues. It should be noted that the insertion/s, deletion/s or substitution/s may occur in any position of the modified peptide, as well as in any of the N' or C' termini thereof.

By the term "derivative" it is also referred to homologues, variants and analogues thereof, as well as covalent modifications of a polypeptide. A derivative, a variant and an analogue of frataxin or a frataxin fragment described herein will have the same or substantially the same biological activity as its native form.

Frataxin Replacement Therapeutics Comprising CPP and TES

In some embodiments, the frataxin replacement therapeutic compound useful in the methods of the present disclosure is an FXN fusion protein comprising: full length or mature frataxin, or a fragment or a variant thereof; a CPP as described herein; and a target enhancing sequence (TES). The full length or mature frataxin may be, e.g., human frataxin, such as SEQ ID NO: 1 or SEQ ID NO: 2.

Without being bound by a specific theory, it is believed that CPP, when present in an FXN fusion protein, is capable of some level of interference with delivery of FXN to its proper subcellular localization, e.g., mitochondria, and, instead, facilitates delivery of FXN to the nucleus. The term "target enhancing sequence" (TES), as used herein, refers to an amino acid sequence that, when present in an FXN fusion protein comprising a CPP, prevents or attenuates said interference by the CPP with delivery of the FXN to the mitochondria. The term "target enhancing sequence" (TES), as used herein, also refers to an amino acid sequence that, when present in an FXN fusion protein comprising a CPP, facilitates or increases effective delivery of the FXN to cells, e.g., results in increased levels of the FXN in cells treated with the FXN fusion protein, and allows for, or promotes or increases, proper subcellular localization of the FXN to the mitochondria. Exemplary FXN fusion proteins comprising CPP and TES are described, e.g., in PCT/US2021/024534, filed on Mar. 26, 2021, the specific contents related to FXN fusion proteins of which are hereby incorporated herein by reference.

In some exemplary fusion proteins provided by the present disclosure, the TES comprises an amino acid sequence cleavable by an endogenous intracellular protease. In some embodiments, this TES is located immediately adjacent to the CPP, which, in turn, is located at the N-terminal end of the FXN. Upon entry of the fusion protein into the cell cytoplasm, the TES is cleaved by an intracellular nuclease. Without wishing to be bound by a specific theory, it is believed that cleavage of the TES facilitates removal of the CPP from the fusion protein and prevents or decreases any interference of the CPP with delivery of the FXN to the mitochondria, and/or prevents or decreases the extend to which the CPP may facilitate diffusion of the FXN across the plasma membrane and out of the cell.

In other exemplary embodiments, the TES comprises a nuclear export signal peptide (NES), which prevents CPP-facilitated delivery of the FXN fusion protein to the nucleus and, instead, facilitates delivery of the FXN fusion protein to the mitochondria.

In some embodiments, TES may comprise a protease-sensitive peptide, which may be also referred to herein as a "protease cleavage site". A protease-sensitive peptide or protease cleavage site refers to a specific amino acid motif within an amino acid sequence which is recognized and cleaved by a specific intracellular cytosolic protease. Nonlimiting examples of protease sensitive peptide or proteins that may be comprised in the TES include ubiquitin-like modifiers, such as ubiquitin, caspase cleavage domains, calpain cleavage domains, SUMO1, SUMO2, SUMO3, SUMO4, ISG15, Atg8, Atg12, and NEDD8.

Ubiquitin is highly conserved through eukaryote organisms, and the sequence of the human ortholog is:

```
                                         (SEQ ID NO. 23)
MQIFVKTLTGKTITLEVEPSDTIENVKAKIQDKEGIPPDQQRLIFAGKQL

EDGRTLSDYNIQKESTLHLVLRLRGG.
```

An exemplary caspase cleavage domain may comprise DEVD (SEQ ID NO. 24).

Nonlimiting examples of calpain cleavage domains are EPLFAERK (SEQ ID NO. 25) or LLVY (SEQ ID NO. 26).

Other exemplary protease cleavage sites may include any cleavage site described in Waugh, *Protein Expr. Purif.* 2011, 80(2):283-293, the entire contents of each of which are hereby incorporated herein by reference.

Exemplary proteases with specific protease cleavage sites may include ubiquitinase, caspase, calpain, enterokinase (light chain), enteropeptidase, prescission protease, human rhinovirus protease (HRV 3C), TEV (Tobacco Etch Virus) protease, TVMV (tobacco vein mottling virus) protease, Factor Xa protease, thrombin, and other proteases known to the person skilled in the art. Table 5 below includes some examples of amino acid sequences of protease cleavage sites and their respective proteases.

TABLE 5

Exemplary protease cleavage sites and corresponding proteases

| SEQ ID NO. | Protease | Cleavage Site Sequence |
|---|---|---|
| 27 | Enterokinase (light chain)/Enteropeptidase | DDDDK |
| 28 | PreScission Protease/human Rhinovirus protease (HRV 3C) | LEVLFQP |
| 29 | TEV protease | LEVLFGP |
| 30 | TEV protease | ENLYFQS |
| 31, 32 | TEV protease | Modified motifs based on the EXXYXQG (SEQ ID NO: 31) and EXXYXQS (SEQ ID NO: 32), where X may be any amino acid. |
| 33 | TVMV protease | ETVRFQS |
| 34 | Factor Xa protease | IEGR |
| 35 | Factor Xa protease | IDGR |
| 36 | Thrombin | LVPRS |
| 37 | Thrombin | LVPGS |

SUMO (Small Ubiquitin-like Modifier) proteins are a family of small proteins (about 100 amino acids in length and about 12 kDa in molecular weight) that are covalently attached to and detached from other proteins in cells to modify their function. The exact length and molecular weight vary between SUMO family members and depend on the organism from which the protein is derived. Examples of SUMO proteins are SUMO1, SUMO2, SUMO3 and SUMO4 with amino acid sequences as listed in Table 6 below.

TABLE 6

Amino acid sequences of SUMO proteins

| SEQ ID NO. | SUMO Protein | Amino Acid Sequence |
|---|---|---|
| 38 | SUMO1 | MSDQEAKPSTEDLGDKKEGEYIKLKVIGQDSSEIHFK VKMTTHLKKLKESYCQRQGVPMNSLRFLFEGQRIAD NHTPKELGMEEEDVIEVYQEQTGG |
| 39 | SUMO2 | MADEKPKEGVKTENNDHINLKVAGQDGSVVQFKIKR HTPLSKLMKAYCERQGLSMRQIRFRFDGQPINETDTP AQLEMEDEDTIDVFQQQTGGVY |
| 40 | SUMO3 | MSEEKPKEGVKTENDHINLKVAGQDGSVVQFKIKRH TPLSKLMKAYCERQGLSMRQIRFRFDGQPINETDTPA QLEMEDEDTIDVFQQQTGGVPESSLAGHSF |
| 41 | SUMO4 | MANEKPTEEVKTENNNHINLKVAGQDGSVVQFKIKR QTPLSKLMKAYCEPRGLSMKQIRFRFGGQPISGTDKP AQLEMEDEDTIDVFQQPTGGVY |

In some embodiments, TES comprised in an FXN fusion protein useful in the methods of the present disclosure may comprise a protease sensitive peptide or protein. In some examples, the TES may comprise a sequence described herein, e.g., any one of SEQ ID NOS. listed in Table 5 (SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37), or a sequence having at least 85%, e.g., at least 90% or at least 95% sequence identity with any one of SEQ ID NOS. listed in Table 5 (SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37). In some examples, the FXN fusion protein useful in the methods of the present disclosure may comprise a functional analogue, derivative or a fragment of the protein of interest of any one of SEQ ID NOS. listed in Table 5 (SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37).

In other embodiments, TES comprised in an FXN fusion protein useful in the methods of the present disclosure may comprise a ubiquitin-like modifier. In some examples, the TES may comprise a sequence described herein, e.g., any one of SEQ ID NOS. listed in Table 6 (SEQ ID NO: 38, SEQ ID NO: 39, SEQ ID NO: 40 or SEQ ID NO: 41), or a sequence having at least 85%, e.g., at least 86%, at least 87%, at least 88%, at least 89%, at least 90%, at least 91%, at least 92%, at least 93%, at least 94%, at least 95%, at least 96%, at least 97%, at least 98% or at least 99% sequence identity with any one of SEQ ID NOS. listed in Table 6 (SEQ ID NO: 38, SEQ ID NO: 39, SEQ ID NO: 40 or SEQ ID NO: 41). In some examples, an FXN fusion protein useful in the methods of the present disclosure may comprise a functional analogue, derivative or a fragment of the protein of interest of any one of SEQ ID NOS. listed in Table 6 (SEQ ID NO: 38, SEQ ID NO: 39, SEQ ID NO: 40 or SEQ ID NO: 41).

Amino acid sequences having at least 85% sequence identity to any of SEQ ID NOS. 27-37 or any of SEQ ID NOS. 38-41 may be found in one or more of the following databases: GenBank, Protein Data Bank (PDB), SwissProt, Protein Information Resource (PIR), or Protein Research Foundation (PRF).

In some examples, TES comprised in an FXN fusion protein useful in the methods of the present disclosure may comprise a nuclear export signal (NES). NES, when present in a protein, targets the protein for export from the cell nucleus into the cytoplasm. The export of the protein occurs through the nuclear pore complex via nuclear transport. Accordingly, in the context of the present disclosure, when a CPP present in an FXN fusion protein facilitates delivery of the FXN to the nucleus, NES counteracts said action by the CPP by facilitating export of the FXN from the nucleus into cytoplasm. In this manner, NES increases the likelihood that the protein of interest will be delivered to a non-nuclear organelle of interest, i.e., to mitochondria.

In some examples, NES may be a peptide comprising four hydrophobic residues which may not necessarily be in tandem. For example, NES may be a peptide comprising an amino acid sequence LXXXLXXLXL, where "L" is a hydrophobic residue (often leucine) and "X" is any amino acid other than leucine. Without wishing to be bound by a specific theory, it is believed that the spacing of the hydrophobic residues in an NES may be explained by examining known structures that contain an NES, as the critical residues usually lie in the same face of adjacent secondary structures within a protein, which allows them to interact with the exportin.

An FXN fusion protein useful in the methods of the present disclosure may comprise any NES known to one of ordinary skill in the art, including NES listed in the NESbase version 1.0, a database of nuclear export signals, the entire contents of which are hereby incorporated herein by reference. Table 7 lists certain exemplary NESs and their corresponding sequences.

TABLE 7

Exemplary NESs and corresponding sequences

| SEQ ID NO. | SUMO Protein | Amino Acid Sequence |
|---|---|---|
| 42 | NES1 | LALKLAGLDL |
| 43 | NES2 | LQKKLEELEL |
| 44 | NES3 | MQELSNILNL |
| 45 | NES4 | LPPLERLTL |
| 46 | NES5 | LCQAFSDVIL |
| 47 | NES6 | RTFDMHSLESSLIDIMR |
| 48 | NES7 | TNLEALQKKLEELELDE |
| 49 | NES8 | RSFEMTEFNQALEEIKG |

In some embodiments of the present disclosure, an FXN fusion protein may comprise NES comprising any sequence described herein, e.g., any one of SEQ ID NOS. listed in Table 7 (SEQ ID NO: 42, SEQ ID NO: 43, SEQ ID NO: 44, SEQ ID NO: 45, SEQ ID NO: 46, SEQ ID NO: 47, SEQ ID NO: 48 or SEQ ID NO: 49), or a sequence having at least 85%, e.g., at least 86%, at least 87%, at least 88%, at least 89%, at least 90%, at least 91%, at least 92%, at least 93%, at least 94%, at least 95%, at least 96%, at least 97%, at least 98% or at least 99% sequence identity with any one of SEQ ID NOS. listed in Table 7 (SEQ ID NO: 42, SEQ ID NO: 43, SEQ ID NO: 44, SEQ ID NO: 45, SEQ ID NO: 46, SEQ ID NO: 47, SEQ ID NO: 48 or SEQ ID NO: 49). In some examples, an FXN fusion protein useful in the methods of the present disclosure may comprise a functional analogue, derivative or a fragment of frataxin protein, e.g., SEQ ID NO: 1 or SEQ ID NO: 2, and any one of SEQ ID NOS. listed in Table 7 (SEQ ID NO: 42, SEQ ID NO: 43, SEQ ID NO: 44, SEQ ID NO: 45, SEQ ID NO: 46, SEQ ID NO: 47, SEQ ID NO: 48 or SEQ ID NO: 49).

Amino acid sequences having at least 85% sequence identity to any of SEQ ID NOS. 42-49 may be found in one or more of the following databases: GenBank, Protein Data Bank (PDB), SwissProt, Protein Information Resource (PIR), or Protein Research Foundation (PRF).

In one specific embodiment, the FXN fusion protein useful in the methods of the present disclosure comprises hFXN, e.g., SEQ ID NO: 2; HIV-TAT as the CPP, e.g., SEQ ID NO: 3 or SEQ ID NO: 4; and TES. In one further embodiment, the TES may a protease sensitive peptide or a protein, e.g., ubiquitin (e.g., SEQ ID NO: 23), caspase domain (e.g., SEQ ID NO: 24), a calpain cleavage domain (e.g., SEQ ID NO: 25 or SEQ ID NO: 26), or SUMO 1 (e.g., SEQ ID NO: 38). In another further embodiment, the TES may be an NES, e.g., NES1 (SEQ ID NO: 42) or NES2 (SEQ ID NO: 43).

In an embodiment of the disclosure a fusion protein provided herein may comprise a protein of interest to be delivered to a cell, a cell penetrating peptide (CPP) and a target enhancing sequence (TES). In some embodiments, the CPP is capable of interference with the delivery of the protein of interest to a cell and/or to a cellular organelle, and the TES prevents said interference by the CPP. In some examples, the protein of interest, CPP and TES may be directly fused to each other directly to form a single polypeptide chain. In other examples, the protein of interest, CPP and TES may be fused to each other via a spacer to form a single polypeptide chain.

In the FXN fusion protein useful in the methods of the present disclosure, the positions of the FXN, CPP and TES relative to teach other may vary. In exemplary embodiments in which TES comprises a protease-sensitive peptide, the FXN fusion protein may comprise, starting from the N-terminus, CPP, followed by TES, followed by the full-length hFXN (e.g., SEQ ID NO: 1) at the C-terminus. Alternatively, the FXN fusion protein may comprise, starting from the N-terminus, the full-length hFXN (e.g., SEQ ID NO: 1), followed by TES, followed by CPP at the C-terminus.

In other exemplary embodiments in which TES comprises NES, the FXN fusion protein may comprise, starting from the N-terminus, NES, followed by the full-length hFXN (e.g., SEQ ID NO: 1), followed by CPP. Alternatively, the FXN fusion protein may comprise, starting from the N-terminus, NES, followed by CPP, followed by the full-length hFXN (e.g., SEQ ID NO: 1). Alternatively, the FXN fusion protein may comprise, starting from the N-terminus, CPP, followed by the full-length hFXN (e.g., SEQ ID NO: 1), followed by NES. Alternatively, the FXN fusion protein may comprise, starting the from N-terminus, CPP, followed by NES, followed by the full-length hFXN (e.g., SEQ ID NO: 1).

In some embodiments, in an FXN fusion protein useful in the methods of the present disclosure, the CPP, TES and the frataxin protein, e.g., hFXN, such as SEQ ID NO: 1, may be fused to each other directly to form a single polypeptide chain. As used herein, the term "directly" means that there are no interfering amino acids between the C-terminal amino acid of the first domain and the N-terminal amino acid of the second domain that are directly fused to each other. That is, the (first or last) amino acid at the terminal end (N or C-terminal end) of the first domain may fused to the (first or last) amino acid at the terminal end (N or C-terminal end) of the second domain, forming a single polypeptide. In other words, in this embodiment, the last amino acid of the C-terminal end of a first domain is linked directly by a covalent bond to the first amino acid of the N-terminal end of the second domain, or the first amino acid of the N-terminal end of the first domain is directly linked by a covalent bond to the last amino acid of the C-terminal end of to form a single polypeptide.

In other examples, in an FXN fusion protein useful in the methods of the present disclosure, the CPP, TES and the frataxin protein, e.g., hFXN, such as SEQ ID NO: 1, may be fused together via a linker to form a single polypeptide chain. Linkers that may be comprised in FXN fusion proteins useful in the methods of the present disclosure are described herein, e.g., in Table 3.

Exemplary FXN fusion proteins comprising TES that are useful in the methods of the present disclosure and their corresponding sequences are listed in Table 8 below.

TABLE 8

Exemplary FXN fusion proteins comprising TES

| SEQ ID NO. | Fusion Protein | Sequence |
|---|---|---|
| 50 | TAT-SUMO1-hFXN | MYGRKKRRQRRRGGMSDQEAKPSTEDLGDKKEGEYIKLKVI GQDSSEIHFKVKMTTHLKKLKESYCQRQGVPMNSLRFLFEGQ RIADNHTPKELGMEEEDVIEVYQEQTGGMWTLGRRAVAGLL ASPSPAQAQTLTRVPRPAELAPLCGRRGLRTDIDATCTPRRASS NQRGLNQIWNVKKQSVYLMNLRKSGTLGHPGSLDETTYERL AEETLDSLAEFFEDLADKPYTFEDYDVSFGSGVLTVKLGGDLG TYVINKQTPNKQIWLSSPSSGPKRYDWTGKNWVYSHDGVSLH ELLAAELTKALKTKLDLSSLAYSGKDA |
| 51 | TAT-SUMO-hFXN | MYGRKKRRQRRRGGSDSEVNQEAKPEVKPEVKPETHINLKVS DGSSEIFFKIKKTTPLRRLMEAFAKRQGKEMDSLRFLYDGIRIQ ADQTPEDLDMEDNDIIEAHREQIGGMWTLGRRAVAGLLASPS PAQAQTLTRVPRPAELAPLCGRRGLRTDIDATCTPRRASSNQR GLNQIWNVKKQSVYLMNLRKSGTLGHPGSLDETTYERLAEET LDSLAEFFEDLADKPYTFEDYDVSFGSGVLTVKLGGDLGTYVI NKQTPNKQIWLSSPSSGPKRYDWTGKNWVYSHDGVSLHELL AAELTKALKTKLDLSSLAYSGKDA |
| 52 | TAT-Ubiquitin-hFXN | MYGRKKRRQRRRGGMQIFVKTLTGKTITLEVEPSDTIENVKA KIQDKEGIPPDQQRLIFAGKQLEDGRTLSDYNIQKESTLHLVLR LRGGMWTLGRRAVAGLLASPSPAQAQTLTRVPRPAELAPLCG RRGLRTDIDATCTPRRASSNQRGLNQIWNVKKQSVYLMNLRK SGTLGHPGSLDETTYERLAEETLDSLAEFFEDLADKPYTFEDY DVSFGSGVLTVKLGGDLGTYVINKQTPNKQIWLSSPSSGPKRY DWTGKNWVYSHDGVSLHELLAAELTKALKTKLDLSSLAYSG KDA |
| 53 | TAT-DEVD-hFXN | MYGRKKRRQRRRGGDEVDMWTLGRRAVAGLLASPSPAQAQ TLTRVPRPAELAPLCGRRGLRTDIDATCTPRRASSNQRGLNQI WNVKKQSVYLMNLRKSGTLGHPGSLDETTYERLAEETLDSLA EFFEDLADKPYTFEDYDVSFGSGVLTVKLGGDLGTYVINKQTP NKQIWLSSPSSGPKRYDWTGKNWVYSHDGVSLHELLAAELT KALKTKLDLSSLAYSGKDA |
| 54 | TAT-EPLFAERK-hFXN | MYGRKKRRQRRRGGEPLFAERKMWTLGRRAVAGLLASPSPA QAQTLTRVPRPAELAPLCGRRGLRTDIDATCTPRRASSNQRGL NQIWNVKKQSVYLMNLRKSGTLGHPGSLDETTYERLAEETLD SLAEFFEDLADKPYTFEDYDVSFGSGVLTVKLGGDLGTYVINK QTPNKQIWLSSPSSGPKRYDWTGKNWVYSHDGVSLHELLAAE LTKALKTKLDLSSLAYSGKDA |
| 55 | TAT-LLVY-hFXN | MYGRKKRRQRRRGGLLVYMWTLGRRAVAGLLASPSPAQAQ TLTRVPRPAELAPLCGRRGLRTDIDATCTPRRASSNQRGLNQI WNVKKQSVYLMNLRKSGTLGHPGSLDETTYERLAEETLDSLA EFFEDLADKPYTFEDYDVSFGSGVLTVKLGGDLGTYVINKQTP NKQIWLSSPSSGPKRYDWTGKNWVYSHDGVSLHELLAAELT KALKTKLDLSSLAYSGKDA |
| 56 | TAT-hFXN-NES1 | MYGRKKRRQRRRGGMWTLGRRAVAGLLASPSPAQAQTLTR VPRPAELAPLCGRRGLRTDIDATCTPRRASSNQRGLNQIWNVK KQSVYLMNLRKSGTLGHPGSLDETTYERLAEETLDSLAEFFED LADKPYTFEDYDVSFGSGVLTVKLGGDLGTYVINKQTPNKQI WLSSPSSGPKRYDWTGKNWVYSHDGVSLHELLAAELTKALK TKLDLSSLAYSGKDALALKLAGLDL |
| 57 | TAT-hFXN-NES2 | MYGRKKRRQRRRGGMWTLGRRAVAGLLASPSPAQAQTLTR VPRPAELAPLCGRRGLRTDIDATCTPRRASSNQRGLNQIWNVK KQSVYLMNLRKSGTLGHPGSLDETTYERLAEETLDSLAEFFED LADKPYTFEDYDVSFGSGVLTVKLGGDLGTYVINKQTPNKQI WLSSPSSGPKRYDWTGKNWVYSHDGVSLHELLAAELTKALK TKLDLSSLAYSGKDALQKKLEELEL |

In some embodiments, the FXN fusion protein useful in the methods of the present disclosure comprises or consists of any one sequence as listed in Table 8, i.e., any of SEQ ID NOS: 50-57 (e.g., SEQ ID NO: 50, SEQ ID NO: 51, SEQ ID NO: 52, SEQ ID NO: 53, SEQ ID NO: 54, SEQ ID NO: 55, SEQ ID NO: 56 or SEQ ID NO: 57). In some embodiments, the FXN fusion protein useful in the methods of the present disclosure comprises or consists of an amino acid sequence having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one sequence listed in Table 8, i.e., any of SEQ ID NOS: 50-57 (e.g., SEQ ID NO: 50, SEQ ID NO: 51, SEQ ID NO: 52, SEQ ID NO: 53, SEQ ID NO: 54, SEQ ID NO: 55, SEQ ID NO: 56 or SEQ ID NO: 57). In some embodiments, the FXN fusion protein useful in the methods of the present disclosure may comprise or consist of a functional analogue, derivative or a fragment of any one sequence listed in Table 8, i.e., any of SEQ ID NOS: 50-57 (e.g., SEQ ID NO: 50, SEQ ID NO: 51, SEQ ID NO: 52, SEQ ID NO: 53, SEQ ID NO: 54, SEQ ID NO: 55, SEQ ID NO: 56 or SEQ ID NO: 57).

In one embodiment, the FXN fusion protein useful in the methods of the present disclosure comprises or consists of TAT-SUMO1-hFXN having an amino acid sequence as set forth in SEQ ID NO: 50. In one embodiment, the FXN fusion protein comprises or consists of TAT-SUMO-hFXN having an amino acid sequence as set forth in SEQ ID NO: 51. In one embodiment, the FXN fusion protein useful in the methods of the present disclosure comprises or consists of TAT-Ubiquitin-hFXN having an amino acid sequence as set forth in SEQ ID NO: 52. In one embodiments, the FXN fusion protein useful in the methods of the present disclosure comprises or consists of TAT-DEVD-hFXN having an amino acid sequence as set forth in SEQ ID NO: 53. In one embodiment, the FXN fusion protein useful in the methods of the present disclosure comprises or consists of TAT-EPLFAERK-hFXN having an amino acid sequence as set forth in SEQ ID NO: 54. In one embodiment, the FXN fusion protein useful in the methods of the present disclosure comprises or consists of TAT-LLVY-hFXN having an amino acid sequence as set forth in SEQ ID NO: 55. In one embodiment, the FXN fusion protein useful in the methods of the present disclosure comprises or consists of TAT-hFXN-NES1 having an amino acid sequence as set forth in SEQ ID NO: 56. In one embodiment, the FXN fusion protein useful in the methods of the present disclosure comprises or consists of TAT-hFXN-NES2 having an amino acid sequence as set forth in SEQ ID NO: 57.

In some embodiments, the FXN fusion protein useful in the methods of the present disclosure comprises: 1) an amino acid sequence having at least 85%, at least 90%, at least 95%, or at least 99% sequence identity to full-length hFXN (SEQ ID NO: 1); 2) any CPP as described herein; and 3) any TES as described herein.

In some embodiments, the FXN fusion protein useful in the methods of the present disclosure comprises: 1) an amino acid sequence having at least 85%, at least 90%, at least 95%, or at least 99% sequence identity to full-length hFXN (SEQ ID NO: 1); 2) an amino acid sequence having at least 85%, at least 90%, at least 95% or at least 99% to TAT-HIV (SEQ ID NO: 3 or SEQ ID NO: 4); and 3) any TES as described herein.

For example, the FXN fusion protein useful in the methods of the present disclosure may comprise 1) an amino acid sequence having at least 85%, at least 90%, at least 95%, or at least 99% sequence identity to full-length hFXN (SEQ ID NO: 1); 2) an amino acid sequence having at least 85%, at least 90%, at least 95% or at least 99% to TAT-HIV (SEQ ID NO: 3 or SEQ ID NO: 4); and 3) an amino acid sequence having at least 85%, at least 90%, at least 95% or at least 99% to Ubiquitin (SEQ ID NO: 23).

For example, the FXN fusion protein useful in the methods of the present disclosure may comprise 1) an amino acid sequence having at least 85%, at least 90%, at least 95%, or at least 99% sequence identity to full-length hFXN (SEQ ID NO: 1); 2) an amino acid sequence having at least 85%, at least 90%, at least 95% or at least 99% to TAT-HIV (SEQ ID NO: 3 or SEQ ID NO: 4); and 3) an amino acid sequence having at least 85%, at least 90%, at least 95% or at least 99% to a calpain cleavage domain of SEQ ID NO: 25 or SEQ ID NO: 26.

For example, the FXN fusion protein useful in the methods of the present disclosure may comprise 1) an amino acid sequence having at least 85%, at least 90%, at least 95%, or at least 99% sequence identity to full-length hFXN (SEQ ID NO: 1); 2) an amino acid sequence having at least 85%, at least 90%, at least 95% or at least 99% to TAT-HIV (SEQ ID NO: 3 or SEQ ID NO: 4); and 3) an amino acid sequence having at least 85%, at least 90%, at least 95% or at least 99% to an NES of any one of SEQ ID NOS. 42-49, e.g., SEQ ID NO: 42, SEQ ID NO: 43, SEQ ID NO: 44, SEQ ID NO: 45, SEQ ID NO: 46, SEQ ID NO: 47, SEQ ID NO: 48 or SEQ ID NO: 49.

For example, the FXN fusion protein useful in the methods of the present disclosure may comprise 1) an amino acid sequence having at least 85%, at least 90%, at least 95%, or at least 99% sequence identity to full-length hFXN (SEQ ID NO: 1); 2) an amino acid sequence having at least 85%, at least 90%, at least 95% or at least 99% to TAT-HIV (SEQ ID NO: 3 or SEQ ID NO: 4); and 3) an amino acid sequence having at least 85%, at least 90%, at least 95% or at least 99% to any one of SEQ ID NO 24, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40 or SEQ ID NO: 41.

In some embodiments, an FXN fusion protein useful in the methods of the present disclosure may also include a post-translational modification characteristic of eukaryotic cells, e.g., mammalian cells, e.g., human cells. In some embodiments, the fusion protein may comprise one or more (e.g., 2, 3, 4, 5, 6, 7, 8, 9, 10, or more) post-translational modifications, such as glycosylation, phosphorylation, acetylation, or combinations thereof. In some embodiments, glycosylation may include the addition of a glycosyl group to arginine, asparagine, cysteine, hydroxylysine, serine, threonine, tyrosine, or tryptophan. The glycosylation may comprise, e.g., O-linked glycosylation or N-linked glycosylation. Levels of glycosylation of a fusion protein of the disclosure may be assessed in vitro using SDS-PAGE gels and a Western Blot using a modification of Periodic acid-Schiff (PAS) methods. Cellular localization of a fusion protein that may comprise glycosylation may be accomplished by utilizing lectin fluorescent conjugates known in the art. Phosphorylation that may be present in a fusion protein of the present disclosure may be assessed by Western blot using phospho-specific antibodies.

Post-translation modifications that may be present in an FXN fusion protein useful in the methods of the present disclosure may also include conjugation to a hydrophobic group (e.g., myristoylation, palmitoylation, isoprenylation, prenylation, or glypiation), conjugation to a cofactor (e.g., lipoylation, flavin moiety (e.g., FMN or FAD), heme C attachment, phosphopantetheinylation, or retinylidene Schiff base formation), diphthamide formation, ethanolamine phosphoglycerol attachment, hypusine formation, acylation (e.g. O-acylation, N-acylation, or S-acylation), formylation, acetylation, alkylation (e.g., methylation or ethylation), amidation, butyrylation, gamma-carboxylation, malonylation, hydroxylation, iodination, nucleotide addition such as ADP-ribosylation, oxidation, phosphate ester (O-linked) or phosphoramidate (N-linked) formation, (e.g., phosphorylation or adenylylation), propionylation, pyroglutamate formation, S-glutathionylation, S-nitrosylation, succinylation, sulfation, ISGylation, SUMOylation, ubiquitination, neddylation, or a chemical modification of an amino acid (e.g., citrullination, deamidation, eliminylation, or carbamylation), formation of a disulfide bridge, racemization (e.g., of proline, serine, alanine, or methionine).

II. Compositions and Modes of Administration

In accordance with methods of the present disclosure, a frataxin replacement therapeutic compound may be administered through delivery of a frataxin polypeptide (e.g., a fusion protein comprising a frataxin polypeptide) or through delivery of a nucleic acid encoding a frataxin polypeptide.

A frataxin replacement therapeutic compound may be administered as a part of a pharmaceutical composition comprising a frataxin replacement therapeutic compound and a pharmaceutically acceptable diluent, carrier, additive and/or excipient.

Preparation of pharmaceutical compositions is discussed in, for example, in Hoover, John E. (eds.) Remington's Pharmaceutical Sciences, Mack Publishing Co., Easton, Pa. $18^{th}$ edition (1990), and in Liberman, H. A. and Lachman, L. (eds.) Pharmaceutical Dosage Forms, Marcel Decker, New York, N.Y. (1989), the entire contents of each of which are hereby incorporated herein by reference.

A pharmaceutical composition may be delivered to cells in vitro, for example by contacting the cells with the pharmaceutical composition. Alternatively, for delivery in vivo, the pharmaceutical composition in accordance with methods of the present disclosure may be administered orally, parenterally, by inhalation spray, rectally, intradermally, transdermally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques.

Injectable pharmaceutical compositions, for example, sterile injectable aqueous or oleaginous suspensions, may be formulated according to the techniques known in the art using suitable dispersing or wetting agents and suspending agents. The sterile injectable pharmaceutical composition may also be a sterile injectable solution or a suspension in a nontoxic parenterally acceptable diluent or solvent, for example, 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids, such as oleic acid, are useful in the preparation of injectables. Dimethyl acetamide, surfactants including ionic and non-ionic detergents, and polyethylene glycols can be used. Mixtures of solvents and wetting agents such as those discussed above are also useful.

Pharmaceutical compositions for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. A frataxin replacement therapeutic compound to be administered in accordance with methods of the present disclosure may be formulated in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration may include pharmaceutically acceptable emulsions, solutions, suspensions, syrups, and elixirs containing inert diluents commonly used in the art, such as water. Such pharmaceutical compositions may also comprise adjuvants, such as wetting agents, emulsifying and suspending agents, and sweetening, flavoring, and perfuming agents.

Solid dosage forms for oral administration may include capsules, tablets, pills, powders, and granules. In such solid dosage forms, a frataxin replacement therapeutic compound may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as can be provided in a dispersion of active compound in hydroxypropylmethyl cellulose. In the case of capsules, tablets, and pills, the dosage forms may also comprise buffering agents such as sodium citrate, or magnesium or calcium carbonate or bicarbonate. Tablets and pills may additionally be prepared with enteric coatings.

Suppositories for rectal administration of a frataxin replacement therapeutic compound may be prepared by mixing the frataxin replacement therapeutic compound with a suitable non-irritating excipient such as cocoa butter, synthetic mono-, di-, or triglycerides, fatty acids, or polyethylene glycols which are solid at ordinary temperatures but liquid at the rectal temperature, and which will therefore melt in the rectum and release the drug.

The frataxin replacement therapeutic compound may be administered in accordance with methods of the present disclosure by a variety of methods, including, for example, orally, enterally, mucosally, percutaneously, or parenterally. Parenteral administration is preferred, especially by intravenous, intramuscular, subcutaneous, intracutaneous, intraarticular, intrathecal, and intraperitoneal infusion or injection, including continuous infusions or intermittent infusions with pumps available to those skilled in the art. Alternatively, the fusion protein may be administered by means of micro-encapsulated preparations, for example based on liposomes.

In an embodiment, a frataxin replacement therapeutic compound may be prepared as part of a protein delivery system. A broad overview of protein delivery systems may be found, for example, in Banga, A. K. (2015) *Therapeutic Peptides and Proteins: Formulation, Processing, and Delivery Systems,* $3^{rd}$ ed., CRC Press, Taylor & Francis Group. Particulate systems include microspheres, microparticles, microcapsules, nanocapsules, nanospheres, and nanoparticles. Microcapsules may contain the therapeutic protein, such as frataxin, as a central core. In microspheres, the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm diameter and are administered subcutaneously or intramuscularly. See, for example, Kreuter, J. (1994) *Colloidal Drug Delivery Systems*, CRC Press, Taylor & Francis Group, New York, N.Y., pp. 219-342 (1994); and Tice & Tabibi (1992) *Treatise on Controlled Drug Delivery*, Chapter 7, A. Kydonieus, ed., CRC Press, Taylor & Francis Group, New York, N.Y., pp. 315-339.

A frataxin replacement therapeutic compound may also be administered in accordance with methods of the present disclosure through an expression vector for producing a frataxin replacement therapeutic compound in a cell (such as a mammalian, bacterial or fungal cell). The expression vector may comprise a nucleic acid encoding a frataxin replacement therapeutic compound, e.g., a frataxin polypeptide or fusion protein comprising a frataxin polypeptide, as described herein. By way of example, the expression vector may be a retroviral vector, a DNA vector, a plasmid, an RNA vector, an adenoviral vector, an adenovirus associated vector, a lentiviral vector, a phagemid, a baculovirus, or any combination thereof.

Vectors may enable the integration of DNA fragments or nucleic acid sequences into the genome of the host or enable expression of genetic elements that are not integrated. Vectors are typically self-replicating DNA or RNA constructs containing the desired nucleic acid sequences, and operably linked genetic control elements that are recognized in a suitable host cell and effect the translation of the desired spacers. Generally, the genetic control elements can include a prokaryotic promoter system or a eukaryotic promoter expression control system. Such system typically includes a transcriptional promoter and transcriptional enhancers to elevate the level of RNA expression. Vectors usually contain an origin of replication that allows the vector to replicate independently of the host cell. Accordingly, the control and regulatory elements may include promoters, terminators and other expression control elements. Such regulatory elements are described in the art and known to the skilled artisan. For instance, any of a wide variety of expression control sequences that control the expression of a DNA sequence when operatively linked to it may be used in these vectors to express DNA sequences encoding any desired fusion protein as described herein. The phrase "operatively-linked" is intended to mean attached in a manner which allows for transgene transcription. The term "encoding" is intended to mean that the subject nucleic acid may be transcribed and translated into either the desired polypeptide or the subject protein in an appropriate expression system, e.g., when the subject nucleic acid is linked to appropriate control sequences such as promoter and enhancer elements in a suitable vector (e.g., an expression vector) and when the vector is introduced into an appropriate system or cell.

A vector may additionally include appropriate restriction sites, antibiotic resistance or other markers for selection of vector-containing cells. Plasmids are the most commonly used form of vector but other forms of vectors which serve an equivalent function, and which are, or become, known in the art are suitable for use herein.

A frataxin replacement therapeutic compound may also be delivered in accordance with methods of the present disclosure by viral gene replacement, which may utilize retroviral, lentiviral, and adeno-associated viral vectors, as well as adenoviruses.

A frataxin replacement therapeutic compound comprising a nucleic acid encoding a polypeptide comprising frataxin or a fragment or a variant thereof, may also be delivered in accordance with methods of the present disclosure using a non-viral delivery system. Non-limiting examples of non-viral delivery systems include, e.g., lipid-based DNA vectors, and polymeric DNA vectors, as described in Yin et al., Nature Reviews Genetics 2014, 15, 541-555, the entire contents of which are incorporated herein by reference.

It should be considered that delivery or administration of a frataxin compound may also be achieved by upregulation of the endogenous FXN gene, resulting in increased levels of endogenous frataxin in the cell of a subject. Upregulation of an FXN gene may be triggered through a compound, a drug, or any agent that affects the mitochondrial pathway.

III. Methods of Treating a Myelin Associated Disease

The present disclosure provides methods for treating a myelin associated disease. The methods comprise administering to a subject in need thereof an effective amount of a frataxin replacement therapeutic compound, e.g., an exemplary TAT-hFXN fusion protein, such that the myelin associated disease in the subject is treated.

The term "myelin associated disease", as used herein, refers to any disease that is characterized by the presence of an abnormal, e.g., defective or damaged, myelin in a subject. Myelin is a lipid rich substance that forms a white insulating sheath around axons of neurons. Myelin is deposited in layers around axons by oligodendrocytes in the central nervous system (CNS) and by Schwann cells in the peripheral nervous system (PNS) forming a myelin sheath. Myelin is essential for normal motor function (e.g., movement such as walking), sensory function (e.g., hearing, seeing or feeling the sensation of pain) and cognition (e.g., acquiring and recalling knowledge). An abnormal, e.g., defective or damaged, myelin is characterized by an abnormality or deficiency in the normal biological function of myelin and may be associated with, e.g., abnormal motor and/or sensory function, and/or abnormal cognition in a subject with a myelin associated disease. Presence of an abnormal myelin in a subject may be determined by using any method known in the art for assessing myelination, e.g., imaging techniques such as MRI and/or CT scans to identify abnormalities and lesions in the brain of a subject. In some embodiments, the term "myelin associated disease" does not encompass Friedreich's Ataxia (FRDA). In some embodiments, the term "myelin associated disease" does not encompass Leigh Syndrome, French Canadian Type (LSFC). In some embodiments, the term "myelin associated disease" does not encompass both Friedreich's Ataxia (FRDA) and Leigh Syndrome, French Canadian Type (LSFC). In some embodiments, the term "myelin associated disease" comprises a dysmyelination disease. In some embodiments, the term "myelin associated disease" is a dysmyelination disease. A "dysmyelination disease", as used herein, refers to a disease characterized by the presence of a malformed and/or defective myelin in a nervous system of a subject. The term "dysmyelination", as used herein, refers to malformed and/or defective myelin, and is distinct from the term "demyelination", which refers to destruction of previously normal myelin. Dysmyelination disorders often arise from hereditary mutations that affect the synthesis and formation of myelin.

Non-limiting examples of dysmelination diseases comprise leukodystrophies. Leukodystrophies are a group of rare, progressive, metabolic, genetic diseases that affect the brain, spinal cord and often the peripheral nerves. Each type of leukodystrophy is caused by a specific gene abnormality that leads to abnormal development of the white matter (myelin sheath) of the brain. Exemplary leukodystrophies that may be treated by the methods of the present disclosure and the associated genes and characteristics are listed in Table 9 below.

TABLE 9

Exemplary leukodystrophies and associated characteristics

| No. | Leukodystrophy Disease Name | Associated Gene/Protein | Characteristics/Symptoms |
|---|---|---|---|
| 1 | Adult-onset autosomal dominant leukodystrophy (ADLD) | LMNB1 gene Encodes the nuclear lamina protein lamin B1. | Symptoms begin in the fourth to fifth decade with autonomic dysfunction including bowel and bladder dysfunction and orthostatic hypotension with lightheadedness. This is followed by slowly progressive motor and balance difficulties. The MRI of the brain shows extensive white matter involvement with relative sparing of the periventricular white matter. The spinal cord develops atrophy which may precede the motor difficulties. |
| 2 | Cerebral Autosomal Dominant Arteriopathy Subcortical Infarcts Leukoencephalopathy (CADASIL) | NOTCH3 receptor gene Encodes NOTCH 3 protein. | Presentation of the disease includes migraine headaches and multiple strokes in adults, even young adults, often without cardiovascular risk factors. CADASIL often progresses to cause cognitive impairment and dementia. The symptoms of CADASIL result from damage of various small blood vessels, especially those within the brain. The age of onset, severity, specific symptoms and disease progression varies greatly from one person to another, even among members of the same family. |
| 3 | Cerebral Autosomal Recessive Arteriopathy Subcortical Infarcts Leukoencephalopathy (CARASIL) | HTRA1 gene Encodes cerebral small-vessel disease protein HTRA1. This protein controls the amount of TGF-B1 via cleavage of proTGF-B1b. | Individuals with CARASIL are at risk of developing multiple strokes, even if they do not have cardiovascular risk factors. The symptoms of CARASIL result from damage to various small blood vessels, especially those within the brain. Individuals with CARASIL may develop a variety of symptoms relating to white matter involvement or leukoaraiosis (changes in deep white matter in the brain, which are observed on MRI). Such symptoms include an increasing muscle tone (spasticity), pyramidal signs, and pseudo bulbar palsy beginning between 20 and 30 years of age. Pseudo bulbar palsy is a group of neurologic symptoms including difficulties with chewing, swallowing and speech. Eventually, cognitive impairment and dementia may result. About half of cases have a stroke-like episode. The age of onset is 20 to 50 years old. |
| 4 | Childhood Ataxia with Cerebral Hypomyelination (CACH), also known as Vanishing White Matter Disease (VWMD) | Eukaryotic initiation factor 2B (eIF2B) gene. Encodes the eIF2B protein, which is highly conserved, ubiquitously expressed and plays an essential role in the initiation of protein synthesis by catalyzing the GDP-GTP exchange on eIF2 to enable binding of methionyl-transfer-RNA to the ribosome. | This disease is an autosomal recessive leukodystrophy that is characterized by progressive deterioration in motor function and speech during the first five years of life. Clinical symptoms typically begin in the first few years of life, following a normal to mildly delayed early development. Common presenting symptoms include ataxia and seizures. The course is chronic and progressive with episodic decline following fever, head trauma, or periods of fright. Patients usually survive only a few years past the clinical onset, though the course is variable even among patients with mutations in the same eIF2B subunit. In the rare reports of adult-onset VWMD, the typical |

TABLE 9-continued

| Exemplary leukodystrophies and associated characteristics | | | |
|---|---|---|---|
| No. | Leukodystrophy Disease Name | Associated Gene/Protein | Characteristics/Symptoms |
| | | | presentation consists of cognitive deterioration, pseudo bulbar palsy and progressive spastic paraparesis. |
| 5 | L-2-hydroxyglutaric aciduria | L2HGDH gene Encodes L-2 hydroxyglutarate dehydrogenase, which is an FAD-linked mitochondrial enzyme that converts L-2 hydroxyglutarate to a-ketoglutarate. | Biochemically, this disease presents with significantly elevated levels of L-2-hydroxyglutaric acid in the urine and CSF. Plasma amino acids reveal elevated lysine. Clinically, this disease presents with variable degrees of psychomotor and speech delay followed by a slowly progressive neurodegenerative disorder with cognitive decline. The MRI demonstrate a complex but characteristic pattern of abnormal signal intensity in the subcortical white matter bilaterally with frontal predominance and involvement of the globus pallidus, caudate and putamen bilaterally as well as the dentate nucleus. |
| 6 | Megalencephalic leukoencephalopathy with subcortical cysts | HEPACAM gene Encodes GlialCAM protein, which is found in liver and glial cells. In glial cells, GlialCAM attaches to other GlialCAM proteins or to other MLC1 and ClC-2 proteins. GlialCAM ensures that these proteins are transported to junctions that connect neighboring glial cells. The function of GlialCAM at the cell junction is unclear. | This is an autosomal recessive condition which initially presents with macrocephaly (enlarged head size). Mild motor delay is followed by gradual motor deterioration with ataxia and spasticity. Cognitive abilities are relatively spared but seizures may occur in this classical form. Recessive MLC1 mutations are observed in 80% of patients with MLC. Other patients with the classical, deteriorating phenotype have two mutations in the HEPACAM gene. An improving phenotype has been described in patients with only one mutation in HEPACAM. Most parents with a single mutation had macrocephaly, indicating dominant inheritance. In some families with dominant HEPACAM mutations, the clinical picture and magnetic resonance imaging normalized, indicating that HEPACAM mutations can cause benign familial macrocephaly. In other families with dominant HEPACAM mutations, patients had macrocephaly and intellectual disability with or without autism. Diffuse white matter abnormalities on MRI are accompanied by anterior temporal cysts. |
| 7 | Multiple sulfatase deficiency (MSD) | SUMF1 gene Encodes formylglycine-generating enzyme (FGE), which modifies sulfatases to convert cysteine into C-alpha-formylglycine. | In this disease all of the known sulfatase enzymes (thought to be seven in number) are deficient or inoperative due to mutations in the SUMF1 gene. Major symptoms include mildly coarsened facial features, deafness, and an enlarged liver and spleen (hepatosplenomegaly). Abnormalities of the skeleton may occur, such as curvature of the spine (lumbar kyphosis) and the breast bone. The skin is usually dry and scaly (ichthyosis). Before symptoms are noticeable, children with this disorder usually develop more slowly than normal. They may not learn to walk or speak as quickly as other children. |
| 8 | Pelizaeus-Merzbacher disease (PMD), also known as X-linked spastic paraplegia | PLP1 gene Encodes proteolipid protein 1 (PLP1). | Symptoms may include the impaired ability to coordinate movement (ataxia), involuntary muscle spasms (spasticity) that result in slow, stiff movements of the legs, delays in reaching developmental milestones, loss of motor abilities, and the progressive deterioration of intellectual function. |

TABLE 9-continued

| Exemplary leukodystrophies and associated characteristics | | | |
|---|---|---|---|
| No. | Leukodystrophy Disease Name | Associated Gene/Protein | Characteristics/Symptoms |
| 9 | Pol III-Related Leukodystrophies | POLR3A gene or POLR3B gene. Encode subunits of RNA Polymerase III. | The Pol III-related leukodystrophies comprise a group of 5 overlapping clinically defined hypomyelinating leukodystrophies including: hypomyelination, hypodontia, hypogonadotropic hypogonadism (4H syndrome); Ataxia, delayed dentition, and hypomyelination (ADDH); Tremor-ataxia with central hypomyelination (TACH); Leukodystrophy with oligodontia (LO); and Hypomyelination with cerebellar atrophy and hypoplasia of the corpus callosum (HCAHC). These conditions present with varying combinations of motor dysfunction, abnormal teeth and hypogonadotropic hypogonadism. The MRI scan of the brain demonstrates hypomyelination. |
| 10 | Salla Disease | SLC17A5 gene Encodes sialin | The disease is characterized by accumulation of free sialic acid (N-acetylneuraminic acid) in lysosomes. Most children present between 3 and 9 months of age with hypotonia, ataxia, delayed motor milestones, and transient nystagmus. Cognitive delay and slow motor decline occurs after the second to third decade. Peripheral neuropathy may be present and contribute to motor disability. |
| 11 | X-linked adrenoleukodystrophy (ALD) | ABCD1 gene Encodes adrenoleukodystrophy protein (ALDP), which transports very long-chain fatty acids (VLCFAs) into peroxisomes. | ALD is a progressive disease characterized by an accumulation of VLCFAs. The disease is characterized by cognitive decline and progressive neurologic deficits which lead to a vegetative state, blindness, seizures and death often within 3 yrs. |
| 12 | Zellweger syndrome spectrum disorders, also known as peroxisomal biogenesis disorders (PBDs) | PEX genes Encode proteins involved in peroxisome assembly and proliferation. | The disorders are characterized by a deficiency or absence of peroxisomes in the cells of the liver, kidneys, and brain and lead to accumulation of waste products, including very long chain fatty acids (VLCFA). PBDs are inherited as autosomal recessive disorders and have two clinically distinct subtypes: the Zellweger syndrome spectrum (ZSS) disorders and rhizomelic chondrodysplasia punctata (RCDP) type 1. A range of symptoms are seen including developmental delay, sensorineural hearing loss, visual abnormalities, adrenal insufficiency and liver dysfunction. |

In some embodiments, the myelin associated disease may be a Vanishing White Matter Disease (VWMD) or X-Linked adrenoleukodystrophy (ALD). In some embodiments, the myelin associated disease comprises or consists of Vanishing White Matter Disease (VWMD). In some embodiments, the myelin associated disease comprises or consists of X-Linked adrenoleukodystrophy (ALD). In some embodiments, the myelin associated disease comprises of consists of ADLD. In some embodiments, the myelin associated disease comprises of consists of CADASIL. In some embodiments, the myelin associated disease comprises of consists of CARASIL. In some embodiments, the myelin associated disease comprises of consists of L-2-hydroxyglutaric aciduria. In some embodiments, the myelin associated disease comprises of consists of megalencephalic leukoencephalopathy with subcortical cysts. In some embodiments, the myelin associated disease comprises of consists of MSD. In some embodiments, the myelin associated disease comprises of consists of PMD. In some embodiments, the myelin associated disease comprises of consists of Pol III-related leukodystrophy. In some embodiments, the myelin associated disease comprises of consists of Salla Disease. In some embodiments, the myelin associated disease comprises of consists of PBD.

In some embodiments, the myelin associated disease comprises a demyelination disease. A "demyelination disease", as used herein, refers to, a disease characterized by destruction of previously normal myelin. A demyelination disease may also be referred to herein as a myelinoclastic disease. The term "demyelination", as used herein, refers to destruction of previously normal myelin and is distinct from the term "dysmyelination", which refers to malformed and/or defective myelin. The destruction of previously normal myelin in the demyelination diseases may result from damage to the myelin layer caused by a pathological process, e.g., inflammation, an autoimmune reaction, or exposure to endogenous or exogenous substances in a manner that causes damage to or destruction of myelin.

In some embodiments, a demyelination disease may be a central demyelination disease, i.e., characterized by demyelination in the central nervous system (CNS) that may, in some embodiments, involve damage to and/or destruction of myelin-supporting oligodendrocytes in the CNS. In some embodiments, a demyelination disease may be a peripheral demyelination disease, i.e., characterized by demyelination in the peripheral nervous system (PNS) that may, in some embodiments, involve damage to and/or destruction of myelin-supporting Schwann cells in the PNS. Certain myelin associated diseases may have characteristics of both a central demyelination disease, i.e., be characterized by demyelination in the CNS, and peripheral demyelination disease, i.e., be characterized by demyelination in the PNS.

In some embodiments, a demyelination disease may be a central demyelination disease. In further embodiments, a central demyelination disease may be an inflammatory or an immune central demyelination disease characterized by immune-mediated myelin damage or destruction. Such disease may occur against the background of an acute or chronic inflammatory process that may also comprise an autoimmune aspect. Non-limiting examples of an inflammatory or an immune central demyelination disease include multiple sclerosis (MS), myelinoclastic diffuse sclerosis (Schilder's Disease), optic neuritis, acute disseminated encephalomyelitis (ADEM), acute hemorrhagic leucoencephalitis (AHL), paraneoplastic encephalomyelitis, rheumatoid arthritis, systemic lupus erythematosus, Behçet's disease and Sjörgen disease.

In some embodiments, a central demyelination disease may be a granulomatous central demyelination disease, non-limiting examples of which include neurosarcoidosis, Wegener granulomatosis (granulomatosis with polyangiitis, GPA) and lymphomatoid granulomatosis.

In some embodiments, a central demyelination disease may be a central demyelination toxic or metabolic disease. Such diseases may be associated with exposure of the myelin to endogenous or exogenous substances in a manner that causes damage to or destruction of myelin. One exemplary central demyelination toxic or metabolic diseases is central pontine myelinolysis, which may occur after too rapid medical correction of sodium deficiency (hyponatremia). Without wishing to be bound by a specific theory, it is believed that the rapid rise in sodium concentration may be accompanied by the loss of water from the brain cells and may eventually lead to damage and destruction of myelin. It is also believed, without wishing to be bound by a specific theory, that the shift in water and brain molecules leads to the destruction of myelin. Other non-limiting examples of central demyelination toxic or metabolic diseases include disease associated with a vitamin B12 deficiency; carbon monoxide poisoning; exposure to radiation and posterior reversible encephalopathy syndrome (PRES).

In some embodiments, the demyelination disease may be a peripheral demyelination disease. A "peripheral demyelination disease", as used herein, refers to a disease characterized by demyelination in the peripheral nervous system (PNS) that may, in some embodiments, involve damage to and/or destruction of myelin-supporting Schwann cells in the PNS. Non-limiting examples of peripheral demyelination diseases include: Guillain-Barré Syndrome, chronic inflammatory demyelinating polyradiculoneuropathy (CIDP), paraproteinemic demyelinating neuropathy, progressive inflammatory neuropathy (PIN), Anti-Myelin Associated Glycoprotein (MAG) neuropathy, POEMS Syndrome, Charcot Marie Tooth Disease, and a copper deficiency associated disorder.

In some embodiments, the peripheral demyelination disease is Charcot-Marie-Tooth disease (CMT), also known as hereditary motor and sensory neuropathy (HMSN) or peroneal muscular atrophy. CMT is a heterogeneous disease and the mutations linked to it may occur in a number of different genes. Based on the affected gene, CMT is categorized into several types and subtypes.

In some embodiments, the CMT is CMT type 1A (CMT1A). CMT type 1A (CMT1A) is associated with the duplication of a large region on the short art of chromosome 17 that includes the gene PMP22. Duplication of PMP22 is the most common cause of CMT (70-80% of the cases). The PMP22 gene encodes peripheral myelin protein 22, which is mainly expressed in Schwann cells and functions in the formation and maintenance of compact myelin.

In some embodiments, the CMT is CMT type 2A2 (CMT2A2). CMT type 2A2 (CMT2A2) is associated with mutations in the gene MFN2 on chromosome 1, which encodes a mitochondrial membrane protein mitofusin 2 (MFN2). Mutated MFN2 causes the mitochondria to form large clusters, or clots, which are unable to travel down the axon towards the synapses, thus preventing the synapses from functioning.

CMT may also be caused by X-linked mutations, in which case it may be referred to as X-linked CMT (CMTX). For example, X-linked Charcot-Marie-Tooth Neuropathy, X-linked (CMTX) may associated with a mutation in the GJB1 gene encoding connexin 32, a gap junction protein expressed in Schwann cells. Accordingly, in some embodiments, the CMT is CMTX.

In some embodiments, the CMT is CMT type 1B (CMT1B). CMT type 1B (CMT1B) is associated with a mutation in the MPZ gene encoding myelin protein zero, which is produced by Schwann cells and is required for the proper formation and maintenance of myelin in the peripheral nerves. Mutations in the MPZ gene may also be associated with other forms of CMT, e.g., CMT type 21, type 2J, and dominant intermediate D. These forms of CMT, which often do not become evident until adulthood, affect axons.

In some embodiments, the CMT is CMT type 4 (CMT4). CMT type 4 (CMT4) is associated with mutations in a number of genes including, e.g., GDAP1 encoding ganglioside-induced differentiation-associated protein 1 and SURF1 encoding a cytochrome C oxidase assembly factor.

Other genes which, when mutated, that may be associated with CMT, are described, e.g., in Hoyle et al., "The genetics of Charcot-Marie-Tooth disease: current trends and future implications for diagnosis and management", *The Application of Clinical Genetics* 2015, 8:235-243, the entire contents of which are hereby incorporated herein by reference. Any such CMTs are encompassed by the present methods of the disclosure.

In some embodiments, the term "myelin associated disease" encompasses a myelin and mitochondria associated disease. The term "myelin and mitochondria associated disease", as used herein, refers to any disease that is characterized by the presence of an abnormal, e.g., defective or damaged, myelin in a subject and that is also characterized by a defect in the mitochondrial function in a subject. A defect in the mitochondrial function in a subject may be manifested by one or more of: increased concentration of lactic acid; i.e., lactic acidosis; increased lactate to pyruvate ratio; the presence of ragged red fibres in the cells of a subject (e.g., muscle, liver or skin cells); abnormal activity of proteins of the respiratory chains. Non-limiting examples of myelin and mitochondria associated diseases include diseases as described, e.g., in Table 10. In some embodiments, a myelin and mitochondria associated disease may be selected from the group consisting of mitochondrial encephalomyopathy, lactic acidosis, and stroke-like episodes (MELAS); myoclonic epilepsy and ragged-red fibers (MERRF); Leigh Syndrome; Alpers Syndrome; mitochondrial neurogastrointestinal encephalomyopathy (MNGIE); Kearns-Sayre Syndrome (KSS); Combined oxidative phosphorylation deficiency 11 (COXPD11); Leber's hereditary optic neuropathy (LHON); Autosomal Dominant Optic Atrophy (ADOA); Devic's disease/Neuromyelitis Optica; Charcot-Marie Tooth Disease type 2A2 (CMT2A2); CMT4; Developmental and epileptic encephalopathy 39 (EIEE39); Encephalopathy due to defective mitochondrial and peroxisomal fission-1 (EMPF1); Multiple Sclerosis; X-linked adrenoleukodystrophy and Vanishing White Matter Disease (VWMD). In some embodiments, the myelin and mitochondria associated disease is Leigh Syndrome.

In some embodiments, administering of a frataxin replacement therapeutic compound to a subject for treating a myelin associated disease or a myelin and mitochondria associated disease modulates at least one frataxin-sensitive genomic marker (FSGM) associated with myelination processes as listed in Table 12, i.e., modulates the amount or activity of at least one protein selected from the group consisting of ABCE1, EIF1A, EGR1, EGR2, EGR3, SERPINE1 (PAi), CCN1 (CYR61), THBS1, NR4A1 (Nurr77), RTN4 (NOGO) and TMEM126A. That is, in some embodiments, the amount or activity of at least one FSGM as listed in Table 12 in the subject prior to administration of a frataxin replacement therapeutic compound is different from the amount or activity of the at least one FSGM in the subject after administration of a frataxin replacement therapeutic compound.

In some embodiments, administering of a frataxin replacement therapeutic compound to a subject for treating a myelin associated disease or a myelin and mitochondria associated disease modulates at least one biomarker of neurodegeneration. That is, in some embodiments, the amount or activity of at last one biomarker of neurodegeneration in the subject prior to administration of a frataxin replacement therapeutic compound is different from the amount or activity of the at least one biomarker of neurodegeneration in the subject after administration of a frataxin replacement therapeutic compound. In some embodiments, administering of a frataxin replacement therapeutic compound to a subject for treating a myelin associated disease or a myelin and mitochondria associated disease decreases plasma levels of neurofilament light chain (NfL) and phosphorylated neurofilament heavy chain (pNfH) in the subject.

In some embodiments, administering of a frataxin replacement therapeutic compound to a subject for treating a myelin associated disease or a myelin and mitochondria associated disease increases the amount of myelin in the subject. That is, in some embodiments, the amount of myelin in the subject prior to administration of a frataxin replacement therapeutic compound is lower than the amount of myelin in the subject after administration of a frataxin replacement therapeutic compound. The amount of myelin in a subject may be assessed by any methods known to one of ordinary skill in the art for assessing the mount of myelin, e.g., using imaging, such as MRI or CT scan. In some embodiments, the increase of myelin resulting from the administration of a frataxin replacement therapeutic is systemic. In some embodiments, the increase of myelin resulting from the administration of a frataxin replacement therapeutic is localized to a particular tissue or organ (e.g., peripheral CNS or central CNS).

In some embodiments, administering of the FXN replacement therapeutic compound to the subject for promoting neuronal survival modulates at least one frataxin-sensitive genomic marker (FSGM) in the subject. In some embodiments, the FSGM may be selected from the group consisting of CYR61, EGR1 and NR4A1.

In some embodiments, the present disclosure provides methods of increasing the amount of myelin in a subject with a myelin associated disease or a myelin and mitochondria associated disease. The methods comprise administering to the subject an effective amount of a frataxin replacement therapeutic compound, such that the amount of myelin in the subject is increased.

In some embodiments, the present disclosure provides a method of promoting oligodendrocyte maturation in a subject with a myelin associated disease (e.g., a myelin and mitochondria associated disease) that comprises administering to the subject an effective amount of a frataxin replacement therapeutic compound, such that oligodendrocyte maturation in the subject is increased. As mature oligodendrocytes are responsible for myelin production and deposition, promoting oligodencrocyte maturation may lead to increased amount of myelin in a subject.

In some embodiments, methods for treating a myelin associated disease (e.g., a myelin and mitochondria associated disease) provided by the present disclosure comprise administering to a subject in need thereof an FXN fusion protein comprising: 1) an amino acid sequence having at least 85%, at least 90%, at least 95%, or at least 99% sequence identity to full-length hFXN (SEQ ID NO: 1); and 2) any CPP as described herein.

In some embodiments, methods for treating a myelin associated disease (e.g., a myelin and mitochondria associated disease) provided by the present disclosure comprise administering to a subject in need thereof an FXN fusion protein comprising: 1) an amino acid sequence having at least 85%, at least 90%, at least 95%, or at least 99% sequence identity to full-length hFXN (SEQ ID NO: 1); and 2) an amino acid sequence having at least 85%, at least 90%, at least 95% or at least 99% to TAT-HIV (SEQ ID NO: 3 or SEQ ID NO: 4).

In some embodiments, methods for treating a myelin associated disease (e.g., a myelin and mitochondria associated disease) provided by the present disclosure comprise administering to a subject in need thereof an FXN fusion protein comprising: 1) an amino acid sequence having at least 85%, at least 90%, at least 95%, or at least 99% sequence identity to full-length hFXN (SEQ ID NO: 1); 2) any CPP as described herein; and 3) any TES as described herein.

In some embodiments, methods for treating a myelin associated disease (e.g., a myelin and mitochondria associated disease) provided by the present disclosure comprise administering to a subject in need thereof an FXN fusion protein comprising: 1) an amino acid sequence having at least 85%, at least 90%, at least 95%, or at least 99% sequence identity to full-length hFXN (SEQ ID NO: 1); 2) an amino acid sequence having at least 85%, at least 90%, at least 95% or at least 99% to TAT-HIV (SEQ ID NO: 3 or SEQ ID NO: 4); and 3) any TES as described herein.

For example, methods for treating a myelin associated disease (e.g., a myelin and mitochondria associated disease) provided by the present disclosure comprise administering to a subject in need thereof an FXN fusion protein comprising: 1) an amino acid sequence having at least 85%, at least 90%, at least 95%, or at least 99% sequence identity to full-length hFXN (SEQ ID NO: 1); 2) an amino acid sequence having at least 85%, at least 90%, at least 95% or at least 99% to TAT-HIV (SEQ ID NO: 3 or SEQ ID NO: 4); and 3) an amino acid sequence having at least 85%, at least 90%, at least 95% or at least 99% to Ubiquitin (SEQ ID NO: 23).

For example, methods for treating a myelin associated disease (e.g., a myelin and mitochondria associated disease) provided by the present disclosure comprise administering to a subject in need thereof an FXN fusion protein comprising: 1) an amino acid sequence having at least 85%, at least 90%, at least 95%, or at least 99% sequence identity to full-length hFXN (SEQ ID NO: 1); 2) an amino acid sequence having at least 85%, at least 90%, at least 95% or at least 99% to TAT-HIV (SEQ ID NO: 3 or SEQ ID NO: 4); and 3) an amino acid sequence having at least 85%, at least 90%, at least 95% or at least 99% to a calpain cleavage domain of SEQ ID NO: 25 or SEQ ID NO: 26.

For example, methods for treating a myelin associated disease provided by the present disclosure comprise administering to a subject in need thereof an FXN fusion protein comprising: 1) an amino acid sequence having at least 85%, at least 90%, at least 95%, or at least 99% sequence identity to full-length hFXN (SEQ ID NO: 1); 2) an amino acid sequence having at least 85%, at least 90%, at least 95% or at least 99% to TAT-HIV (SEQ ID NO: 3 or SEQ ID NO: 4); and 3) an amino acid sequence having at least 85%, at least 90%, at least 95% or at least 99% to an NES of any one of SEQ ID NOS. 42-49, e.g., SEQ ID NO: 42, SEQ ID NO: 43, SEQ ID NO: 44, SEQ ID NO: 45, SEQ ID NO: 46, SEQ ID NO: 47, SEQ ID NO: 48 or SEQ ID NO: 49.

In some embodiments, methods for treating a myelin associated disease or a myelin and mitochondria associated disease provided by the present disclosure comprise administering to a subject in need thereof a fusion protein comprising or consisting of an amino acid sequence selected from the group consisting of SEQ ID NO: 22, SEQ ID NO: 50, SEQ ID NO: 51, SEQ ID NO: 52, SEQ ID NO: 53, SEQ ID NO: 54, SEQ ID NO: 55, SEQ ID NO: 56 or SEQ ID NO: 57.

In one embodiment, methods for treating a myelin associated disease or a myelin and mitochondria associated disease) provided by the present disclosure comprise administering to a subject in need thereof a fusion protein comprising or consisting of an amino acid sequence having at least about 85%, about 90%, about 95% or about 99% sequence identity to SEQ ID NO: 22.

In one embodiment, methods for treating a myelin associated disease or a myelin and mitochondria associated disease provided by the present disclosure comprise administering to a subject in need thereof a fusion protein comprising or consisting of an amino acid sequence having at least about 85%, about 90%, about 95% or about 99% sequence identity to SEQ ID NO: 50.

In one embodiment, methods for treating a myelin associated disease or a myelin and mitochondria associated disease provided by the present disclosure comprise administering to a subject in need thereof a fusion protein comprising or consisting of an amino acid sequence having at least about 85%, about 90%, about 95% or about 99% sequence identity to SEQ ID NO: 51.

In one embodiment, methods for treating a myelin associated disease or a myelin and mitochondria associated disease provided by the present disclosure comprise administering to a subject in need thereof a fusion protein comprising or consisting of an amino acid sequence having at least about 85%, about 90%, about 95% or about 99% sequence identity to SEQ ID NO: 52.

In one embodiment, methods for treating a myelin associated disease or a myelin and mitochondria associated disease provided by the present disclosure comprise administering to a subject in need thereof a fusion protein comprising or consisting of an amino acid sequence having at least about 85%, about 90%, about 95% or about 99% sequence identity to SEQ ID NO: 53.

In one embodiment, methods for treating a myelin associated disease or a myelin and mitochondria associated disease provided by the present disclosure comprise administering to a subject in need thereof a fusion protein comprising or consisting of an amino acid sequence having at least about 85%, about 90%, about 95% or about 99% sequence identity to SEQ ID NO: 54.

In one embodiment, methods for treating a myelin associated disease or a myelin and mitochondria associated disease provided by the present disclosure comprise administering to a subject in need thereof a fusion protein comprising or consisting of an amino acid sequence having at least about 85%, about 90%, about 95% or about 99% sequence identity to SEQ ID NO: 55.

In one embodiment, methods for treating a myelin associated disease provided by the present disclosure comprise administering to a subject in need thereof a fusion protein comprising or consisting of an amino acid sequence having at least about 85%, about 90%, about 95% or about 99% sequence identity to SEQ ID NO: 56.

In one embodiment, methods for treating a myelin associated disease or a myelin and mitochondria associated disease provided by the present disclosure comprise administering to a subject in need thereof a fusion protein comprising or consisting of an amino acid sequence having at least about 85%, about 90%, about 95% or about 99% sequence identity to SEQ ID NO: 57.

In some embodiments, the present disclosure provides methods for treating Charcot-Marie-Tooth disease (CMT) that comprise administering to a subject in need thereof a frataxin replacement therapeutic compound, such that said CMT in said subject is treated. In some embodiments, the CMT is CMT type 1A (CMT1A) associated with the duplication the PMP22 gene. In some embodiments, the CMT is CMT type 2A2 (CMT2A2) associated with mutations in the gene MFN2 gene. In some embodiments, the CMT is a X-linked CMT (CMTX) associated with a mutation in the GJB1 gene. In some embodiments, the CMT is CMT type 1B (CMT1B) is associated with a mutation in the MPZ gene. In some embodiments, the CMT is CMT type 4 (CMT4) associated with a mutation in the GDAP1 gene or a SURF1 gene.

In some embodiments, methods for treating CMT provided by the present disclosure comprise administering to a subject in need thereof an FXN fusion protein comprising: 1) an amino acid sequence having at least 85%, at least 90%, at least 95%, or at least 99% sequence identity to full-length hFXN (SEQ ID NO: 1); and 2) any CPP as described herein.

In some embodiments, methods for treating CMT provided by the present disclosure comprise administering to a subject in need thereof an FXN fusion protein comprising:

1) an amino acid sequence having at least 85%, at least 90%, at least 95%, or at least 99% sequence identity to full-length hFXN (SEQ ID NO: 1); and 2) an amino acid sequence having at least 85%, at least 90%, at least 95% or at least 99% to TAT-HIV (SEQ ID NO: 3 or SEQ ID NO: 4).

In some embodiments, methods for treating CMT provided by the present disclosure comprise administering to a subject in need thereof an FXN fusion protein comprising: 1) an amino acid sequence having at least 85%, at least 90%, at least 95%, or at least 99% sequence identity to full-length hFXN (SEQ ID NO: 1); 2) any CPP as described herein; and 3) any TES as described herein.

In some embodiments, methods for treating CMT provided by the present disclosure comprise administering to a subject in need thereof an FXN fusion protein comprising: 1) an amino acid sequence having at least 85%, at least 90%, at least 95%, or at least 99% sequence identity to full-length hFXN (SEQ ID NO: 1); 2) an amino acid sequence having at least 85%, at least 90%, at least 95% or at least 99% to TAT-HIV (SEQ ID NO: 3 or SEQ ID NO: 4); and 3) any TES as described herein.

For example, methods for treating CMT provided by the present disclosure comprise administering to a subject in need thereof an FXN fusion protein comprising: 1) an amino acid sequence having at least 85%, at least 90%, at least 95%, or at least 99% sequence identity to full-length hFXN (SEQ ID NO: 1); 2) an amino acid sequence having at least 85%, at least 90%, at least 95% or at least 99% to TAT-HIV (SEQ ID NO: 3 or SEQ ID NO: 4); and 3) an amino acid sequence having at least 85%, at least 90%, at least 95% or at least 99% to Ubiquitin (SEQ ID NO: 23).

For example, methods for treating CMT provided by the present disclosure comprise administering to a subject in need thereof an FXN fusion protein comprising: 1) an amino acid sequence having at least 85%, at least 90%, at least 95%, or at least 99% sequence identity to full-length hFXN (SEQ ID NO: 1); 2) an amino acid sequence having at least 85%, at least 90%, at least 95% or at least 99% to TAT-HIV (SEQ ID NO: 3 or SEQ ID NO: 4); and 3) an amino acid sequence having at least 85%, at least 90%, at least 95% or at least 99% to a calpain cleavage domain of SEQ ID NO: 25 or SEQ ID NO: 26.

For example, methods for treating CMT provided by the present disclosure comprise administering to a subject in need thereof an FXN fusion protein comprising e 1) an amino acid sequence having at least 85%, at least 90%, at least 95%, or at least 99% sequence identity to full-length hFXN (SEQ ID NO: 1); 2) an amino acid sequence having at least 85%, at least 90%, at least 95% or at least 99% to TAT-HIV (SEQ ID NO: 3 or SEQ ID NO: 4); and 3) an amino acid sequence having at least 85%, at least 90%, at least 95% or at least 99% to an NES of any one of SEQ ID NOS. 42-49, e.g., SEQ ID NO: 42, SEQ ID NO: 43, SEQ ID NO: 44, SEQ ID NO: 45, SEQ ID NO: 46, SEQ ID NO: 47, SEQ ID NO: 48 or SEQ ID NO: 49.

In some embodiments, methods for treating CMT provided by the present disclosure comprise administering to a subject in need thereof a fusion protein comprising or consisting of an amino acid sequence selected from the group consisting of SEQ ID NO: 22, SEQ ID NO: 50, SEQ ID NO: 51, SEQ ID NO: 52, SEQ ID NO: 53, SEQ ID NO: 54, SEQ ID NO: 55, SEQ ID NO: 56 or SEQ ID NO: 57.

In one embodiment, methods for treating CMT provided by the present disclosure comprise administering to a subject in need thereof a fusion protein comprising or consisting of an amino acid sequence having at least about 85%, about 90%, about 95% or about 99% sequence identity to SEQ ID NO: 22.

In one embodiment, methods for treating CMT provided by the present disclosure comprise administering to a subject in need thereof a fusion protein comprising or consisting of an amino acid sequence having at least about 85%, about 90%, about 95% or about 99% sequence identity to SEQ ID NO: 50.

In one embodiment, methods for treating CMT provided by the present disclosure comprise administering to a subject in need thereof a fusion protein comprising or consisting of an amino acid sequence having at least about 85%, about 90%, about 95% or about 99% sequence identity to SEQ ID NO: 51.

In one embodiment, methods for treating CMT provided by the present disclosure comprise administering to a subject in need thereof a fusion protein comprising or consisting of an amino acid sequence having at least about 85%, about 90%, about 95% or about 99% sequence identity to SEQ ID NO: 52.

In one embodiment, methods for treating CMT provided by the present disclosure comprise administering to a subject in need thereof a fusion protein comprising or consisting of an amino acid sequence having at least about 85%, about 90%, about 95% or about 99% sequence identity to SEQ ID NO: 53.

In one embodiment, methods for treating CMT provided by the present disclosure comprise administering to a subject in need thereof a fusion protein comprising or consisting of an amino acid sequence having at least about 85%, about 90%, about 95% or about 99% sequence identity to SEQ ID NO: 54.

In one embodiment, methods for treating CMT provided by the present disclosure comprise administering to a subject in need thereof a fusion protein comprising or consisting of an amino acid sequence having at least about 85%, about 90%, about 95% or about 99% sequence identity to SEQ ID NO: 55.

In one embodiment, methods for treating CMT provided by the present disclosure comprise administering to a subject in need thereof a fusion protein comprising or consisting of an amino acid sequence having at least about 85%, about 90%, about 95% or about 99% sequence identity to SEQ ID NO: 56.

In one embodiment, methods for treating CMT provided by the present disclosure comprise administering to a subject in need thereof a fusion protein comprising or consisting of an amino acid sequence having at least about 85%, about 90%, about 95% or about 99% sequence identity to SEQ ID NO: 57.

In some embodiments, a myelin associated disease as described herein is characterized by a modulated level or activity of at least one frataxin-sensitive genomic marker (FSGM) associated with myelination processes as listed in Table 12, i.e., modulated amount or activity of at least one protein selected from the group consisting of ABCE1, EIF1A, EGR1, EGR2, EGR3, SERPINE1 (PAi), CCN1 (CYR61), THBS1, NR4A1 (Nurr77), RTN4 (NOGO) and TMEM126A. That is, in some embodiments, the amount or activity of at least one FSGM as listed in Table 12 in a subject afflicted by a myelin associated disease is different from amount or activity of at least one FSGM in a healthy subject who is not afflicted by a myelin associated disease, or is different from a threshold value.

In some examples, the modulated amount or activity of the at least one FSGM as listed in Table 12 may be a result of an increased or decreased amount (e.g., expression level) or an increased or decreased activity of the at least one FSGM in a subject afflicted with a myelin associated disease as compared to the amount (e.g., expression level) or activity of the at least one FSGM in a healthy subject, or as compared to a threshold value.

In some embodiments, a myelin associated disease is characterized by a decreased amount or activity, e.g., a decreased amount, of at least one FSGM as listed in Table 12, i.e., at least one protein selected from the group consisting of ABCE1, EIF1A, EGR1, EGR2, EGR3, SERPINE1 (Pai), CCN1 (CYR61), THBS1, NR4A1 (Nurr77), RTN4 (NOGO) and TMEM126A.

In another aspect, a myelin associated disease is characterized by an increased amount or activity, e.g., an increased amount, of at least one FSGM as listed in Table 12, i.e., at least one protein selected from the group consisting of ABCE1, EIF1A, EGR1, EGR2, EGR3, SERPINE1 (Pai), CCN1 (CYR61), THBS1, NR4A1 (Nurr77), RTN4 (NOGO) and TMEM126A.

In some embodiments, administration of a frataxin replacement therapeutic compound, e.g., exemplary TAT-hFXN fusion protein, to a subject in need thereof for treating or ameliorating a myelin associated disease in accordance with methods of the present disclosure results in a modulation of at least one FSGM as listed in Table 12, e.g., modulation of at least one protein selected from the group consisting of ABCE1, EIF1A, EGR1, EGR2, EGR3, SERPINE1 (Pai), CCN1 (CYR61), THBS1, NR4A1 (Nurr77), RTN4 (NOGO) and TMEM126A. Accordingly, the present disclosure also provides methods for modulating a protein in a subject afflicted by a myelin associated disease that comprise administering to the subject an effective amount of a frataxin replacement therapeutic compound, e.g., exemplary TAT-hFXN fusion protein, wherein the protein is selected from the group consisting of ABCE1, EIF1A, EGR1, EGR2, EGR3, SERPINE1 (Pai), CCN1 (CYR61), THBS1, NR4A1 (Nurr77), RTN4 (NOGO) and TMEM126A.

In one specific example, the present disclosure provides a method of modulating at least one protein selected from the group consisting of EGR1, EGR2, EGR3, CRY61, EIF1A and ABCE1 in a subject afflicted by Guillain-Barré Syndrome, comprising administering to the subject a frataxin replacement therapeutic compound such that said at least one protein in said subject is modulated.

The term "modulating a protein", as used herein, refers to causing the amount of the protein (e.g., the expression level) or the level of the protein activity to change following administration of a frataxin replacement therapeutic compound, e.g., exemplary TAT-hFXN fusion protein.

In some embodiments, a myelin associated disease comprises a disease characterized by the presence of an abnormal, e.g., defective or damaged, myelin in a subject afflicted by the myelin associated disease and also characterized by a modulated amount or activity of at least one FSGM, e.g., at least one protein selected from the group consisting of ABCE1, EIF1A, EGR1, EGR2, EGR3, SERPINE1 (Pai), CCN1 (CYR61), THBS1, NR4A1 (Nurr77), RTN4 (NOGO) and TMEM126A following administration of a frataxin replacement therapeutic compound, e.g., exemplary TAT-hFXN fusion protein.

In some embodiments, a myelin associated disease is a disease characterized by at least one symptom selected from the group consisting of ataxia, blurred vision, muscle weakness, muscle stiffness, muscle spasms, heart palpitations, dizziness, uncoordinated movements and fatigue and also characterized by a modulated amount or activity of at least one FSGM, e.g., at least one protein selected from the group consisting of ABCE1, EIF1A, EGR1, EGR2, EGR3, SERPINE1 (Pai), CCN1 (CYR61), THBS1, NR4A1 (Nurr77), RTN4 (NOGO) and TMEM126A following administration of a frataxin replacement therapeutic compound, e.g., exemplary TAT-hFXN fusion protein.

In some embodiments, the myelin associated disease is a Guillain-BarrÉ Syndrome and is characterized by a modulated amount or activity of at least one protein selected from the group consisting of EGR1, EGR2, EGR3, CRY61, EIF1A and ABCE1.

The term "modulation of a protein" or "modulation of at least one protein", as used herein, refers to causing increased or decreased amount (e.g., level of expression) of the protein in a subject, e.g., a subject being administered a frataxin replacement therapeutic compound, or a cell being contacted with a frataxin replacement therapeutic compound. The term "modulation of a protein" or "modulation of at least one protein", as used herein, also refers to causing increased or decreased activity of the protein.

Thus, in some embodiments of the disclosure, the frataxin replacement therapeutic compound operates to provide modulation of at least one protein selected from the group consisting of ABCE1, EIF1A, EGR1, EGR2, EGR3, SERPINE1 (Pai), CCN1 (CYR61), THBS1, NR4A1 (Nurr77), RTN4 (NOGO) and TMEM126A in cells in vivo or in vitro.

IV. Methods of Treating a Mitochondria Associated Disease

The present disclosure provides methods for treating a mitochondria associated disease. The methods comprise administering to a subject in need thereof an effective amount of a frataxin replacement therapeutic compound, e.g., exemplary TAT-hFXN fusion protein, such that the mitochondria associated disease in the subject is treated.

The term "mitochondria associated disease", as used herein, refers to any disease that is characterized by a defect in the mitochondria and/or mitochondrial function. A defect in the mitochondria particularly affects high energy demand organs such as the heart, muscles, and brain, in which a defect in the mitochondria may lead to the organ dysfunction. Symptoms of a mitochondria associated disease may comprise at least one of the following: fatigue, weakness, metabolic strokes, seizure, cardiomyopathy, arrhythmia, developmental or cognitive disability, diabetes mellitus and impairment of hearing, vision, growth, liver, gastrointestinal or kidney function.

In some embodiments, the term "mitochondria associated disease" comprises myelin and mitochondria associated diseases as described herein. In some embodiments, the term "mitochondria associated disease" does not encompass one or more of Friedreich's Ataxia, human mitochondrial trifunctional protein deficiency, sudden infant death syndrome, Kearns-Sayre syndrome, and Leber's Hereditary Optic Neuropathy. In some embodiments, the term "mitochondria associated disease" does not encompass Friedreich's Ataxia (FRDA). In some embodiments, the term "mitochondria associated disease" does not encompass human mitochondrial trifunctional protein deficiency. In some embodiments, the term "mitochondria associated disease" does not encompass sudden infant death syndrome. In some embodiments, the term "mitochondria associated disease" does not encompass Kearns-Sayre syndrome. In some embodiments, the term "mitochondria associated disease" does not encompass Leber's Hereditary Optic Neuropathy.

In some embodiments, the term "mitochondria associated disease" does not encompass Leigh Syndrome, French Canadian Type (LSFC).

In some embodiments, a mitochondria associated disease as described herein is characterized by a modulated amount or activity of at least one protein as listed in Table 13, e.g., modulated activity of at least one protein selected from the group consisting of MT-ND1, MT-ND2, MT-ND3, MT-ND4, MT-CO2, MT-CO3, MT-ATP6, MT-ATP8, CYCS, SLIRP, RTN4, and TMEM-126A. That is, in some embodiments, the amount or activity of at least one protein as listed above in a subject afflicted by a mitochondria associated disease is different from amount or activity of the at least one protein as listed above in a healthy subject who is not afflicted by a mitochondria associated disease, or is different from a threshold value.

In some examples, the modulated amount or activity of the at least one protein as listed above may be a result of an increased or decreased amount or activity of the at least one protein in a subject afflicted with a mitochondria associated disease as compared to the amount or activity of the at least one protein in a healthy subject, or as compared to a threshold value.

In some embodiments, administration of a frataxin replacement therapeutic compound, e.g., exemplary TAT-hFXN fusion protein, to a subject in need thereof for treating or ameliorating a mitochondria associated disease in accordance with methods of the present disclosure results in a modulation of at least one protein as listed in Table 13, e.g., modulation of at least one protein selected from the group consisting of MT-ND1, MT-ND2, MT-ND3, MT-ND4, MT-CO2, MT-CO3, MT-ATP6, MT-ATP8, CYCS, SLIRP, RTN4, and TMEM-126A. Accordingly, the present disclosure also provides methods for modulating a protein in a subject afflicted by a mitochondria associated disease that comprise administering to the subject an effective amount of a frataxin replacement therapeutic compound, e.g., exemplary TAT-hFXN fusion protein, wherein the protein is selected from the group consisting of MT-ND1, MT-ND2, MT-ND3, MT-ND4, MT-CO2, MT-CO3, MT-ATP6, MT-ATP8, CYCS, SLIRP, RTN4, and TMEM-126A.

In one aspect, a mitochondria associated disease is characterized by a decreased amount or activity, e.g., a decreased amount, of at least one protein as listed in Table 13, e.g., at least one protein selected from the group consisting of MT-ND1, MT-ND2, MT-ND3, MT-ND4, MT-CO2, MT-CO3, MT-ATP6, MT-ATP8, CYCS, SLIRP, RTN4, and TMEM-126A.

In another aspect, a mitochondria associated disease is characterized by an increased amount or activity, e.g., an increased amount, of at least one protein as listed in Table 13, e.g., at least one protein selected from the group consisting of MT-ND1, MT-ND2, MT-ND3, MT-ND4, MT-CO2, MT-CO3, MT-ATP6, MT-ATP8, CYCS, SLIRP, RTN4, and TMEM-126A.

The term "modulating a protein", as used herein, refers to causing the amount of the protein or the level of the protein activity, to change following administration of a frataxin replacement therapeutic compound, e.g., exemplary TAT-hFXN fusion protein.

In some embodiments, the term "mitochondria associated disease" is a disease characterized by a defect in the mitochondria in a subject afflicted by the mitochondria associated disease and also characterized by a modulated amount or activity of at least one protein as listed in Table 13, e.g., at least one protein selected from the group consisting of MT-ND1, MT-ND2, MT-ND3, MT-ND4, MT-CO2, MT-CO3, MT-ATP6, MT-ATP8, CYCS, SLIRP, RTN4, and TMEM-126A following administration of a frataxin replacement therapeutic compound, e.g., exemplary TAT-hFXN fusion protein.

In some embodiments, the term "mitochondria associated disease" is a disease characterized by at least one symptom selected from the group consisting of fatigue, weakness, metabolic stroke, seizure, cardiomyopathy, arrhythmia, developmental or cognitive disability, diabetes mellitus and impairment of hearing, vision, growth, liver, gastrointestinal or kidney function, and also characterized by a modulated amount or activity of at least one protein as listed in Table 13, e.g., at least one protein selected from the group consisting of MT-ND1, MT-ND2, MT-ND3, MT-ND4, MT-CO2, MT-CO3, MT-ATP6, MT-ATP8, CYCS, SLIRP, RTN4, and TMEM-126A following administration of a frataxin replacement therapeutic compound, e.g., exemplary TAT-hFXN fusion protein.

Exemplary mitochondria associated diseases that may be treated by the methods of the present disclosure and the associated genes, if applicable, and characteristics are listed in the Table 10 below.

TABLE 10

Exemplary mitochondria associated diseases and associated characteristics

| No. | Disease Name | Associated Gene/Protein | Characteristics/Symptoms |
|---|---|---|---|
| 1 | Autosomal Dominant Optic Atrophy (ADOA) | OPA1 gene<br>Other possible genes associated with the disease are OPA2, OPA3, OPA4, OPA5, OPA6, OPA7 and OPA8 | This disease is characterized by vision impairment and loss |
| 2 | Leber's Hereditary Optic Neuropathy (LHON) and LHON Plus | MT-ND1, MT-ND4, MT-ND4L, or MT-ND6 genes | This disease is characterized by vision impairment and loss. Patients with LHON Plus may experience additional symptoms, such as movement disorders, tremors and cardiac |
| 3 | Leigh Disease or Leigh Syndrome | About 75 genes are thought to be involved in Leigh's disease, including the following:<br>pyruvate dehydrogenase (PDHC)<br>Complex I<br>Complex II<br>Complex III<br>Complex IV<br>Complex V | Leigh's Disease is a progressive neurometabolic disorder with a general onset in infancy or childhood. It is characterized on MRI by visible necrotizing lesions on the brain, particularly in the midbrain and brainstem. The child often appears normal at birth but typically begins displaying symptoms within a few months to two years of age. Initial symptoms can include the loss of basic skills such as sucking, head control, |

TABLE 10-continued

| Exemplary mitochondria associated diseases and associated characteristics | | | |
|---|---|---|---|
| No. | Disease Name | Associated Gene/Protein | Characteristics/Symptoms |
| | | SURF1<br>MT-ATP6 | walking and talking. These may be accompanied by other problems such as irritability, loss of appetite, vomiting and seizures. Eventually, the child may also have heart, kidney, vision, and breathing complications. |
| 4 | Mitochondrial Enoyl CoA reductase Protein-Associated Neurodegeneration (MEPAN) | MECR gene<br>Encodes encoding the mitochondrial trans-2-enoyl-coenzyme A-reductase | The disease is characterized by, inter alia, movement dysfunction, including involuntary movement and optic atrophy. It was first described by Heimer et al., *Am. J. Hum. Genet.* 2016, 99(6): 1229-1244. |
| 5 | Pyruvate Dehydrogenase Complex Deficiency (PDCD/PDH)<br>Other synonyms for this disease include:<br>Intermittent ataxia with pyruvate dehydrogenase deficiency<br>Lactic and pyruvate cademia with carbohydrate sensitivity<br>lactic and pyruvate cademia with episodic ataxia and weakness | E1-alpha subunit pyruvate dehydrogenase (PDHB) gene<br>PDHX<br>PDHB<br>DLAT<br>DLD | Signs and symptoms of the disease include lactic acidosis; respiratory failure; lethargy or coma; developmental delays, including intellectual disability; seizures, brain malformations, small head circumference; Leigh's Syndrome characterized by lesions in brainstem or basal ganglia, with loss of motor skills, eye movement problems, breathing problems; etc.; ataxia; dystonia; peripheral neuropathy; and hypotonia or hypertonia. |
| 6 | Thymidine kinase 2 (TKS) deficiency | TK2 gene | Symptoms of the disease include muscle weakness that progresses over time; hypotonia; breathing swallowing and chewing problems; loss of motor skills; poor reflexes, seizures or altered brain activity and function; slowed mental development; hearing loos, droopy eyelids (ptosis); and inability to move the eyes and eyebrows (progressive external ophthalmoplegia). |
| 7 | Barth Syndrome | TAZ gene<br>Encodes tafazzin protein | Barth Syndrome is a multi-system disorder with symptoms that include cardiomyopathy; neutropenia; underdeveloped skeletal musculature and muscle weakness; growth delay; exercise intolerance; cardiolipin abnormalities; and 3-methylglutaconic aciduria. |
| 8 | Complex I Deficiency | Genes associated with Complex I Deficiency include: ACAD9, ELAC2, FOXRED1, MT-ND1, MT-ND2, MT-ND3, MT-ND4, MT-ND4L, MT-ND5, MT-ND6, MT-TL1, MTFMT, NDUFA1, NDUFA2, NDUFA9, NDUFA10, NDUFA11, NDUFA12, NDUFA13, NDUFAF, 1NDUFAF2, NDUFAF3, NDUFAF4, NDUFAF5, NDUFAF6, NDUFB3, NDUFB9, NDUFB10, NDUFB11, NDUFS1, NDUFS2, NDUFS3, NDUFS4, NDUFS6, NDUFS7, NDUFS8, NDUFV1, NDUFV2, NUBPL, PPA2, TIMMDC1 and TMEM126B | A number of specific mitochondrial disorders have been associated with Complex I deficiency including: lactic acidosis; Leigh Syndrome; MELAS, syndromes of encephalomyopathy; HCM and LHON. |
| 9 | Complex II Deficiency (Succinate Dehydrogenase Deficiency) | SDHA gene<br>SDHB gene<br>SDHC gene<br>SDHD gene | There are diverse clinical presentation depending on the mutation. |
| 10 | Complex III Deficiency | MT-CYB gene<br>BCS1L gene | Symptoms may include muscle weakness (myopathy); extreme tiredness (fatigue), particularly during exercise (exercise intolerance); liver disease, kidney abnormalities, encephalopathy, psychomotor delay, movement problems, hypotonia and difficulty in communication. |

TABLE 10-continued

| Exemplary mitochondria associated diseases and associated characteristics | | | |
|---|---|---|---|
| No. | Disease Name | Associated Gene/Protein | Characteristics/Symptoms |
| 11 | Complex IV Deficiency (COX Deficiency) | Mutations in more than 20 genes have been found to be associated with Complex IV Deficiency, including: COA3, COA5, COA6, COA7, COA8, COX5A, COX6B1, COX8A, COX10, COX14, COX15, COX20, FASTKD2, LRPPRC, MT-CO1, MT-CO2, MT-CO3, PET100, PET117, SCO1, SCO2, SURF1, TACO1 | There are four types of Complex I Deficiency differentiated by symptoms and age of onset: benign infantile mitochondrial type, French-Canadian type, infantile mitochondrial myopathy type, and Leigh syndrome. |
| 12 | Complex V Deficiency | Genes associated with Complex V Deficiency include: ATP5F1A, ATP5F1E, ATPAF2, MT-ATP6, MT-ATP8, TMEM70 | Affected individuals may have feeding problems, slow growth, low muscle tone (hypotonia), extreme fatigue (lethargy), and developmental delay. They tend to develop elevated levels of lactic acid in the blood (lactic acidosis), which can cause nausea, vomiting, weakness, and rapid breathing. High levels of ammonia in the blood (hyperammonemia) can also occur in affected individuals, and in some cases result in abnormal brain function (encephalopathy) and damage to other organs. |
| 13 | Chronic progressive external ophthalmoplegia (CPEO) | Genes associated with CPEO include: AFG3L2, DNA2, MT-TI, MT-TL1, OPA1, POLG, POLG2, RNASEH1, RRM2B, SLC25A, 4SPG7, TK2, TWNK | The disease is characterized by weakness of the eye muscles, including drooping eyelids (ptosis) and weakness and paralysis of the muscles that move the eye (ophthalmoplegia). |
| 14 | Kearns-Sayre syndrome | Mitochondrial DNA | The disease is characterized by progressive external ophthalmoplegia, which is weakness or paralysis of the eye muscles that impairs eye movement and causes drooping eyelids (ptosis). Affected individuals also have pigmentary retinopathy, which results from degeneration of the light-sensing tissue of the retina that gives it a speckled and streaked appearance. Other signs or symptoms of the disease may include cardiac conduction defects, ataxia, or abnormally high levels of protein in CSF. |
| 15 | Mitochondrial encephalomyopathy, lactic acidosis, and stroke-like episodes (MELAS) | Genes associated with MELAS include: MT-ND1, MT-ND5, MT-TH, MT-TL1, MT-TV | The disease is characterized by muscle weakness and pain, recurrent headaches, loss of appetite, vomiting, and seizures. Most affected individuals experience stroke-like episodes beginning before age 40. Most people with MELAS have lactic acidosis, which can lead to vomiting, abdominal pain, fatigue, muscle weakness, and difficulty breathing. |
| 16 | Leukoencephalopathy with brain stem and spinal cord involvement and lactate elevation (LBSL) | DARS2 gene Encodes mitochondrial aspartyl-tRNA synthetase | The disease is characterized by abnormal muscle stiffness (spasticity), ataxia, deficiencies in sensing the position and vibrations of limbs. |
| 17 | Myoclonic Epilepsy and Ragged-Red Fiber Disease (MERRF) | Genes associated with MERRF include: MT-TF, MT-TH, MT-TK, MT-TL1, MT-TP, MT-TS1, MT-TS2, MT-TT | The disease is characterized by muscle twitches (myoclonus), weakness (myopathy), progressive stiffness (spasticity), recurrent seizures (epilepsy), ataxia, peripheral neuropathy, and dementia. Other possible characteristics include hearing loss or optic atrophy. Affected individuals sometimes have short stature and cardiomyopathy. |
| 18 | Ataxia neuropathy spectrum | POLG gene TWNK gene | Ataxia neuropathy spectrum includes a group of conditions called POLG-related disorders. The conditions are characterized by ataxia and neuropathy. |

TABLE 10-continued

| No. | Disease Name | Associated Gene/Protein | Characteristics/Symptoms |
|---|---|---|---|
| | Exemplary mitochondria associated diseases and associated characteristics | | |
| 19 | Alpers Syndrome | POLG gene | Lack of coordination of motor movement, partial paralysis, seizures, muscle twitching, hypotonia, liver damage, mental retardation, dementia, spastic quadriplegia in later stages, blindness. |
| 20 | Mitochondrial Neurogastrointestinal Encephalomyopathy (MNGIE) | TYMP gene Encodes thymidine phosphorylase (TP) | Progressive dysfunction of the muscles of the gastrointestinal tract (gastrointestinal dysmotility), and the associated gastrointestican symptoms, including vomiting, nausea, diarrhea, abdominal pain, premature satiety, stomach rumblings (borborygmi) and difficulty swallowing (dysphagia). Neurological symptoms include drooping of the upper eyelid (ptosis), ophthalmoplegia, hearing loss and peripheral neuropathy. |
| 21 | Combined oxidative phosphorylation deficiency 11 (COXPD11) | RMDN1 gene | Fatal neonatal/infantile encephalomyopathy with lactic acidosis, hyporeflexia/areflexia, severe hypotonia and respiratory failure. Less severe cases present with central hypotonia, global developmental delay, congenital sensorineural hearing loss, and renal disease. Additional, variably observed, clinical features include intellectual disability, seizures, and cardiomyopathy. |
| 22 | Devic's Disease (Neuromyelitis Optica) | In some cases, associated with mutations in MT-DNA | Optic neuritis; myelitis; inflammation of the spinal cord (transverse myelitis). |
| 23 | Developmental and epileptic encephalopathy 39 (EIEE39) | SLC25A12 gene Encodes calcium-binding mitochondrial carrier protein Aralar1. | Global developmental delay apparent in early infancy, early-onset seizures, hypotonia with poor motor function, and hypomyelination on brain imaging. Other features include absent speech and inability to walk; spasticity and hyperreflexia has also been reported. |
| 24 | Encephalopathy due to defective mitochondrial and peroxisomal fission-1 (EMPF1) | EMPF1 gene encoding mitochondrial and peroxisomal fission-1 DNM1L gene encoding dynamin-1-like protein | Delayed psychomotor development and hypotonia that may lead to death in childhood. Many patients develop refractory seizures, consistent with an epileptic encephalopathy, and thereafter show neurologic decline. |

In some embodiments, a mitochondria associated disease to be treated by the methods of the present disclosure is selected from the group consisting of LHON, LHON plus, Complex I Deficiency, Complex IV Deficiency, Complex V Deficiency, MELAS and Leigh Disease In some embodiments, the mitochondria associated disease comprises of consists of ADOA. In some embodiments, the mitochondria associated disease comprises of consists of LHON and LHON Plus. In some embodiments, the mitochondria associated disease comprises of consists of Leigh Syndrome. In some embodiments, the mitochondria associated disease comprises of consists of MEPAN. In some embodiments, the mitochondria associated disease comprises of consists of PDCD/PDH. In some embodiments, the mitochondria associated disease comprises of consists of TKS deficiency. In some embodiments, the mitochondria associated disease comprises of consists of Barth Syndrome. In some embodiments, the mitochondria associated disease comprises of consists of Complex I Deficiency. In some embodiments, the mitochondria associated disease comprises of consists of Complex II Deficiency. In some embodiments, the mitochondria associated disease comprises of consists of Complex III Deficiency. In some embodiments, the mitochondria associated disease comprises of consists of Complex IV Deficiency. In some embodiments, the mitochondria associated disease comprises of consists of Complex V Deficiency. In some embodiments, the mitochondria associated disease comprises of consists of CPEO. In some embodiments, the mitochondria associated disease comprises of consists of Kearns-Sayre syndrome. In some embodiments, the mitochondria associated disease comprises of consists of MELAS. In some embodiments, the mitochondria associated disease comprises of consists of LBSL. In some embodiments, the mitochondria associated disease comprises of consists of MERRF. In some embodiments, the mitochondria associated disease comprises of consists of Ataxia neuropathy spectrum. In some embodiments, the mitochondria associated disease comprises of consists of Alpers Syndrome. In some embodiments, the mitochondria associated disease comprises of consists of MNGIE. In some embodiments, the mitochondria associated disease comprises of consists of COXPD11. In some embodiments, the mitochondria associated disease comprises of consists of Devic's Disease. In some embodiments, the mitochondria associated disease comprises of consists of EIEE39. In some embodiments, the mitochondria associated disease comprises of consists of EMPF1.

In some embodiments, a mitochondria associated disease to be treated by the methods of the present disclosure may be a disease associated with a defect in the respiratory chain, e.g., a disease associated with a mutation in one or more proteins or protein subunits that functions in oxidative phosphorylation. Non-limiting examples of diseases associated with a defect in the respiratory chain may include, e.g., Complex I Deficiency, Complex II Deficiency, Complex III Deficiency, Complex IV Deficiency, Complex V Deficiency, MELAS and Leigh Disease.

In some embodiments, administering of a frataxin replacement therapeutic compound to a subject for treating a mitochondria associated disease or a myelin and mitochondria associated disease modulates at least one protein as listed in Table 13, e.g., modulates at least one protein selected from the group consisting of MT-ND1, MT-ND2, MT-ND3, MT-ND4, MT-CO2, MT-C03, MT-ATP6, MT-ATP8, CYCS, SLIRP, RTN4, and TMEM-126A. That is, in some embodiments, the amount or activity of at least one protein as listed in Table 13 in the subject prior to administration of a frataxin replacement therapeutic compound is different from amount or activity of the at least one protein as listed in Table 13 in the subject after administration of a frataxin replacement therapeutic compound.

In some embodiments, administering of a frataxin replacement therapeutic compound to a subject for treating a mitochondira associated disease or a myelin and mitochondria associated disease modulates at least one biomarker of mitochondrial dysfunction. That is, in some embodiments, the amount or activity of at last one biomarker of mitochondrial dysfunction in the subject prior to administration of a frataxin replacement therapeutic compound is different from the amount or activity of the at least one biomarker of mitochondrial dysfunction in the subject after administration of a frataxin replacement therapeutic compound.

In some embodiments, the at least one biomarker of mitochondrial dysfunction is lactate. In some embodiments, a mitochondria associated disease is characterized by increased lactate levels in the subject, e.g., in the plasma of the subject.

In some embodiments, the at least one biomarker of mitochondrial dysfunction is fibroblast growth factor-21 (FGF-21). In some embodiments, a mitochondria associated disease is characterized by increased FGF-21 levels in the subject, e.g., in the plasma of the subject.

In some embodiments, the at least one biomarker of mitochondrial dysfunction is growth and differentiation factor 15 (GDF-15). In some embodiments, a mitochondria associated disease is characterized by increased GDF-15 levels in the subject, e.g., in the plasma of the subject.

In some embodiments, administering of a frataxin replacement therapeutic compound to a subject for treating a mitochondria associated disease or a myelin and mitochondria associated disease decreases lactate levels in the subject, e.g., in the plasma of the subject. In some embodiments, administering of a frataxin replacement therapeutic compound to a subject for treating a mitochondria associated disease or a myelin and mitochondria associated disease decreases FGF-21 levels in the subject, e.g., in the plasma of the subject. In some embodiments, administering of a frataxin replacement therapeutic compound to a subject for treating a mitochondria associated disease or a myelin and mitochondria associated disease decreases GDF-15 levels in the subject, e.g., in the plasma of the subject.

In some embodiments, methods for treating a mitochondria associated disease or a myelin and mitochondria associated disease provided by the present disclosure comprise administering to a subject in need thereof an FXN fusion protein comprising: 1) an amino acid sequence having at least 85%, at least 90%, at least 95%, or at least 99% sequence identity to full-length hFXN (SEQ ID NO: 1); and 2) any CPP as described herein.

In some embodiments, methods for treating a mitochondria associated disease or a myelin and mitochondria associated disease provided by the present disclosure comprise administering to a subject in need thereof an FXN fusion protein comprising: 1) an amino acid sequence having at least 85%, at least 90%, at least 95%, or at least 99% sequence identity to full-length hFXN (SEQ ID NO: 1); and 2) an amino acid sequence having at least 85%, at least 90%, at least 95% or at least 99% to TAT-HIV (SEQ ID NO: 3 or SEQ ID NO: 4).

In some embodiments, methods for treating a mitochondria associated disease or a myelin and mitochondria associated disease provided by the present disclosure comprise administering to a subject in need thereof an FXN fusion protein comprising: 1) an amino acid sequence having at least 85%, at least 90%, at least 95%, or at least 99% sequence identity to full-length hFXN (SEQ ID NO: 1); 2) any CPP as described herein; and 3) any TES as described herein.

In some embodiments, methods for treating a mitochondria associated disease or a myelin and mitochondria associated disease provided by the present disclosure comprise administering to a subject in need thereof an FXN fusion protein comprising: 1) an amino acid sequence having at least 85%, at least 90%, at least 95%, or at least 99% sequence identity to full-length hFXN (SEQ ID NO: 1); 2) an amino acid sequence having at least 85%, at least 90%, at least 95% or at least 99% to TAT-HIV (SEQ ID NO: 3 or SEQ ID NO: 4); and 3) any TES as described herein.

For example, methods for treating a mitochondria associated disease or a myelin and mitochondria associated disease provided by the present disclosure comprise administering to a subject in need thereof an FXN fusion protein comprising: 1) an amino acid sequence having at least 85%, at least 90%, at least 95%, or at least 99% sequence identity to full-length hFXN (SEQ ID NO: 1); 2) an amino acid sequence having at least 85%, at least 90%, at least 95% or at least 99% to TAT-HIV (SEQ ID NO: 3 or SEQ ID NO: 4); and 3) an amino acid sequence having at least 85%, at least 90%, at least 95% or at least 99% to Ubiquitin (SEQ ID NO: 23).

For example, methods for treating a mitochondria associated disease or a myelin and mitochondria associated disease provided by the present disclosure comprise administering to a subject in need thereof an FXN fusion protein comprising: 1) an amino acid sequence having at least 85%, at least 90%, at least 95%, or at least 99% sequence identity to full-length hFXN (SEQ ID NO: 1); 2) an amino acid sequence having at least 85%, at least 90%, at least 95% or at least 99% to TAT-HIV (SEQ ID NO: 3 or SEQ ID NO: 4); and 3) an amino acid sequence having at least 85%, at least 90%, at least 95% or at least 99% to a calpain cleavage domain of SEQ ID NO: 25 or SEQ ID NO: 26.

For example, methods for treating a mitochondria associated disease or a myelin and mitochondria associated disease provided by the present disclosure comprise administering to a subject in need thereof an FXN fusion protein comprising e 1) an amino acid sequence having at least 85%, at least 90%, at least 95%, or at least 99% sequence identity to full-length hFXN (SEQ ID NO: 1); 2) an amino acid sequence having at least 85%, at least 90%, at least 95% or at least 99% to TAT-HIV (SEQ ID NO: 3 or SEQ ID NO: 4); and 3) an amino acid sequence having at least 85%, at least 90%, at least 95% or at least 99% to an NES of any one of SEQ ID NOS. 42-49, e.g., SEQ ID NO: 42, SEQ ID NO: 43, SEQ ID NO: 44, SEQ ID NO: 45, SEQ ID NO: 46, SEQ ID NO: 47, SEQ ID NO: 48 or SEQ ID NO: 49.

In some embodiments, methods for treating a mitochondria associated disease or a myelin and mitochondria associated disease provided by the present disclosure comprise administering to a subject in need thereof a fusion protein comprising or consisting of an amino acid sequence selected from the group consisting of SEQ ID NO: 22, SEQ ID NO: 50, SEQ ID NO: 51, SEQ ID NO: 52, SEQ ID NO: 53, SEQ ID NO: 54, SEQ ID NO: 55, SEQ ID NO: 56 or SEQ ID NO: 57.

In one embodiment, methods for treating a mitochondria associated disease or a myelin and mitochondria associated disease provided by the present disclosure comprise administering to a subject in need thereof a fusion protein comprising or consisting of an amino acid sequence having at least about 85%, about 90%, about 95% or about 99% sequence identity to SEQ ID NO: 22.

In one embodiment, methods for treating a mitochondria associated disease or a myelin and mitochondria associated disease provided by the present disclosure comprise administering to a subject in need thereof a fusion protein comprising or consisting of an amino acid sequence having at least about 85%, about 90%, about 95% or about 99% sequence identity to SEQ ID NO: 50.

In one embodiment, methods for treating a mitochondria associated disease or a myelin and mitochondria associated disease provided by the present disclosure comprise administering to a subject in need thereof a fusion protein comprising or consisting of an amino acid sequence having at least about 85%, about 90%, about 95% or about 99% sequence identity to SEQ ID NO: 51.

In one embodiment, methods for treating a mitochondria associated disease or a myelin and mitochondria associated disease provided by the present disclosure comprise administering to a subject in need thereof a fusion protein comprising or consisting of an amino acid sequence having at least about 85%, about 90%, about 95% or about 99% sequence identity to SEQ ID NO: 52.

In one embodiment, methods for treating a mitochondria associated disease or a myelin and mitochondria associated disease provided by the present disclosure comprise administering to a subject in need thereof a fusion protein comprising or consisting of an amino acid sequence having at least about 85%, about 90%, about 95% or about 99% sequence identity to SEQ ID NO: 53.

In one embodiment, methods for treating a mitochondria associated disease or a myelin and mitochondria associated disease provided by the present disclosure comprise administering to a subject in need thereof a fusion protein comprising or consisting of an amino acid sequence having at least about 85%, about 90%, about 95% or about 99% sequence identity to SEQ ID NO: 54.

In one embodiment, methods for treating a mitochondria associated disease or a myelin and mitochondria associated disease provided by the present disclosure comprise administering to a subject in need thereof a fusion protein comprising or consisting of an amino acid sequence having at least about 85%, about 90%, about 95% or about 99% sequence identity to SEQ ID NO: 55.

In one embodiment, methods for treating a mitochondria associated disease or a myelin and mitochondria associated disease provided by the present disclosure comprise administering to a subject in need thereof a fusion protein comprising or consisting of an amino acid sequence having at least about 85%, about 90%, about 95% or about 99% sequence identity to SEQ ID NO: 56.

In one embodiment, methods for treating a mitochondria associated disease or a myelin and mitochondria associated disease provided by the present disclosure comprise administering to a subject in need thereof a fusion protein comprising or consisting of an amino acid sequence having at least about 85%, about 90%, about 95% or about 99% sequence identity to SEQ ID NO: 57.

In some embodiments, a mitochondria associated disease or a myelin and mitochondria associated disease to be treated by the methods of the present disclosure may be a disease associated with a mutation in mitochondrial DNA (mtDNA), e.g., a disease associated with a mutation in one or more proteins or protein subunits that is encoded by mtDNA. For example, in some embodiments, such mitochondria associated diseases may be characterized by a modulated amount or activity of at least one protein selected from the group consisting of MT-ND1, MT-ND2, MT-ND3, MT-ND4, MT-CO2, MT-CO3, MT-ATP6 and MT-ATP8. In some embodiments, a mitochondria associated disease may be associated with a mutation in mtDNA and may include, e.g., LHON, LHON plus, Complex I Deficiency, Complex IV Deficiency, Complex V Deficiency, MELAS and Leigh Disease.

In some embodiments of the disclosure, the frataxin replacement therapeutic compound operates to provide modulation of at least one protein selected from the group consisting of MT-ND1, MT-ND2, MT-ND3, MT-ND4, MT-CO2, MT-CO3, MT-ATP6, MT-ATP8, CYCS, SLIRP, RTN4, and TMEM-126A in cells in vivo or in vitro, comprising contacting the cells with a frataxin replacement therapeutic compound, such that the at least one protein is modulated in the cells.

The amount or activity of the at least one protein as listed in Table 12 or Table 13 in a subject afflicted with a myelin associated disease or a mitochondria associated disease is "significantly" higher or lower than that in a healthy subject, or than a threshold value, if the amount or activity of the at least one protein in a subject afflicted with a myelin associated disease or a mitochondria associated disease is higher or lower than that in a healthy subject, or than a threshold value by at least one standard deviation, or by at least two-fold, e.g., three-fold, four-fold, five-fold, or ten-fold or more. Alternatively, the amount or activity of the at least one protein as listed in Table 12 or Table 13 in a subject afflicted with a myelin associated disease or a mitochondria associated disease may differ, e.g., be higher or lower, than the amount or activity of at least one protein as listed in Table 12 or Table 13 in a healthy subject, or than a threshold value, by at least 10%, 15%, 20%, 25%, 30%, 35%, 40%, 45%, 50% or 60% or more.

Methods of Treating a Lactic Acidosis

In some embodiments, the present disclosure also provides methods for treating lactic acidosis in a subject with a mitochondria associated disease or a subject with a myelin and mitochondria associated disease. Lactic acidosis is a characteristic manifestation of mitochondrial dysfunction. The methods for treating lactic acidosis provided by the present disclosure comprise administering to a subject with a mitochondria associated disease or a subject with a myelin and mitochondria associated disease an effective amount of a frataxin replacement therapeutic compound, such that the lactic acidosis in the subject is treated.

In some embodiments, the subject does not have Friedreich's Ataxia. In some embodiments, the subject does not have Leigh Syndrome, French Canadian Type (LSFC). In some embodiments, the subject does not have both Friedreich's Ataxia and Leigh Syndrome, French Canadian Type (LSFC).

In some embodiments, methods for treating lactic acidosis provided by the present disclosure comprise administering to a subject with a mitochondria associated disease or a subject with a myelin and mitochondria associated disease an FXN fusion protein comprising: 1) an amino acid sequence having at least 85%, at least 90%, at least 95%, or at least 99% sequence identity to full-length hFXN (SEQ ID NO: 1); and 2) any CPP as described herein.

In some embodiments, methods for treating lactic acidosis provided by the present disclosure comprise administering to a subject with a mitochondria associated disease or a subject with a myelin and mitochondria associated disease an FXN fusion protein comprising: 1) an amino acid sequence having at least 85%, at least 90%, at least 95%, or at least 99% sequence identity to full-length hFXN (SEQ ID NO: 1); and 2) an amino acid sequence having at least 85%, at least 90%, at least 95% or at least 99% to TAT-HIV (SEQ ID NO: 3 or SEQ ID NO: 4).

In some embodiments, methods for treating lactic acidosis provided by the present disclosure comprise administering to a subject with a mitochondria associated disease or a subject with a myelin and mitochondria associated disease an FXN fusion protein comprising: 1) an amino acid sequence having at least 85%, at least 90%, at least 95%, or at least 99% sequence identity to full-length hFXN (SEQ ID NO: 1); 2) any CPP as described herein; and 3) any TES as described herein.

In some embodiments, methods for treating lactic acidosis provided by the present disclosure comprise administering to a subject with a mitochondria associated disease or a subject with a myelin and mitochondria associated disease an FXN fusion protein comprising: 1) an amino acid sequence having at least 85%, at least 90%, at least 95%, or at least 99% sequence identity to full-length hFXN (SEQ ID NO: 1); 2) an amino acid sequence having at least 85%, at least 90%, at least 95% or at least 99% to TAT-HIV (SEQ ID NO: 3 or SEQ ID NO: 4); and 3) any TES as described herein.

For example, methods for treating lactic acidosis provided by the present disclosure comprise administering to a subject with a mitochondria associated disease or a subject with a myelin and mitochondria associated disease an FXN fusion protein comprising: 1) an amino acid sequence having at least 85%, at least 90%, at least 95%, or at least 99% sequence identity to full-length hFXN (SEQ ID NO: 1); 2) an amino acid sequence having at least 85%, at least 90%, at least 95% or at least 99% to TAT-HIV (SEQ ID NO: 3 or SEQ ID NO: 4); and 3) an amino acid sequence having at least 85%, at least 90%, at least 95% or at least 99% to Ubiquitin (SEQ ID NO: 23).

For example, methods for treating lactic acidosis provided by the present disclosure comprise administering to a subject with a mitochondria associated disease or a subject with a myelin and mitochondria associated disease an FXN fusion protein comprising: 1) an amino acid sequence having at least 85%, at least 90%, at least 95%, or at least 99% sequence identity to full-length hFXN (SEQ ID NO: 1); 2) an amino acid sequence having at least 85%, at least 90%, at least 95% or at least 99% to TAT-HIV (SEQ ID NO: 3 or SEQ ID NO: 4); and 3) an amino acid sequence having at least 85%, at least 90%, at least 95% or at least 99% to a calpain cleavage domain of SEQ ID NO: 25 or SEQ ID NO: 26.

For example, methods for treating lactic acidosis provided by the present disclosure comprise administering to a subject with a mitochondria associated disease or a subject with a myelin and mitochondria associated disease an FXN fusion protein comprising e 1) an amino acid sequence having at least 85%, at least 90%, at least 95%, or at least 99% sequence identity to full-length hFXN (SEQ ID NO: 1); 2) an amino acid sequence having at least 85%, at least 90%, at least 95% or at least 99% to TAT-HIV (SEQ ID NO: 3 or SEQ ID NO: 4); and 3) an amino acid sequence having at least 85%, at least 90%, at least 95% or at least 99% to an NES of any one of SEQ ID NOS. 42-49, e.g., SEQ ID NO: 42, SEQ ID NO: 43, SEQ ID NO: 44, SEQ ID NO: 45, SEQ ID NO: 46, SEQ ID NO: 47, SEQ ID NO: 48 or SEQ ID NO: 49.

In some embodiments, methods for treating lactic acidosis provided by the present disclosure comprise administering to a subject with a mitochondria associated disease or a subject with a myelin and mitochondria associated disease a fusion protein comprising or consisting of an amino acid sequence selected from the group consisting of SEQ ID NO: 22, SEQ ID NO: 50, SEQ ID NO: 51, SEQ ID NO: 52, SEQ ID NO: 53, SEQ ID NO: 54, SEQ ID NO: 55, SEQ ID NO: 56 or SEQ ID NO: 57.

In one embodiment, methods for treating lactic acidosis provided by the present disclosure comprise administering to a subject with a mitochondria associated disease or a subject with a myelin and mitochondria associated disease a fusion protein comprising or consisting of an amino acid sequence having at least about 85%, about 90%, about 95% or about 99% sequence identity to SEQ ID NO: 22.

In one embodiment, methods for treating lactic acidosis provided by the present disclosure comprise administering to a subject with a mitochondria associated disease or a subject with a myelin and mitochondria associated disease a fusion protein comprising or consisting of an amino acid sequence having at least about 85%, about 90%, about 95% or about 99% sequence identity to SEQ ID NO: 50.

In one embodiment, methods for treating lactic acidosis provided by the present disclosure comprise administering to a subject with a mitochondria associated disease or a subject with a myelin and mitochondria associated disease a fusion protein comprising or consisting of an amino acid sequence having at least about 85%, about 90%, about 95% or about 99% sequence identity to SEQ ID NO: 51.

In one embodiment, methods for treating lactic acidosis provided by the present disclosure comprise administering to a subject with a mitochondria associated disease or a subject with a myelin and mitochondria associated disease a fusion protein comprising or consisting of an amino acid sequence having at least about 85%, about 90%, about 95% or about 99% sequence identity to SEQ ID NO: 52.

In one embodiment, methods for treating lactic acidosis provided by the present disclosure comprise administering to a subject with a mitochondria associated disease or a subject with a myelin and mitochondria associated disease a fusion protein comprising or consisting of an amino acid sequence having at least about 85%, about 90%, about 95% or about 99% sequence identity to SEQ ID NO: 53.

In one embodiment, methods for treating lactic acidosis provided by the present disclosure comprise administering to a subject with a mitochondria associated disease or a subject with a myelin and mitochondria associated disease a fusion protein comprising or consisting of an amino acid sequence having at least about 85%, about 90%, about 95% or about 99% sequence identity to SEQ ID NO: 54.

In one embodiment, methods for treating lactic acidosis provided by the present disclosure comprise administering to a subject with a mitochondria associated disease or a subject with a myelin and mitochondria associated disease a fusion protein comprising or consisting of an amino acid sequence having at least about 85%, about 90%, about 95% or about 99% sequence identity to SEQ ID NO: 55.

In one embodiment, methods for treating lactic acidosis provided by the present disclosure comprise administering to a subject with a subject with a mitochondria associated disease or a subject with a myelin and mitochondria associated disease a fusion protein comprising or consisting of an amino acid sequence having at least about 85%, about 90%, about 95% or about 99% sequence identity to SEQ ID NO: 56.

In one embodiment, methods for treating lactic acidosis provided by the present disclosure comprise administering to a subject with a mitochondria associated disease or a subject with a myelin and mitochondria associated disease a fusion protein comprising or consisting of an amino acid sequence having at least about 85%, about 90%, about 95% or about 99% sequence identity to SEQ ID NO: 57.

In some embodiments, the present disclosure also provides methods of promoting neuronal survival in a subject in need thereof that comprise administering to the subject an effective amount of a frataxin (FXN) replacement therapeutic compound, such that neuronal survival in said subject is increased. Neuronal survival in a subject may be assessed by any method known in the art, e.g., by measuring levels of biomarkers, such as plasma levels of pNfH and/or NfL, or by using imaging, such as MRI.

In some embodiments of the foregoing methods for treating lactic acidosis, the subject has a mitochondrial associated disease. In some embodiments, the subject has a myelin and a mitochondria associated disease.

As used herein, the term "effective amount" of a frataxin replacement therapeutic compound, e.g., exemplary TAT-hFXN fusion protein, is that amount which is necessary or sufficient to treat a myelin associated disease, a mitochondria associated disease, or a myelin and mitochondria associated disease, e.g., ameliorate, improve or achieve a reduction in the severity of at least one symptom or indicator associated with a myelin associated disease, a mitochondria associated disease, or a myelin and mitochondria associated disease. In some embodiments, the term "effective amount" of a frataxin replacement therapeutic compound, e.g., exemplary TAT-hFXN fusion protein, may also be that amount which is necessary to modulate one or more proteins selected from the group consisting of ABCE1, EIF1A, EGR1, EGR2, EGR3, SERPINE1 (PAi), CCN1 (CYR61), THBS1, NR4A1 (Nurr77), RTN4 (NOGO) and TMEM126A in a subject afflicted with a myelin associated disease or with a myelin and mitochondrial associated disease. In other embodiments, the term "effective amount" of a frataxin replacement therapeutic compound, e.g., exemplary TAT-hFXN fusion protein, may also be that amount which is necessary to modulate one or more proteins selected from the group consisting of MT-ND1, MT-ND2, MT-ND3, MT-ND4, MT-CO2, MT-CO3, MT-ATP6, MT-ATP8, CYCS, SLIRP, RTN4, and TMEM-126A in a subject afflicted with a mitochondria associated disease or with a myelin and mitochondria associated disease. One of ordinary skill in the art can determine an effective amount of a frataxin replacement therapeutic compound for administration to a subject. Drug dosages and regimens for treating various conditions are well known in the art. Note in this regard, for example, Goodman & Gilman's The Pharmacological Basis of Therapeutics, 1996, Ninth Edition, McGraw-Hill, New York. The effective amount of frataxin replacement therapeutic compound may be combined with carrier materials to produce a single dosage form will vary depending upon the patient and the particular mode of administration.

As used herein, "treating" a myelin associated disease, a mitochondria associated disease, or a myelin and mitochondria associated disease in a subject in need thereof includes achieving, partially, substantially or completely, one or more of the following: ameliorating, improving or achieving a reduction in the severity of at least one symptom or indicator associated with a myelin associated disease or a mitochondria associated disease; and arresting the progression or worsening of the myelin associated disease or the mitochondria associated disease.

As used herein, the term "subject" refers to either a human or non-human animal, preferably a mammal. A human subject may be referred to as a patient. In some embodiments, the subject is a mouse, a rat, a rabbit or a dog. In some embodiments, the subject is a human.

EXAMPLES

Example 1: Identification of Frataxin Regulated Genomic Markers (FSGMs)

The goal of this experiment was to identify Frataxin Regulated Genomic Markers (FSGMs). FSGMs are genes the expression of which is modulated by administration of frataxin (FXN). The goal of this experiment was also to identify a subset of FSGMs that are involved in myelination function. This experiment utilized an exemplary TAT-hFXN fusion protein (SEQ ID NO: 22) as described above.

FXN Conditional Knockout (KO) Animals

A mouse model for Friedreich's Ataxia (FRDA), FXN-KO:MCK-Cre established by the Jackson laboratory was used. In this model $Fxn^{flox/null}$::MCK-Cre mice harbor a Cre-conditional frataxin allele of exon 2, a frataxin exon 2 global knockout allele and a cardiac/skeletal muscle-specific Cre recombinase transgene. The $Fxn_{flox/null}$::MCK-Cre mice (Stock No. 029720) develop progressive cardiomyopathy due to Frataxin protein deficiency in the heart and skeletal muscle. Mutants exhibit peak body weight by 9 weeks of age and have a mean survival of 86±5 days of age. The mutant mice exhibit cardiomyopathic phenotype that is characterized by decreased heart rate and ejection fraction, as well as fractional shortening, and are distinguishable from their non-mutant littermates by approximately 7 weeks of age. In the mutant mice, the left ventricular mass is significantly increased, as compared to the left ventricular mass of their non-mutant littermates by 9 weeks of age.

In Vivo Administration of the Exemplary TAT-hFXN Fusion Protein

Three groups of animals (eight animals in each group) were used in the study—two groups of knockout FXN-KO: MCK-Cre mice and one group of control mice. When the animals reached 5 weeks of age, the vehicle (50 mM NaOAc, 0.1 PEG) or the exemplary FXN fusion protein (10 mg/kg) was administered to animals from each group. Administration of the exemplary TAT-hFXN fusion protein was via sub-cutaneous injection at a volume of 10 mL/kg. The animals were administered the exemplary TAT-hFXN fusion protein or vehicle every 48 hours until they reached 77 days of age. Twenty-four hours after administration of the final dose at eleven weeks, all animals were sacrificed, and perfused with PBS to clarify the tissues. Hearts were excised and preserved in an RNAse-free reagent compatible with preservation of tissues for further RNA analysis. One such reagent inactivates RNases and stabilizes RNA within tissues, for example RNA Later™.

Cardiac Performance

Since conditional knock out mice have loss of FXN in the heart, cardiac performance was evaluated in all eight animals from each group by conscious ECG and anesthetized echocardiography before administration of the exemplary TAT-hFXN fusion protein at 4 weeks of age, and after administration of the exemplary TAT-hFXN fusion protein at 8 and 10 weeks of age.

RNA Sequencing (RNASeq)

RNA from representative animals from each group was isolated and prepared for sequencing. The representative animals included one vehicle treated control animal, two vehicle treated knock out animals, and two knockout animals treated with the exemplary TAT-hFXN fusion protein. RNA Sequencing was performed using KAPA Stranded RNA-Seq Kit with RiboErase (HMR) Illumina® Platforms KR1151—v4.16. About 100 million paired-end Illumina reads, 151 nucleotide in length (before trimming), were sequenced from each sample. Adapter sequences were trimmed from FastQ files using cutadapt v1.2.1. Low-quality bases (Q<30) from the 3' end of reads were removed and reads with more than 30% low-quality bases (Q<30) overall were filtered out. The remaining reads were aligned to the April 2018 Ensembl release of the mouse reference genome (GRCm38 v92 primary assembly) using RSEM v1.3.0 specifying STAR v2.5.3 as the aligner. Rsem was used to generate *.genes.results files for each sample.

Genomic Expression Following In Vivo Treatment

The hearts of FXN fusion protein-treated knock out (KO) mice or control mice were collected, and the RNA extracted for analysis. RNA sequencing as described above was used for obtaining the transcription expression profile triggered with or without treatment with the exemplary TAT-hFXN fusion protein. Analysis of the differential expression of genes following treatment with the exemplary TAT-hFXN fusion protein was performed as described below.

Differential expression (DE) analysis of the RNASeq results was performed with R version 3.44 and version 3.7 Bioconductor libraries. The non-adjusted "expected count" columns from rsem were imported with tximport and used as input for DEseq2. Tximport and DESeq2 were used with all default settings, except that genes with apparent lengths of 0 were reasserted to have lengths of 0.1 before running DESeq2. Two initial reports were compiled (data not shown) from the DESeq2 analyses: "all frataxin knockout samples versus all wild type samples", and "all drug-treated samples versus all vehicle control samples". Data in "drug-treated samples versus all vehicle control samples" report were sorted according to their adjusted p value (padj). Genes with a padj<0.005 were considered for further evaluation.

A cutoff for the base mean of 320 (read-out of the RNASeq analysis) was applied in the "frataxin knockout (KO) samples vs. all wild type (WT) samples" report, and genes below this threshold were not considered further if they were downregulated in "drug-treated samples vs. all vehicle-treated control samples".

Genes meeting these criteria, i.e., genes whose expression was (i) above 320 in the "frataxin knockout vs. WT samples" and (ii) were either up or downregulated in "drug-treated vs. vehicle-treated knockout animals"; or genes whose expression was (i) below 320 in the "frataxin knockout vs. WT samples" and (ii) were only upregulated in "drug-treated vs. vehicle-treated knockout animals" were further restricted to genes for which the log 2FoldChange was greater than 0.584 or lower than −0.584, corresponding to approximately a 2-fold induction or repression, respectively.

Genes that met all the above-described criteria were taken as Frataxin-sensitive genomic markers (FXN-induced signature) and used for generating FXN expression profile and examined for contrary regulation between the different treatments. Additional genes that fell slightly short of the criteria described above, but for which, upon further scrutiny, a strong rational existed, were included in the list of potential FSGMs as genes to be tested in additional models. For example, mt-CO2, which is up-regulated 3.21 fold in the FXN KO compared to the WT animal, and is downregulated 0.57 fold in KO treated with the exemplary TAT-hFXN fusion protein compared to vehicle treated, was included because it only narrowly missed the significance cutoff, other mt-DNA encoded Complex IV subunits did show up as being affected (mt-CO2 is expected to be similarly regulated since the gene is polycistronic), and one of the major protein levels regulated by LRPPRC, a significant hit, is mt-CO2. This progressive selection approach allowed the identification of genes that are contrary regulated by FXN gene ablation followed by FXN protein replacement, defining the replacement FXN expression profile. These genes reacted as sensitive to FXN, possibly being FXN target genes, and were considered bona fide markers of FXN replacement, as opposed to other genes, not contrary regulated, which are likely to be merely markers for changes in tissue remodeling or inflammation (data not shown).

Following in vivo treatment in mice with the exemplary TAT-hFXN fusion protein, one hundred and two (102) genes presented significant differential expression, being either upregulated or downregulated when compared to control (Fold regulation in "KO vs. WT"=baseline Frataxin(−) signature), and these are detailed in Table 11 below. Most importantly, these genes were found to be contrary regulated in the Frataxin deficient mouse model upon treatment with the exemplary TAT-hFXN fusion protein (Fold regulation in "drug (FXN fusion protein) vs. vehicle (Veh)"=replacement Frataxin signature). In other words, certain genes that showed upregulated expression in the absence of Frataxin had downregulated expression following treatment with the exemplary TAT-hFXN fusion protein. Conversely, the reverse was also true, namely certain genes that showed downregulated expression in the absence of Frataxin had upregulated expression following treatment with the exemplary TAT-hFXN fusion protein. This result was particularly surprising since Frataxin has never been described as a transcriptional regulator and therefore, regulation of downstream genes was not expected.

TABLE 11

Differentially expressed genes following treatment with the exemplary TAT-hFXN fusion protein (FXN-induced Signature)

| Gene Symbol | KO vs. WT | Exemplary TAT-hFXN fusion protein vs. Veh |
|---|---|---|
| Abce1 | 2.54 | 0.54 |
| Adamts1 | 2.45 | 0.32 |
| Adnp | 0.47 | 2.06 |
| AI480526 | 0.23 | 3.68 |
| Apold1 | 7.14 | 0.26 |
| Arc | 6.98 | 0.22 |
| Aspn | 4.44 | 0.37 |

TABLE 11-continued

Differentially expressed genes following treatment with the exemplary TAT-hFXN fusion protein (FXN-induced Signature)

| Gene Symbol | KO vs. WT | Exemplary TAT-hFXN fusion protein vs. Veh |
|---|---|---|
| Atf3 | 2.49 | 0.31 |
| Bicd1 | 2.30 | 0.48 |
| Btg2 | 3.46 | 0.54 |
| C230034O21Rik | 0.38 | 3.18 |
| Calm2 | 2.11 | 0.49 |
| Capza1 | 2.71 | 0.54 |
| Ccdc85b | 0.47 | 2.47 |
| Ccdc85c | 0.41 | 2.30 |
| Chm | 2.31 | 0.49 |
| Cops2 | 3.18 | 0.47 |
| Cript | 2.06 | 0.45 |
| Ctcfl | 0.31 | 3.67 |
| Ctss | 2.47 | 0.47 |
| Cul2 | 2.81 | 0.52 |
| Cycs | 2.02 | 0.38 |
| Cyr61 | 5.71 | 0.44 |
| D130020L05Rik | 0.21 | 5.74 |
| Dclk1 | 2.20 | 0.33 |
| Dcun1d1 | 2.71 | 0.45 |
| Dfna5 | 2.62 | 0.35 |
| Dio2 | 2.08 | 0.38 |
| Dnajb9 | 2.33 | 0.48 |
| Dsel | 2.55 | 0.43 |
| Dynlt3 | 2.33 | 0.44 |
| Egr1 | 7.21 | 0.42 |
| Egr2 | 19.26 | 0.04 |
| Egr3 | 11.78 | 0.18 |
| Mt-CO2 | 3.21 | 0.57 |
| Eif1a | 2.57 | 0.43 |
| Emp1 | 4.88 | 0.43 |
| Fam177a | 2.64 | 0.46 |
| Gmfb | 2.60 | 0.52 |
| Hist1h4n | 2.43 | 0.23 |
| Igf1 | 3.78 | 0.36 |
| Kctd12b | 4.24 | 0.49 |
| Lamp2 | 2.00 | 0.50 |
| Lamtor5 | 2.12 | 0.43 |
| Lox | 5.23 | 0.46 |
| Lypla1 | 2.18 | 0.46 |
| Lysmd3 | 2.10 | 0.46 |
| Maoa | 14.07 | 0.44 |
| Mki67 | 5.16 | 0.40 |
| Mob4 | 2.52 | 0.38 |
| Mpeg1 | 4.85 | 0.39 |
| Mt2 | 5.47 | 0.50 |
| mt-Atp6 | 7.44 | 0.23 |
| mt-Atp8 | 10.16 | 0.14 |
| mt-Co3 | 4.73 | 0.33 |
| mt-Nd1 | 4.53 | 0.33 |
| mt-Nd2 | 3.90 | 0.27 |
| mt-Nd3 | 5.58 | 0.23 |
| mt-Nd4 | 3.03 | 0.40 |
| mt-Rnr1 | 0.05 | 69.55 |
| mt-Rnr2 | 0.06 | 22.51 |
| Nr4a1 | 2.57 | 0.18 |
| Nrtn | 0.45 | 2.25 |
| Orc4 | 2.25 | 0.42 |
| Pde4a | 0.45 | 1.39 |
| Pde4b | 1.21 | 0.45 |
| Phf1 | 0.45 | 2.08 |
| Psma3 | 2.07 | 0.47 |
| Ptgs2 | 5.12 | 0.07 |
| Ptp4a1 | 2.61 | 0.51 |
| Ptprc | 2.09 | 0.33 |
| Rap1b | 2.62 | 0.47 |
| Rap2c | 3.29 | 0.48 |
| Rnf13 | 2.18 | 0.50 |
| Rnf2 | 2.12 | 0.41 |
| Rpl10 | 2.18 | 0.34 |
| Rpl24 | 2.92 | 0.49 |
| Rpl26 | 2.21 | 0.45 |
| Rpl32 | 2.60 | 0.46 |
| Rpl37rt | 0.23 | 7.79 |
| Rpl38 | 2.48 | 0.48 |
| Rpl39 | 3.21 | 0.39 |
| Rps15a | 2.53 | 0.41 |
| Rps27l | 3.49 | 0.40 |
| Rtn4 | 4.61 | 0.45 |
| Serpine1 | 4.68 | 0.37 |
| Slc26a10 | 0.44 | 3.41 |
| Slirp | 2.86 | 0.24 |
| Snord17 | 0.23 | 2.94 |
| Spry4 | 2.83 | 0.46 |
| Stc1 | 4.83 | 0.23 |
| Suv420h2 | 0.39 | 2.27 |
| Thbs1 | 3.40 | 0.35 |
| Tmem126a | 2.08 | 0.43 |
| Top2a | 4.92 | 0.27 |
| Ube2d3 | 2.94 | 0.44 |
| Vbp1 | 2.40 | 0.45 |
| Wnk2 | 0.44 | 2.29 |
| Yam1 | 0.12 | 9.77 |
| Yars | 2.33 | 1.45 |
| Zfp758 | 2.37 | 0.33 |
| Znf41-ps | 9.66 | 0.15 |
| Znrf1 | 0.49 | 2.26 |

FIG. 1 is a series of bar graphs showing 12 FXN-sensitive genomic markers (FSGMs) selected from Table 11. The selected FGSMs have been documented to be directly or indirectly involved in neurodegenerative processes that involve neuronal growth, neuronal survival and/or myelin deposition. Specifically, FIG. 1, panel A is a bar graph illustrating the fold change in gene expression in the heart tissue of WT mice treated with Vehicle vs. the heart tissue of KO mice treated with Vehicle. FIG. 1, panel A demonstrates that the selected FGSMs are upregulated in the KO mice. FIG. 1, panel B is a bar graph illustrating the fold change in gene expression in the heart tissue of KO mice treated with Vehicle vs. the heart tissue of KO mice treated with the exemplary TAT-hFXN fusion protein. FIG. 1, panel B demonstrates that the selected FGSMs were downregulated by treatment with the exemplary TAT-hFXN fusion protein.

The information from Table 11 was used to identify myelination processes that are likely affected by FXN. Listed in Table 12 are FSGMs and the associated myelination processes.

A literature review was conducted to determine the involvement of any FSGMs listed in Table 11 in cellular pathways associated with myelination processes. The FSGMs identified as being involved in myelination processes are listed in Table 12 below.

TABLE 12

| FSGMs associated with myelination processes | |
|---|---|
| FSGM(s) | Associated Myelination Process(es) |
| ABCE1 and EIF1A | ABCE1 and EIF1A are regulators of translation initiation. They are parts of the initiation complex together with EIF2b. Mutated Eif2b is responsible for Vanishing White Matter Leukoencephalopathy (CACH syndrome; Jackson et al. *Nat Rev Mol Cell Biol* 2010, 11: 113-127). |
| EGR 1, 2 and 3 | EGR 1, 2, 3 are transcription factors with identical DNA response element that are believed to be redundant in their role in the PNS and it is believed that increased expression of any of these transcription factors would be beneficial for PNS demyelination syndromes (O'Donovan et al., *Trends Neurosci* 1999, 22: 167-173).<br>EGR2 (KROX20) has been shown to be a transcription factor required for the myelinating phase of Schwann cell development as well as any maintenance required throughout the cell life. (Scaren and Meijer, *Glia* 2008, 56: 1541-1551, O'Donovan et al.. *Trends Neurosci* 1999, 22: 167-173). |
| SERPINE1 (PAi) | SERPINE1 (PAi) is Plasminogen Activator Inhibitor 1. Lack of plasminogen activator or of its receptor have been shown to aggravate the phenotypic presentation in experimental autoimmune encephalomyelitis (EAE), which is the animal model of multiple sclerosis (MS). PAi inhibits tPA, a tissue plasminogel activator. Inhibition of tPA activity or tPA knockout have been shown to block axonal growth in cultured neurons (Pittman et al. *J Neurosci* 1989, 9: 4269-86, Baranes et al. *Neuron* 1998, 21: 813-25, Minor et al. *J Neurochem* 2009, 109: 706-15). |
| CCN1 (CYR61) | CYR61 is an extracellular protein necessary for cell adhesion. It also acts as a linkage between SERPINE1, EGR2, NR4A1, and THBS. It functions in the pathways of these genes. We show here for the first time that CYR61 gene expression is upregulated in LRPPRC and FXN KD cells and in response to NGF treatment in PC12 cells.<br>CYR61 can bind to α6 and β1 Integrin Heterodimer that have been shown to Mediates Schwann Cell Interactions with Axons and Facilitates Axonal Regeneration after Peripheral Nerve Injury hence potentially inhibiting this process (Chang et al., *Neuroscience* 2018, 371: 49-59). |
| Thrombospondin 1 (THBS1) | THBS1 plays a role in normal central nervous system development by contributing to the regulation of oligodendrocyte precursor migration (Scott-Drew and ffrench-Constant *J Neurosci Res* 1997, 50: 202-214). |
| NR4A1 (Nurr77) | NR4A1 (Nurr77) is the regulator of microglia activation and a potential new target for inflammatory CNS diseases such as MS (Rothe et al., *J Immunol* 2017, 198: 3878-3885). Nur77 may be involved in Schwann cells differentiation and neurite elongation following sciatic nerve crush (Zhang et al., *J. Mol. Neurosci.* 2015, 57(1): 38-47). |
| RTN4 (NOGO) | RTN4 (NOGO) binds myelin and inhibits axon regeneration. It is expressed in oligodendrocytes in the central nervous system (CNS) (GrandPré et al. *Nature* 2000, 403: 439-444). Nogo-A, which is one of the three isoforms Nogo-A, Nogo-B and Nogo-C encoded by the gene NOGO, is a myelin-associated neurite outgrowth inhibitor. RTN4 regulates the dendrite branching and extension during development of the CNS with RTN4IP1 acting as a regulator (Angebault et al. *Am J Hum Genet* 2015, 97: 754-760).<br>RTN4IP1 is not an FSGMs, but it functionally interacts with RTN4 and phenotypically with TMEM126a. It encodes a mitochondrial protein that significantly affects the mitochondrial transport chain when it is knocked down. It accomplishes this by decreasing complex 1 and 4 enzymatic activities in the electron transport chain. It is also a regulator of RTN4 function that, in turn, controls RGC neurite outgrowth (Hanein et al. *Am J Hum Genet* 2009, 84: 493-498). RTN4IP1 is mutated in optic atrophy 6 (OPA6) (Chen et al., *Nature* 2000, 403(6768): 434-439). |
| TMEM126A | TMEM126A is associated with optic atrophy 7 (OPA7). Optic atrophy is caused, in part, by shrinkage or loss of myelin along the optic nerve (Hanein et al. *Am J Hum Genet* 2009, 84: 493-498). |

The experimental work described in Example 1 led to identification of FSGMs, and, specifically, to identification of ABCE1, EIF1A, EGR1, EGR2, EGR3, SERPINE1 (PAi), CCN1 (CYR61), THBS1, NR4A1 (Nurr77), RTN4 (NOGO) and TMEM126A as FSGMs involved in myelination function. Thus, the results demonstrate that the amount of ABCE1, EIF1A, EGR1, EGR2, EGR3, SERPINE1 (PAi), CCN1 (CYR61), THBS1, NR4A1 (Nurr77), RTN4 (NOGO) and TMEM126A is modulated by frataxin. The results indicate that myelin associated diseases, e.g., which are characterized by modulation of the amount or activity of one or more of ABCE1, EIF1A, EGR1, EGR2, EGR3, SERPINE1 (PAi), CCN1 (CYR61), THBS1, NR4A1 (Nurr77), RTN4 (NOGO) and TMEM126A may be treated by administering a frataxin replacement therapeutic compound, e.g., the exemplary TAT-hFXN fusion protein.

Example 2: String Analysis of FSGMs

The goal of this experiment was to identify cellular pathways and cellular physiological processes that are affected by frataxin. To this end, string analysis using the String database (string-db.org; Szklarczyk et al., *Nucleic Acids Research* 2016, 44(D1):D380-D384 and references therein) was performed using proteins derived from the genes listed in Table 12 and supplemented with proteins from known mitochondrial genes and proteins derived from genes involved in neural development and survival.

String analysis identifies known and/or predicted protein interactions according to their function. The parameters used for generating the clusters in the string analysis were: nodes=42; edges=174; average node degree=8.29; average local clustering coefficient=0.689; PPI enrichment p-value<$10^{-16}$. The minimum required interaction score was 0.400 (medium confidence). The following parameters were used as active interaction sources: text mining, experiments, databases, co-expression, neighborhood, gene fusion and co-occurrence. The partition used allowed one marker to be part of more than one cluster, as demonstrated by the different coloring of the proteins (represented by circles in FIG. 2). The string analysis parameters used were identical to the parameters used in Example 1, but with a slightly lowered confidence interval (0.7→0.4), which allowed for more leniency on connections.

Figure 2:
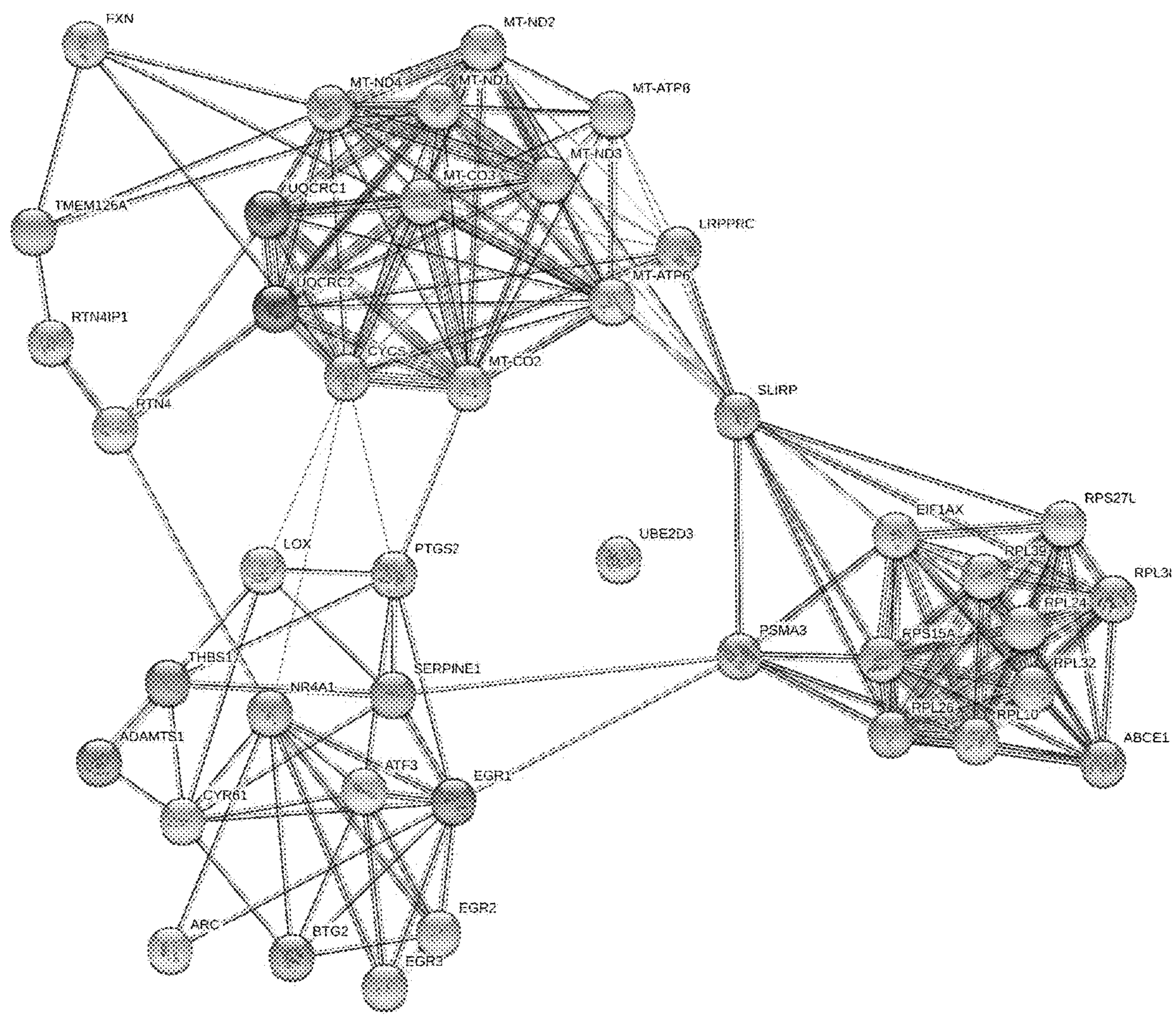
FIG. 2, panel A shows clusters generated by string analysis of predicted interactions of protein products of 42 FSGMs based on Table 11 with additional genes additions.

FIG. 2, panel A shows clusters generated by string analysis of predicted interactions of protein products of 42 FSGMs based on Table 13 with additional genes additions. FIG. 2, panel B shows the list of genes that were used to generate the String Model shown in FIG. 2, panel A. The clusters of proteins based on the string analysis indicate that the FSGM protein products have more potential interactions among themselves than would be expected for a random set of proteins of similar size, drawn from the genome. Such an enrichment indicates that the protein products of the FSGMs are at least partially biologically connected, as a group. The clusters of markers identified by the string analysis using the parameters specified above are shown in Table 13 below.

dishes in growth media (RPMI1640, Glutamax, Pen/Strep+ Amphotericin B, 10% HI-Horse Serum, and 5% FBS). The following morning, growth media was aspirated, and the cells were gently washed with PBS. The cells were treated for 1.5 hours with Differentiation Media (Optimem, Glutamax, Pen/Strep+Amphotericin B, and 0.5% FBS) containing either Vehicle, 100 ng/mL NGF (Rat Neuronal Growth Factorβ 2.5S—R&D Systems 556-NG-100), or 100 ng/mL EGF (Mouse Epidermal Growth Factor—R&D Systems 2028-EG-200). This experiment was repeated over 4 days while refreshing the media and treating every 48 hours to see neurite outgrowth.

Subsequently, the cells were washed with PBS then analyzed for gene expression using QPCR. RNA was extracted from the cells using Qiagen RNeasy Mini Kit (74104) using the manufacture's protocol. The RNA was quantified then reverse transcribed using SuperScript IV VILO Master mix With ezDNAse from Invitrogen (11766050) according to the manufacture's protocol. The cDNA was diluted to a concentration of 12.5 ng/uL. The TAQman Primers/Probe sets and the Fast-Advanced Master Mix (4444557) were purchased from ThermoFisher (GAPDH: Rn01775763_g1 GapDH VIC PL; CYR61: Rn01523136_g1 FAM; EGR1: Rn00561138_m1 FAM; NR4A1: Rn01533237_m1 FAM; and PSMA3: Rn02587201_s1 FAM). The PCR was performed in duplicate according to the Fast TAQman protocol using 25 ng of RNA in each PCR reaction. GAPDH was used as a Housekeeping gene with VIC PL dye while all target genes were made with FAM dye.

TABLE 13

Clusters of markers identified by the string analysis.

| Cluster | Markers |
|---|---|
| Nerve growth and repair signaling | NR4A1, ATF3, BTG2, EGR1, EGR2, EGR3, CYR61; RTN4, RTN4IP1, TMEM126A |
| Mitochondrial energy production | FXN, LRPPRC, MT-ND1, MT-ND2, MT-ND3, MT-ND4, MT-CO2, MT-CO3, MT-ATP6, MT-ATP8, CYCS |
| Ribosomal function | RPS15A, EIF1A, RPL24, RPL32, RPL26, RPL10, RPL39, RPL38, RPS27L; ABCE1 |
| Respiratory chain | MT-ND1, MT-ND2, MT-ND3, MT-ND4, MT-CO2, MT-CO3, CYCS |
| Matricellular signaling | ADAMTS1, THBS1, SERPINE1, CYR61 |
| Translational initiation | ABCE1, RPS15A, EIF1AX, RPL24, RPL32, RPL26, RPL10, RPL39, RPL38 |
| Mitochondrial components | MT-ND1, MT-ND2, MT-ND3, MT-ND4, MT-CO2, MT-CO3, MT-ATP6, MT-ATP8, CYCS, TMEM-126A, SLIRP, LRPPRC |

The results of this experiment indicate that cellular pathways and cellular physiological processes affected by frataxin involve nerve growth and repair signaling, mitochondrial energy production, ribosomal function, respiratory chain, matricellular signaling, translational initiation and mitochondrial components.

Example 3. Gene Expression in PC12 Cells in Response to NGF or EGF Treatment

The goal of this experiment was to determine gene expression of select FSGMs in rat adrenal pheochromocytoma (PC12) cells in response to treatment with nerve growth factor (NGF) or epidermal growth factor (EGF). NGF treatment of PC12 cells serves as a model for neuronal differentiation, whereas EGF treatment is mitogenic. For the experiment, PC12 cells were seeded at a density of 2,000 cells/$cm^2$ on poly-L-lysine and fibronectin coated 10 cm The analysis was performed by first determining the ΔCt value by subtracting the value of housekeeping gene from the value of the target gene. The ΔΔCt value was calculated by subtracting the value of vehicle-control from all other samples. Fold change was calculated using the equation $Y=2^{-x}$ where Y is the fold change and X is the ΔΔCt value. The values for the two duplicates were averaged, and the standard deviation was calculated and graphed using a $\log_2$ scale on the Y axis using Graphpad PRISM. Any value below 0.75 (downregulation) and above 1.5 (upregulation) was considered significant.

Figure 3:
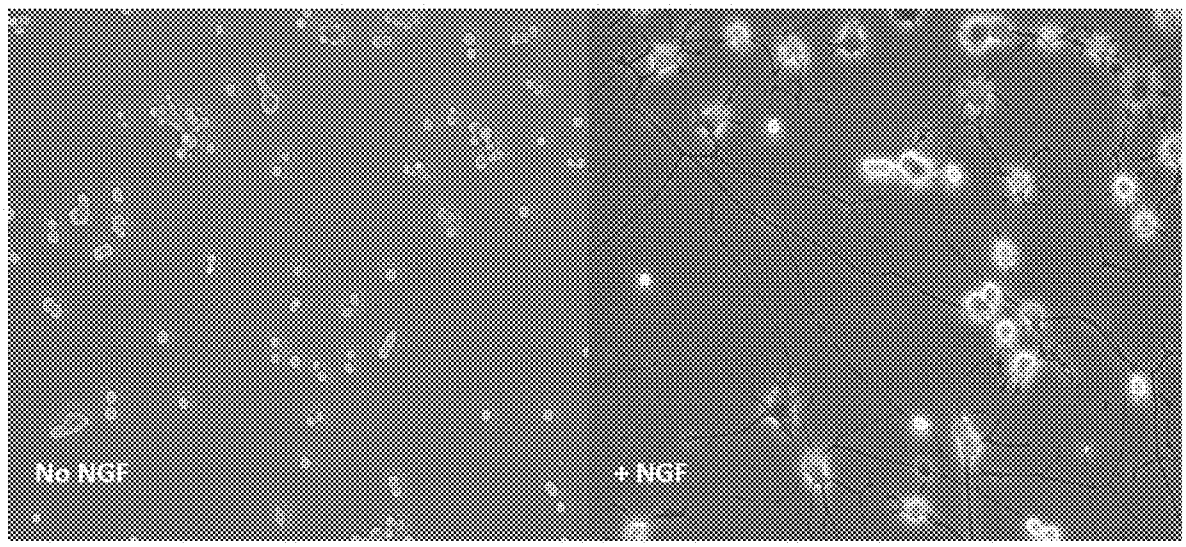
FIG. 3 shows the effect of NGF treatment of PC12 cells morphology and the effect of NGF and EGF treatment on the expression of FSGMs. Specifically, FIG. 3, panel A is a series of photographs showing the appearance of neurite outgrowth in cells treated with NGF for 1.5 hours over 4 days.
Figure 3:
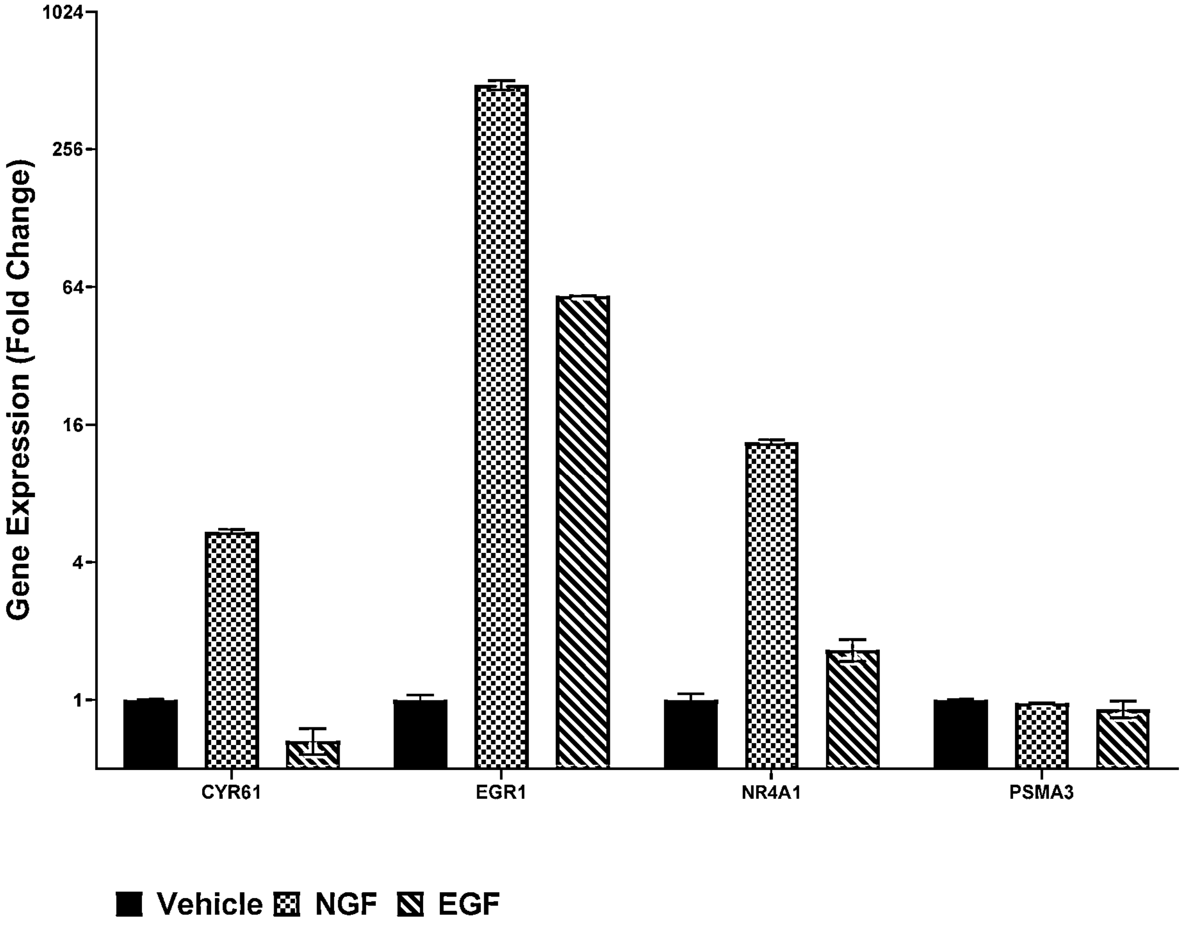

FIG. 3 shows the effect of NGF treatment of PC12 cells on morphology and the effect of NGF and EGF treatment on the expression of FSGMs. Specifically, FIG. 3, panel A is a series of photographs showing the appearance of neurite outgrowth in cells treated with NGF for 1.5 hours over 4 days.

FIG. 3, panel B shows the effect of NGF and EGF treatment on the expression of selected FSGMs in PC12 cells. As indicated in FIG. 3, panel B, compared to the vehicle control, the expression of selected FSGMs (CYR61, EGR1 and NR4A1) showed a significant upregulation of expression after treatment with NGF, but a smaller (EGR1, RN4A1) or nonexistent upregulation after treatment with EGF. The expression of PSMA3 was not affected by treatment with NGF or EGF. It was also determined that reducing serum concentration alone does not induce neurite growth or significant gene expression changes (data not shown).

The results of this experiment indicate that NGF, which is known to support neuronal survival, has an effect on the expression of several FSGMs which are, in turn, implicated in myelination. These results suggest that administration of a frataxin replacement therapeutic compound, e.g., the exemplary TAT-hFXN fusion protein, may have an effect on neuronal survival through modulation of FSGMs implicated in myelination. These results also suggest that administration of a frataxin replacement therapeutic compound, e.g., the exemplary TAT-hFXN fusion protein, may promote neuronal survival in a subject, e.g., a subject with a myelin associated disease or a subject with a myelin and mitochondria associated disease.

Example 4. Treatment of LRPPRC-Deficient Cells with the Exemplary TAT-hFXN Fusion Protein Prevents Acidification of Growth Media The goal of this experiment was to determine the effect of a frataxin replacement therapeutic compound on the mitochondrial function in LRPPRC deficient cells. LRPPRC was identified by the string analysis described in Example 2 as belonging to the cluster of markers involved in mitochondrial energy production and mitochondrial components, and LRPPRC deficient cells are expected to have mitochondrial impairment. The goal of this experiment was to determine if the mitochondrial impairment in the LRPPRC deficient cells may be alleviated by treatment with a frataxin replacement therapeutic compound, such as the exemplary TAT-hFXN fusion protein.

To produce LRPPRC deficient cells, human embryonic kidney 293 (HEK293) cells were transfected with LRPPRC short hairpin (sh)RNA contained in lentiviral particles, resulting in targeted gene silencing of LRPPRC and production of LRPPRC knock down (KD) clones KD-1C, KD-2C, KD-3C, KD-4C and KD-21C. A control cell line transfected with a scramble sequence (Scr-5) was generated in parallel, resulting in the scramble control clone. In clones KD-1C, KD-2C, KD-3C, KD-4C and KD-21C, levels of LRPPRC protein are reduced by about 70-80% when compared to the levels of LRPPRC protein in the Scramble-5 clone.

The scramble control and LRPPRC KD (clone 21C) HEK-293 cells were seeded at a density of 150,000 cells per well in 1 mL of treatment media (DMEM, 5% heat inactivated FBS, 20 mM glycerol, and 20 mM HEPES) on a 6-well tissue culture plate pre-coated with 1% fibronectin solution. After 1 hour, the cells in each well were treated with different concentrations of the exemplary TAT-hFXN fusion protein. Specifically, 50 μL of a serial dilution of the exemplary TAT-hFXN fusion protein (20 μM, 10 μM, 5 μM, 2.5 μM, and 1.25 μM, as well as 0 μM control) in formulation buffer (20 mM histidine, 250 mM sucrose, 0.05% polysorbate 20, pH 5.8) was added to each well, and the plates were incubated for 3 hours in an incubator. Subsequently, 1 mL of Complete Media (10% FBS, DMEM containing antibiotics) was added to each well, and the plates were incubated for 21 hours. This cycle was repeated 3 times on days 1, 2, and 3, and then the plates were incubated for an additional day. On day 5; pictures of the plates were taken, 1 mL of media was harvested, supplemented with 10 μL HALT protease inhibitor and frozen at −80° C. for further analysis. The RNA was extracted from the cells using Qiagen RNeasy Mini Kit (Cat #74104) using the manufacturer's protocol.

Figure 4:
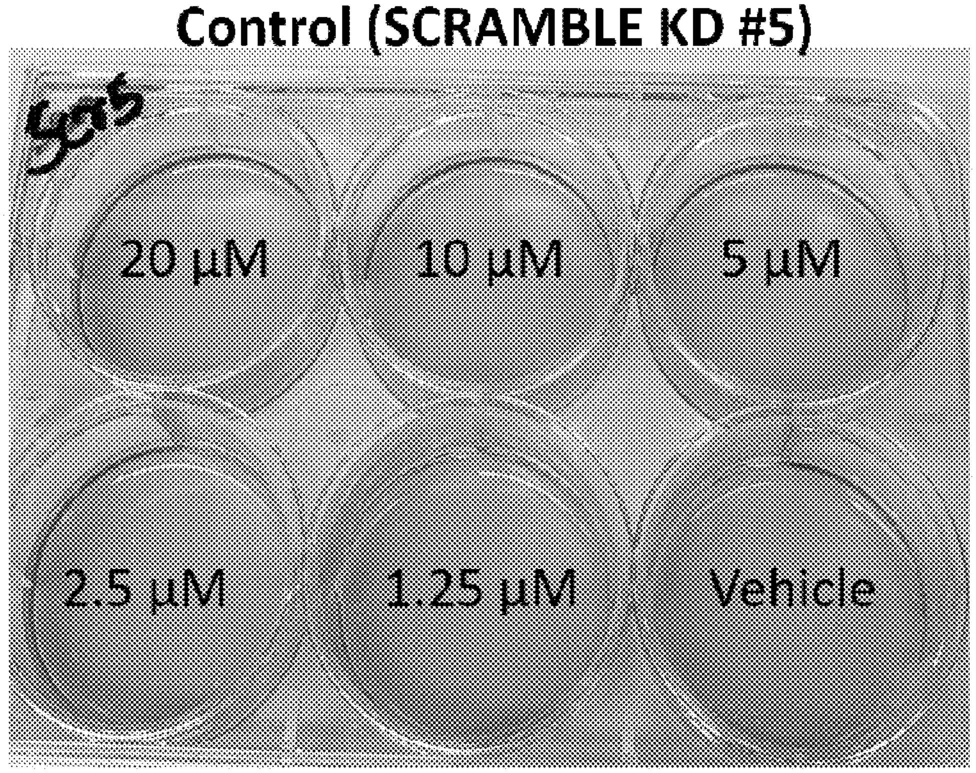
FIG. 4, panel A is a picture of culture dishes containing scramble control cells treated with different concentrations (0-20 μM) of an exemplary TAT-hFXN fusion protein.
Figure 4:
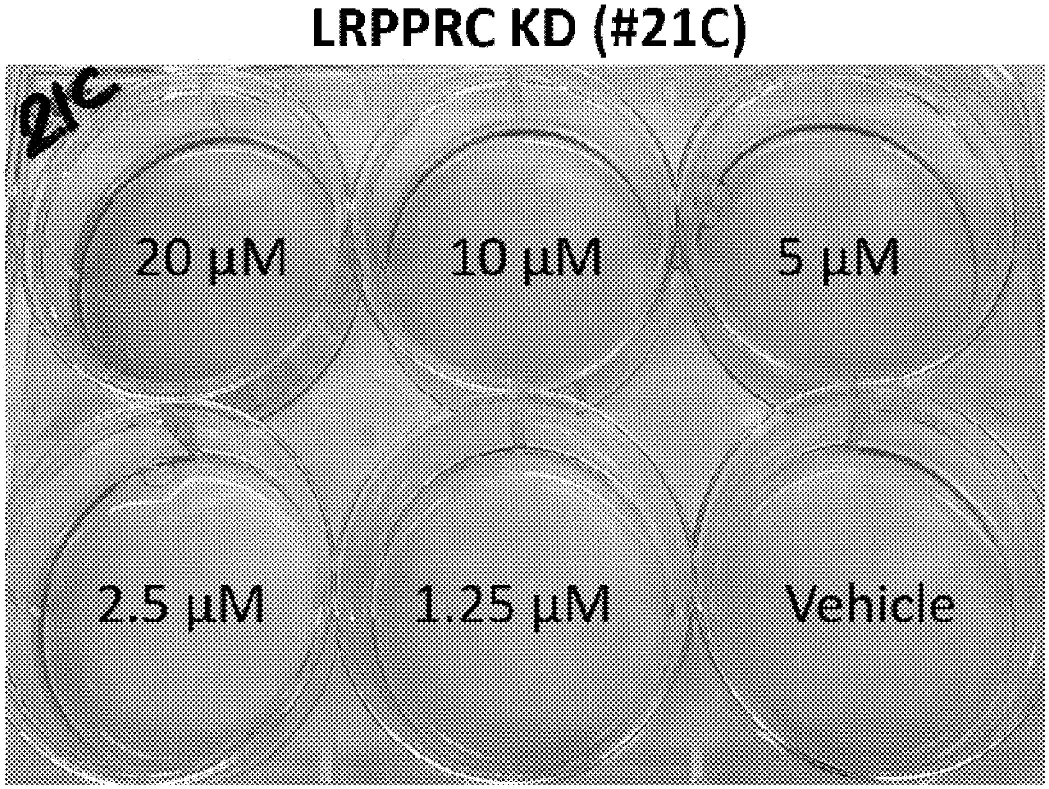
Figure 4:
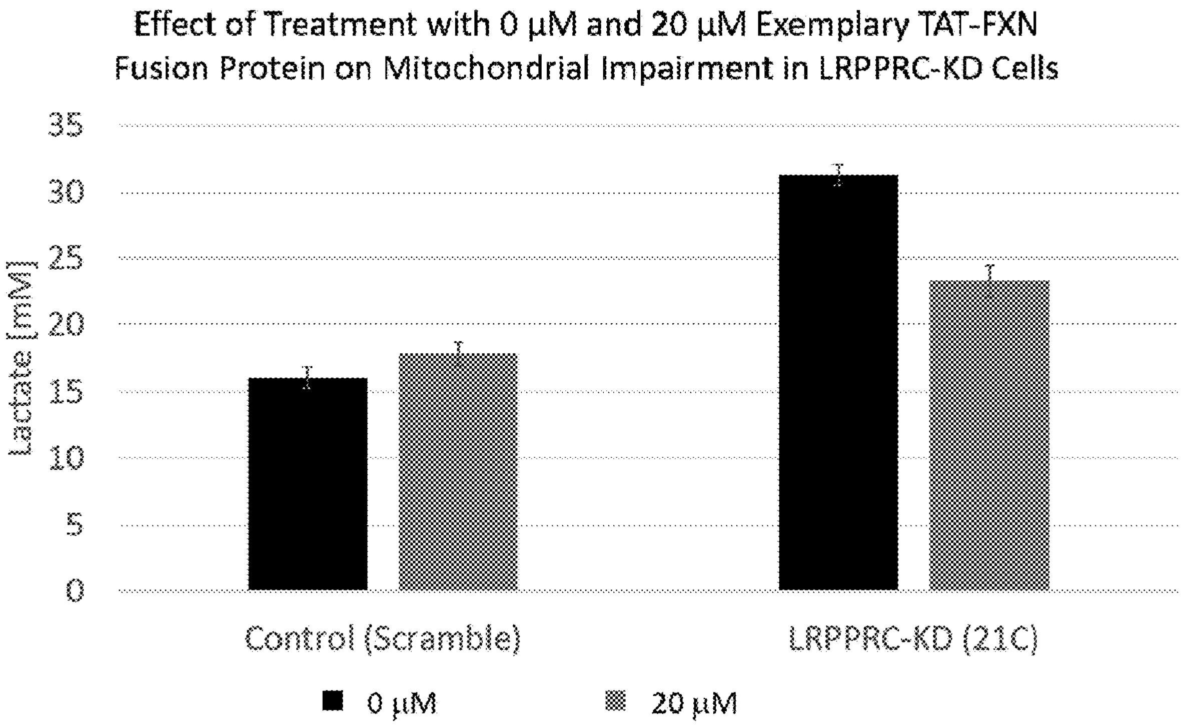
Figure 4:
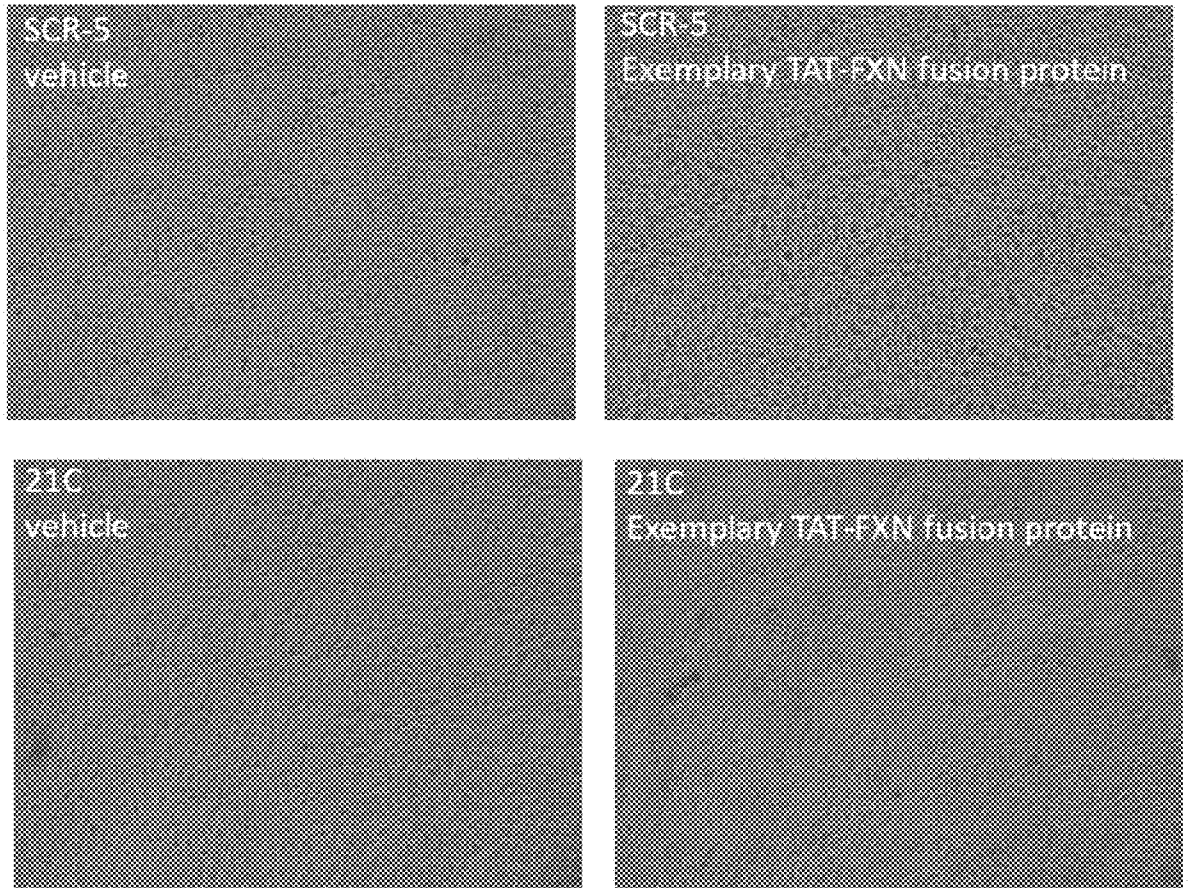

Phenol Red is the pH indicator used in DMEM media. As shown in FIG. 4, panel A, the scramble control cells did not cause a significant change in the pH of the media, as all wells appear the same red color. In contrast, as shown in FIG. 4, panel B, the LRPPRC-KD cells caused the media to turn yellow (vehicle well), indicating acidification of the media. As also shown in FIG. 4, panel B, treatment of the LRPPRC KD cells with increasing concentrations of the exemplary TAT-hFXN fusion protein prevented the acidification of the media in a dose-dependent manner, as evidenced by the color change from yellow to red with increasing concentrations of the exemplary TAT-hFXN fusion protein (yellow in the vehicle, 1.25 uM and 2.5 uM wells; orange in the 5 uM and 10 uM wells; and red in the 20 uM well). The results shown in FIG. 4 indicate that the exemplary TAT-hFXN fusion protein can reverse the effect of mitochondrial impairment exhibited by the LRPPRC-KD cells.

Levels of lactate were also measured in the media from the scramble control cells and LRPPRC KD cells using Lactate Glo Assay (Promega J5021) according to the manufacturer's protocol. The media was diluted 1:500 on a white opaque 96 well plate (Corning 3917). As shown in FIG. 4, panel C, growing LRPPRC-KD cells cause a significant increase in the amount of lactic acid in the media as compared to the scramble control cells. Treatment of the scramble control cells with 20 μM exemplary TAT-hFXN fusion protein had no significant effect on the amount of lactic acid in the media. However, treatment of LRPPRC KD cells with 20 μM exemplary TAT-hFXN fusion protein caused a significant 25% reduction of the levels of lactic acid in the media.

Cell viability and density were assessed visually using microscopic images. As shown in FIG. 4, panel D, no change in viability or density was observed for scramble control and LRPPRC-KD cells following treatment with 20 μM exemplary TAT-hFXN fusion protein or vehicle control.

The results of Example 4 indicate that knockdown of LRPPRC in HEK293 cells results in a mitochondrial impairment as evidenced by the elevated levels of lactate produced by these cells. The results of Example 4 also indicate that the mitochondrial impairment in the LRPPRC-KD cells is alleviated by treating the cells with a frataxin replacement therapeutic compound, such as the exemplary TAT-hFXN fusion protein.

Example 5: Generation of In Vitro Cell Models for Myelin Associated Diseases

An in vitro cell model of a peripheral demyelination disease is engineered by using shRNA technology to knock-down an EGR2 gene in an immortalized Schwann cell. An in vitro cell model of a central demyelination disease is engineered by using shRNA technology to knock-down one or more of ABEC1, EIF1A and EIF2 genes in an oligodendrocyte (e.g., MO3.13 cell line). The knock-down of EGR2 in the immortalized Schwann cells and ABEC1, EIF1A and EIF2 in the oligodendrocytes is confirmed by qPCR and Western blotting. The shRNA technology is also used to create scramble control Schwann cells and oligodendrocytes.

Example 6. Testing the Ability of a Frataxin Replacement Therapeutic Compound to Affect Myelination in In Vitro Cell Models for Myelin Associated Diseases The goal of this experiment is to test the ability of a frataxin replacement therapy to affect myelination in the in vitro cell models produced in Example 5. To this end, the knock-down cells and the scramble controls are transfected with a nucleic acid vector expressing full-length human frataxin or an empty control vector. The myelination ability of the knock-down Schwann cells and knock down oligodendrocytes is monitored by measuring the expression of genes involved in myelination. Specifically, in Schwann cells, the expression of MAG, MPZ and PMP22 is measured by qPCR, and the amount of MAG protein is measured by Western blotting and/or immunofluorescence. In oligodendrocytes, the expression of EGR2, MPB, MOG and PLP1 is measured by qPCR and the amount of MOG, MBP and PLP1 proteins is measured by Western blotting and/or immunofluorescence.

The myelination ability of knock-down Schwann cells and knock-down oligodendrocytes is compared to that of the scramble control cells and to the knock-down cells that have also been transduced with the exemplary TAT-hFXN fusion protein. It is expected that myelination ability of knock-down Schwann cells and knock-down oligodendrocytes is diminished as compared to the scramble control cells. It is also expected that the myelination ability in the knock-down Schwann cells and knock-down oligodendrocytes is increased when these cells are transduced with the exemplary TAT-hFXN fusion protein.

Example 7. Testing the Ability of a Frataxin Replacement Therapeutic Compound to Affect Differentiation of Human Oligodendrocyte Precursor Cells (hOPCs) in an In Vitro Model of Demyelination The goal of this experiment is to test the ability of a frataxin replacement therapeutic compound to affect differentiation of human oligodendrocyte precursor cells (hOPCs) in an in vitro model of demyelination. To this end, hOPCs are cultured in the presence of cuprizone to induce demyelination, and then are transduced with a nucleic acid vector expressing human frataxin or a control vector. Subsequently, the cells are cultured in a differentiation media. The ability of hOPCs to differentiate into oligodendrocyte is determined by measuring the expression of MOG, PLP1, MAP2, MBP, Sox10, GalC, GFAP and NG2, where the increased expression of MOG, PLP1, MBP, GalC and the decreased expression of Sox10, GFAP, and NG2 indicates the enhanced differentiation ability.

The differentiation ability of hOPCs that have been cultured in the presence of cuprizone and have been transduced with a nucleic acid vector expressing human frataxin will be compared to the differentiation ability of hOPCs that have been transduced with a control vector.

Example 8: Frataxin Replacement Therapeutic Compound Decreases Neurodegeneration in a Mouse Model of Demyelination The goal of this experiment is to test the ability of a frataxin replacement therapeutic compound, e.g., the exemplary TAT-hFXN fusion protein, to affect neurodegeneration in a mouse model of Leigh Syndrome and demyelination. The mouse model used in this experiment was the Ndufs KO mouse model harboring a mutation in the NDUFS4 gene encoding a small 18 kD protein of mitochondrial Complex I. The Ndufs KO mouse model is described, e.g., in Kruse et al., "Mice with mitochondrial complex I deficiency develop a fatal encephalomyopathy", *Cell Metab.* 2008 April; 7(4):312-20, the entire contents of which are hereby incorporated herein by reference. Mutations in the NDUFS4 gene lead to mitochondrial dysfunction and demyelination. The Ndufs4 KO mice used in the experiment were derived from crossing heterozygous B6.129S4-Ndufs4$^{tm1.1Rpa}$/J (JAX Stock 027058). Specifically, the heterozygous mice were crossed to each other and genotyped; the progeny mice that were homozygous knockout mice were used in the experiment as Ndufs4 KO mice, while the progeny mice that were homozygous for the wild type NDUFS4 allele served as the wild type controls.

In the experiment, plasma levels of neurofilament light chain (NfL) and phosphorylated neurofilament heavy chain (pNfH) were measured in the plasma of Ndufs4 KO mice. NfL and/or pNfH are known as biomarkers of neuronal degeneration as described, e.g., in Gaetani et al., "Neurofilament light chain as a biomarker in neurological disorders", *J Neurol Neurosurg Psychiatry* 2019; 0:1-12. doi: 10.1136/jnnp-2018-320106; Schaepdryver et al., "Comparison of elevated phosphorylated neurofilament heavy chains in serum and cerebrospinal fluid of patients with amyotrophic lateral sclerosis", *J Neurol Neurosurg Psychiatry* 2017; 0:1-7. doi:10.1136/jnnp-2017-316605; and Hayer et al., "NfL and pNfH are increased in Friedreich's ataxia", *J of Neurol* 2020, 267:1420-1430, the entire contents of each of which are hereby incorporated herein by reference. The goal of the experiment was to test whether the Ndufs4 KO mice, which are known to demonstrate neurodegeneration and demyelination, have increased plasma levels of NfL and/or pNfH and if treatment with a frataxin replacement therapeutic compound can cause a decrease in the plasma levels of NfL and/or pNfH.

For the experiment, wild-type and Ndufs4 KO mice were dosed subcutaneously with 30 mg/kg exemplary TAT-hFXN fusion protein or vehicle (20 mM histidine, 250 mM sucrose and 0.05% polysorbate-20). The doses were delivered daily for 7 weeks starting at the age of 3-4 weeks. Mouse plasma was collected at the end of the study and analyzed for the levels of NfL and pNfH at the Quanterix Accelerator Laboratory using the Simoa NF-light assay and the Simoa PNF-heavy assay.

Figure 5:
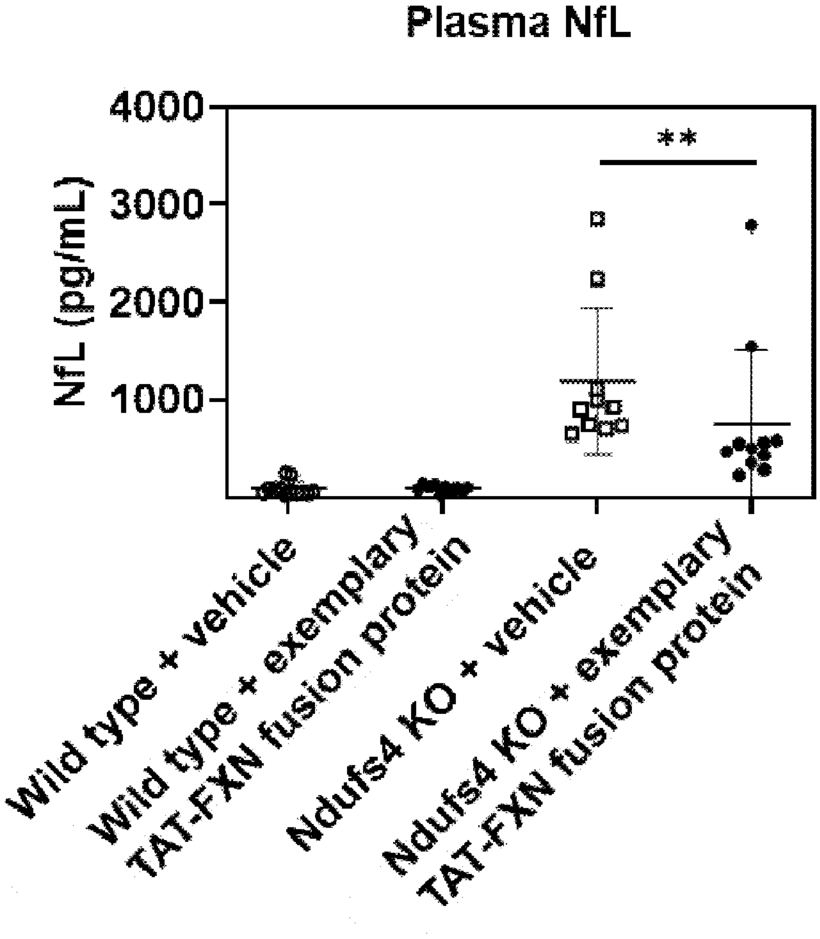
FIG. 5, panel A is a dot plot showing plasma levels of NfL in wild-type and Ndufs4 KO mouse model of Leigh Syndrome and demyelination following treatment with vehicle (as a negative control) and the exemplary TAT-hFXN fusion protein.
Figure 5:
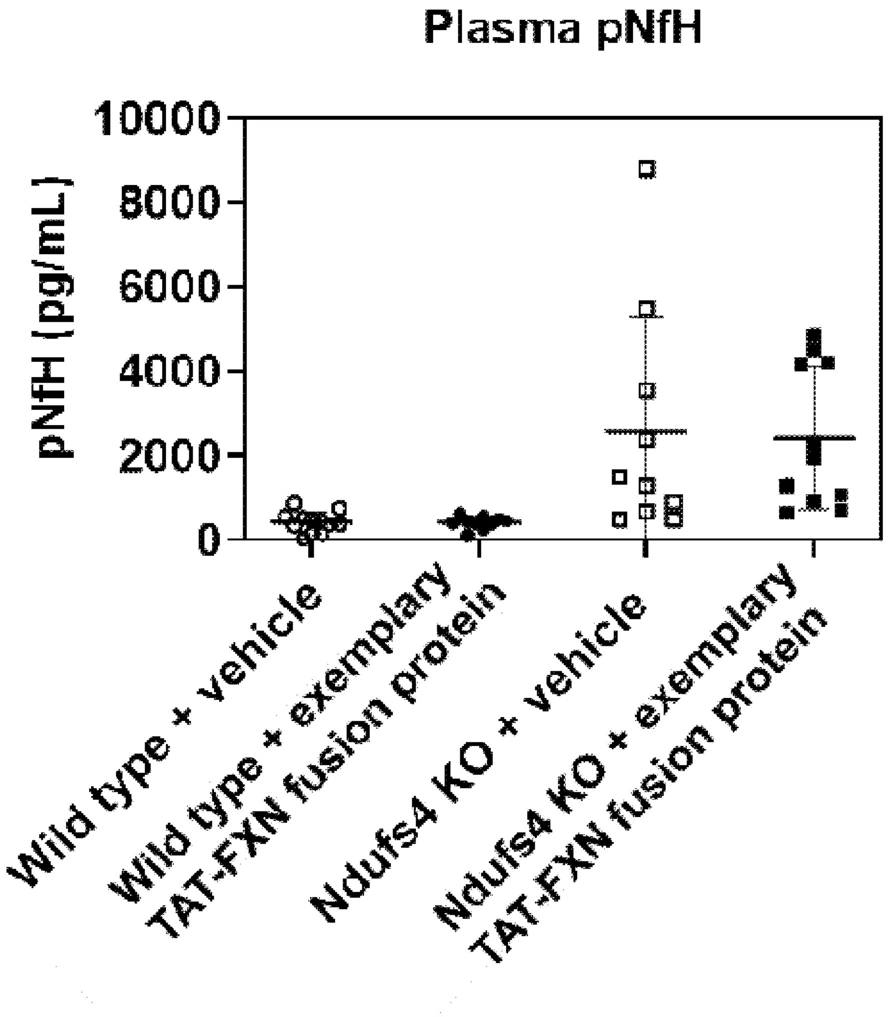

FIG. 5, panel A is a dot plot showing plasma levels of NfL in wild-type and Ndufs4 KO mouse model of Leigh Syndrome and demyelination following treatment with vehicle (as a negative control) and the exemplary TAT-hFXN fusion protein. FIG. 5, panel B is a dot plot showing plasma levels of pNfH in wild-type and Ndufs4 KO mouse model of Leigh Syndrome and demyelination following treatment with vehicle (as a negative control) and the exemplary TAT-hFXN fusion protein.

The results shown in FIG. 5, panels A and B, demonstrate that wild-type mice display relatively low plasma levels of NfL and pNfH, and that these levels are not significantly altered by treatment with the exemplary TAT-hFXN fusion protein. The results also demonstrate that plasma levels of NfL and pNfH are increased in Ndufs4 KO mice indicating neuronal degeneration in these mice. Finally, the results also demonstrate that plasma levels of NfL are statistically significantly decreased in Ndufs4 KO mice following a 7-week treatment with the exemplary TAT-hFXN fusion protein. These results indicate that treatment with a frataxin replacement therapeutic compound, such as the exemplary TAT-hFXN fusion protein, may decrease levels of neurodegeneration in a subject with a myelin and mitochondria associated disease, e.g., Leigh Syndrome.

Example 9. Frataxin Replacement Therapeutic Compound Decreases Neurodegeneration in a Mouse Model of Demyelination The goal of this experiment is to test the ability of a frataxin replacement therapeutic compound, e.g., the exemplary TAT-hFXN fusion protein, to affect neurodegeneration in a mouse model of demyelination. The mouse model of demyelination used in this experiment is a model that involves administering to the wild-type cuprizone and rapamycin to induce demyelination and is described in, e.g., Bai et al., "A mouse model for testing remyelinating therapies", *Exp Neurol* 2016, 283(Pt A):330-340, the entire contents of which are hereby incorporated herein by reference. In this model, cuprizone is administered orally by mixing with the chow, and rapamycin is injected.

For the experiment, wild-type mice (C57BL/6J; JAX Stock 000664) were fed with chow containing 0.3% cuprizone (Sigma C9012) and dosed with 10 mg/kg rapamycin for 12 weeks via intraperitoneal injection to induce demyelination. Subsequently, the mice were switched to standard chow, and dosed for 6 additional weeks with 10 mg/kg of the exemplary TAT-hFXN fusion protein, or 0.3 mg/kg T3 (Sigma T2877), or with vehicle (20 mM histidine, 250 mM sucrose and 0.05% polysorbate-20. T3, which is a thyroid hormone known to promote myelination, was used as a positive control in this experiment. Subsequently, the mice were sacrificed, their plasma was collected and analyzed for the levels of biomarkers of neuronal degeneration pNfH and NfL at the Quanterix Accelerator Laboratory using the Simoa NF-light assay and the Simoa PNF-heavy assay.

Figure 6:
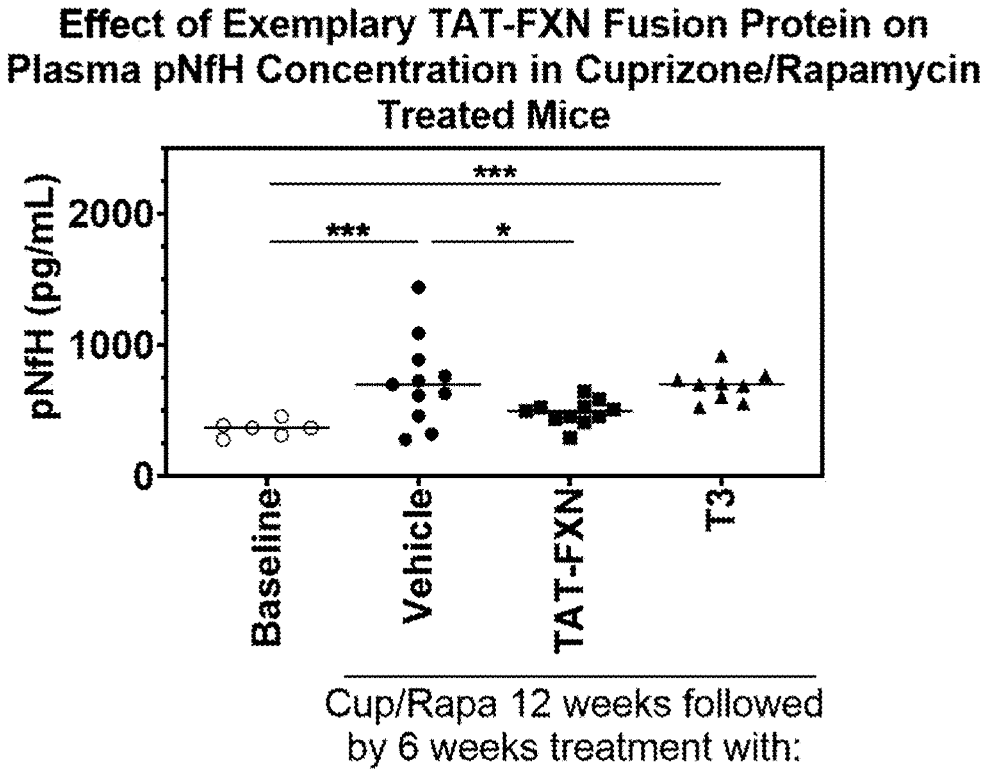
FIG. 6, panel A is a dot plot showing plasma levels of pNfH in cuprizone/rapamycin treated mouse model of demyelination following treatment with vehicle (as a negative control), T3 (as a positive control) and the exemplary TAT-hFXN fusion protein.
Figure 6:
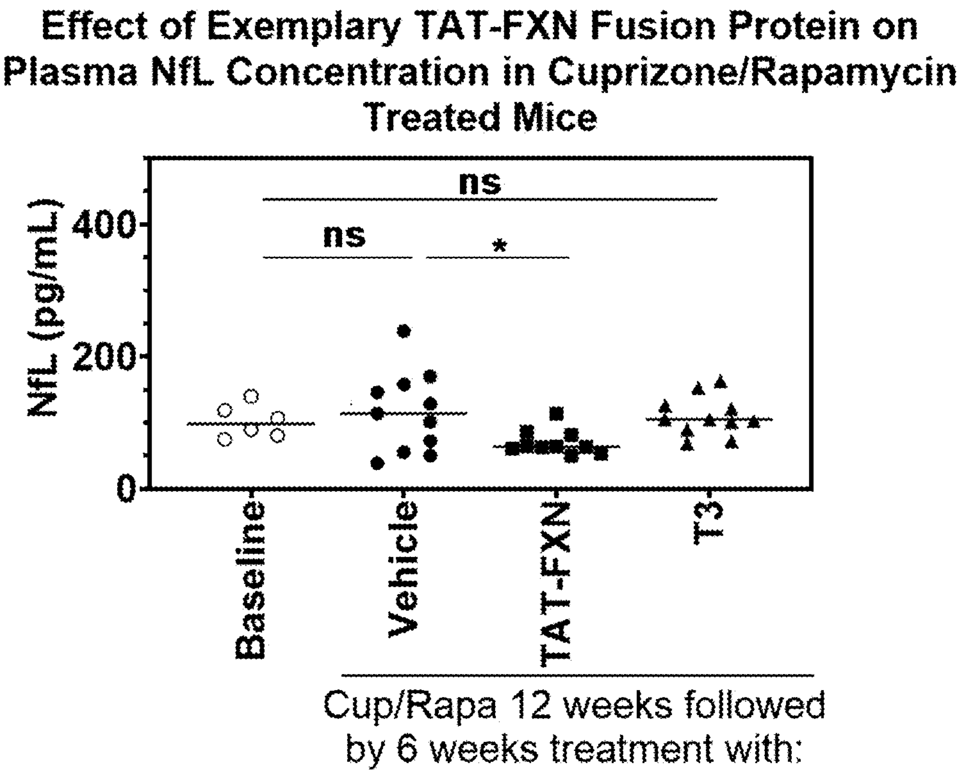

FIG. 6, panel A is a dot plot showing plasma levels of pNfH in cuprizone/rapamycin treated mouse model of demyelination following treatment with vehicle (as a negative control), T3 (as a positive control) and the exemplary TAT-hFXN fusion protein. FIG. 6, panel B is a dot plot showing plasma levels of NfL in cuprizone/rapamycin treated mouse model of demyelination following treatment with vehicle, T3 and the exemplary TAT-hFXN fusion protein.

The results shown in FIG. 6, panels A and B, demonstrate that a 6-week treatment with the exemplary TAT-hFXN fusion protein results in a statistically significant decrease in the levels of NfL and pNfH in cuprizone/rapamycin treated mice. These results indicate that treatment with a frataxin replacement therapeutic compound, such as the exemplary TAT-hFXN fusion protein, may decrease neurodegeneration in a subject with a myelin associated disease.

Example 10. FSGMs are Upregulated During Oligodendrocyte Differentiation In Vitro The goal of this experiment was to explore the mechanistic connection between myelination and FXN-sensitive genomic markers (FSGMs) described in Example 1. To this end, levels of FSGMs in undifferentiated and differentiated oligodendrocytes were determined. Oligodendrocytes are responsible for myelin deposition in layer around axons in the CNS myelination.

For the experiment, an immortalized immature human oligodendrocyte cell line MO3.13 (CELLutions Biosystems, Inc.) was used. The cells were seeded onto 10 cm plates at 250,000 cells/plate in complete DMEM (ThermoFisher 11995065), 10% FBS and 1% antibiotic/antimycotic, and grown at 37° C. in 5% $CO_2$. After 24 hours, the cells from one plate (undifferentiated) were collected, while the cells in the second plate were induced to undergo differentiation by replacing the growth media with differentiation media (DMEM, ThermoFisher 11995065) and 1% antibiotic/antimycotic. The absence of FBS induces differentiation in these cells. The cells were allowed to grow in the differentiation media for 7 days, with fresh media added every 2-3 days. After 7 days, the differentiated cells were harvested. The expression levels of oligodendrocyte differentiation markers and selected FSGMs was determined by qPCR using standard methods.

Figure 7:
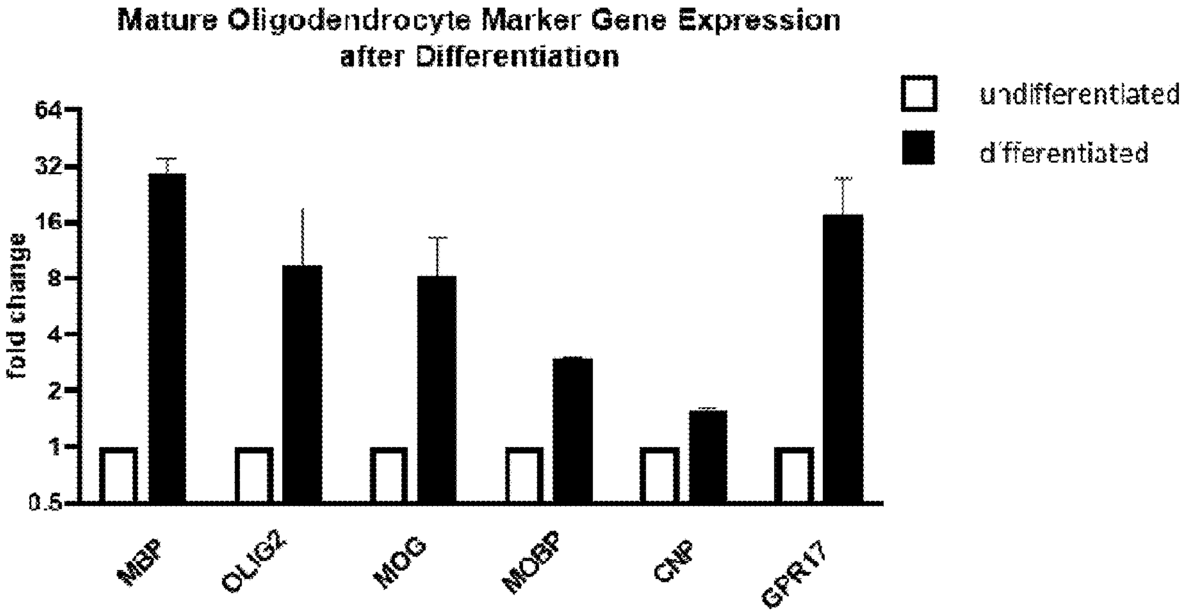
FIG. 7, panel A is a bar graph showing relative expression levels of certain oligodendrocyte differentiation markers in the oligodendrocytes before and after differentiation.
Figure 7:
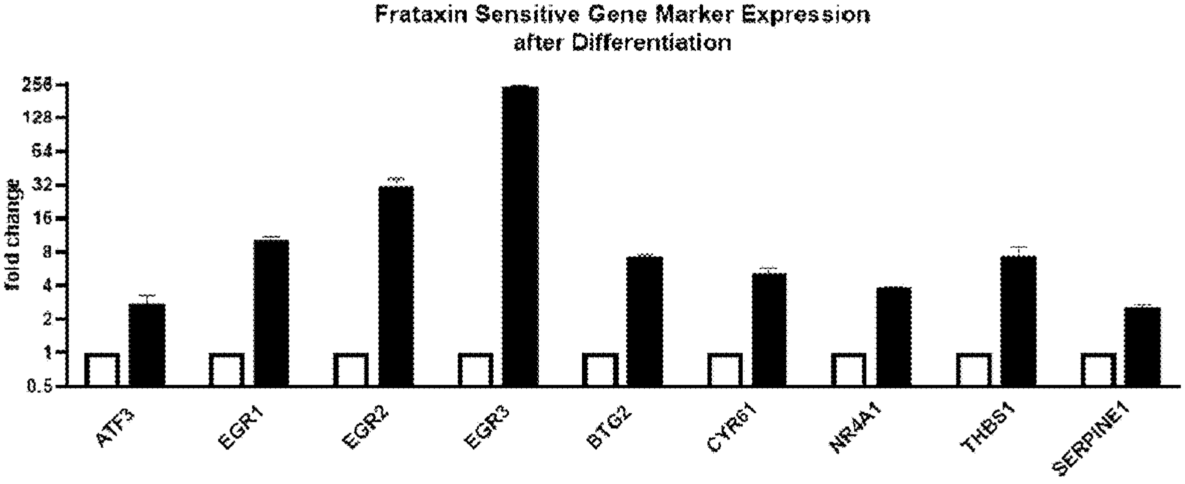

FIG. 7, panel A is a bar graph showing relative expression levels of certain oligodendrocyte differentiation markers in the oligodendrocytes before and after differentiation. The results presented in FIG. 7, Panel A demonstrate that relative levels of oligodendrocyte differentiation markers increased following differentiation, indicating differentiation of oligodendrocytes in the experiment.

FIG. 7, panel B is bar graph showing relative expression levels of certain FSGMS in differentiated and undifferentiated oligodendrocytes. The results presented in FIG. 7, panel B demonstrate a significant increase in the relative levels of certain FSGMs in oligodendrocytes after differentiation. These results demonstrate a concomitant regulation of oligodendrocyte differentiation gene markers and FSGMs during oligodendrocyte differentiation.

Example 11. Oligodendrocyte Differentiation Markers and FSGMs are Upregulated in Oligodendrocytes Treated with a Frataxin Replacement Therapeutic Compound The goal of this experiment was to determine if treatment of immature oligodendrocytes with a frataxin replacement therapeutic compound, such as the exemplary TAT-hFXN fusion protein, could be used to induce oligodendrocyte differentiation instead of FBS removal as used in Example 10. Specifically, the goal of this experiment was to determine whether treatment with the exemplary TAT-hFXN fusion protein has an effect on the expression levels of oligodendrocyte differentiation markers concomitantly with FXN-sensitive genomic markers (FSGMs), as observed in Example 10. To this end, expression levels of mature oligodendrocyte markers and FSGMs were quantified in cultured mature oligodendrocytes after treatment with the exemplary TAT-hFXN fusion protein.

For the experiment, an immortalized immature human oligodendrocyte cell line MO3.13 (CELLutions Biosystems, Inc.) was used. The cells were seeded onto 10 cm plates at 400,000 cells/plate in complete DMEM (ThermoFisher 11995065), 10% FBS and 1% antibiotic/antimycotic, and grown at 37° C. in 5% $CO_2$. After 24 hours, the cells were washed twice with PBS, and then treated with 20 μM exemplary TAT-hFXN fusion protein or vehicle in 5 mL transduction media (DMEM, 1% heat inactivated FBS, 1% antibiotic/antimycotic, 20 mM glycerol) for 3 hours. Subsequently, 5 mL of complete media was added, and the cells were incubated overnight. The following day, media was removed, the cells were treated with the exemplary TAT-hFXN fusion protein or vehicle as described above, and incubated overnight. Subsequently, the expression levels of mature oligodendrocyte markers and selected FSGMs was determined by qPCR using standard methods.

Figure 8:
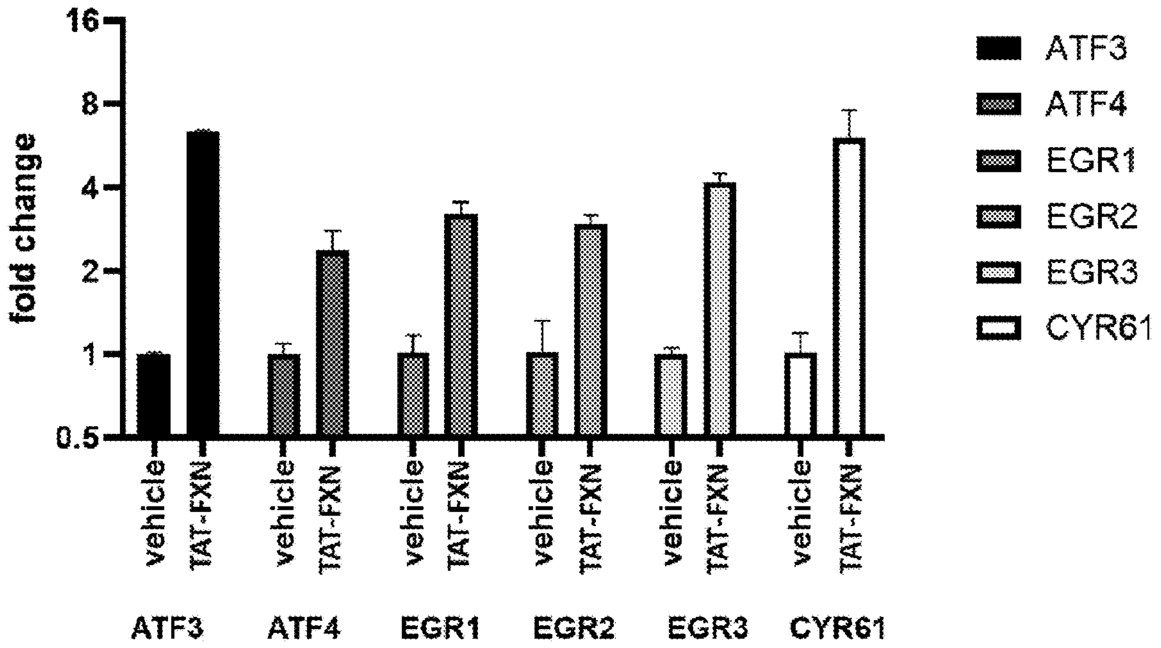
FIG. 8, panel A is bar graph showing relative expression levels of certain FSGMS in mature oligodendrocytes after treatment with vehicle or 20 μM exemplary TAT-hFXN fusion protein.
Figure 8:
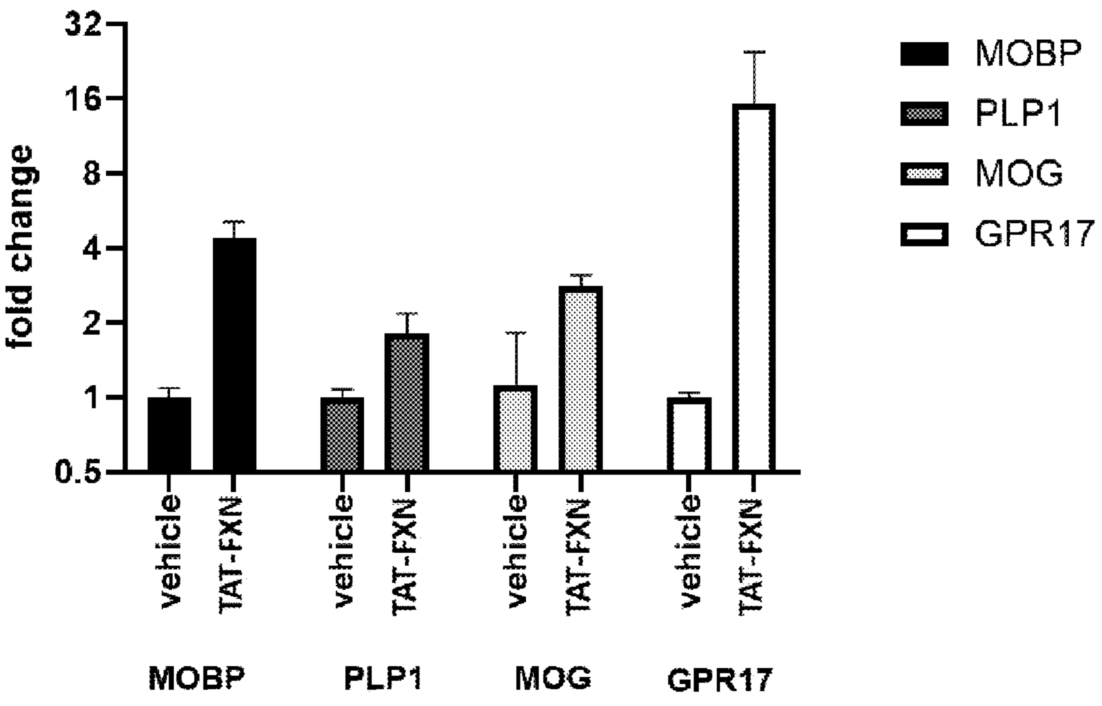

FIG. 8, panel A is bar graph showing relative expression levels of certain FSGMs in oligodendrocytes after treatment with vehicle or 20 μM exemplary TAT-hFXN fusion protein. The measurements of FSGMs were conducted as a control measure to demonstrate that the exemplary TAT-hFXN can enter the oligodendrocytes and modulate FSGMs in a manner consistent with oligodendrocyte differentiation as determined in Example 10 (see FIG. 7, Panel B). The results presented in FIG. 8, panel B demonstrate that treatment with 20 μM exemplary TAT-hFXN fusion protein causes an increase in the relative levels of FSGMS in mature oligodendrocytes in the same manner as in Example 10. These results indicate that treatment of oligodendrocytes with the exemplary TAT-hFXN fusion protein can induce oligodendrocyte maturation.

FIG. 8, panel B is a bar graph showing relative expression levels in mature oligodendrocytes of certain mature oligodendrocyte gene markers after treatment with vehicle or 20 μM exemplary TAT-hFXN fusion protein. The results presented in FIG. 8, Panel B demonstrate that treatment with 20 μM exemplary TAT-hFXN fusion protein causes an increase in the relative levels of mature oligodendrocyte gene markers. These results indicate that treatment of oligodendrocytes with a frataxin replacement therapeutic compound induces oligodendrocyte maturation and may increase myelination by oligodendrocytes.

Example 12. Myelin-Related Markers and FSGMs are Upregulated in Schwann Cells Treated with a Frataxin Replacement Therapeutic Compound The goal of this experiment was to determine if treatment of Schwann cells with a frataxin replacement therapeutic compound, such as the exemplary TAT-hFXN fusion protein, may have an effect on the expression levels of myelin-related markers and FXN-sensitive genomic markers (FSGMs). Schwann cells are responsible for myelin deposition in the peripheral nervous system (PNS).

In the experiment, the expression levels of Schwann cell markers and FSGMs were quantified in cultured Schwann cells after treatment with the exemplary TAT-hFXN fusion protein. To this end, immortalized Schwann cells (ATCC CRL-3391) were seeded onto 10 cm plates at 750,000 cells/plate in complete DMEM (ThermoFisher 11995065), 10% FBS and 1% antibiotic/antimycotic, and grown at 37° C. in 5% $CO_2$. After 24 hours, the cells were washed twice with PBS, and then treated with 20 μM exemplary TAT-hFXN fusion protein or vehicle in 5 mL transduction media (DMEM, 1% heat inactivated FBS, 1% antibiotic/antimycotic, 20 mM glycerol) for 3 hours. Subsequently, 5 mL of complete media was added, and the cells were incubated overnight. The following day, media was removed, the cells were treated with the exemplary TAT-hFXN fusion protein or vehicle as described above, and incubated overnight. Subsequently, the expression levels of myelin-related gene markers and selected FSGMs was determined by qPCR using standard methods.

Figure 9:
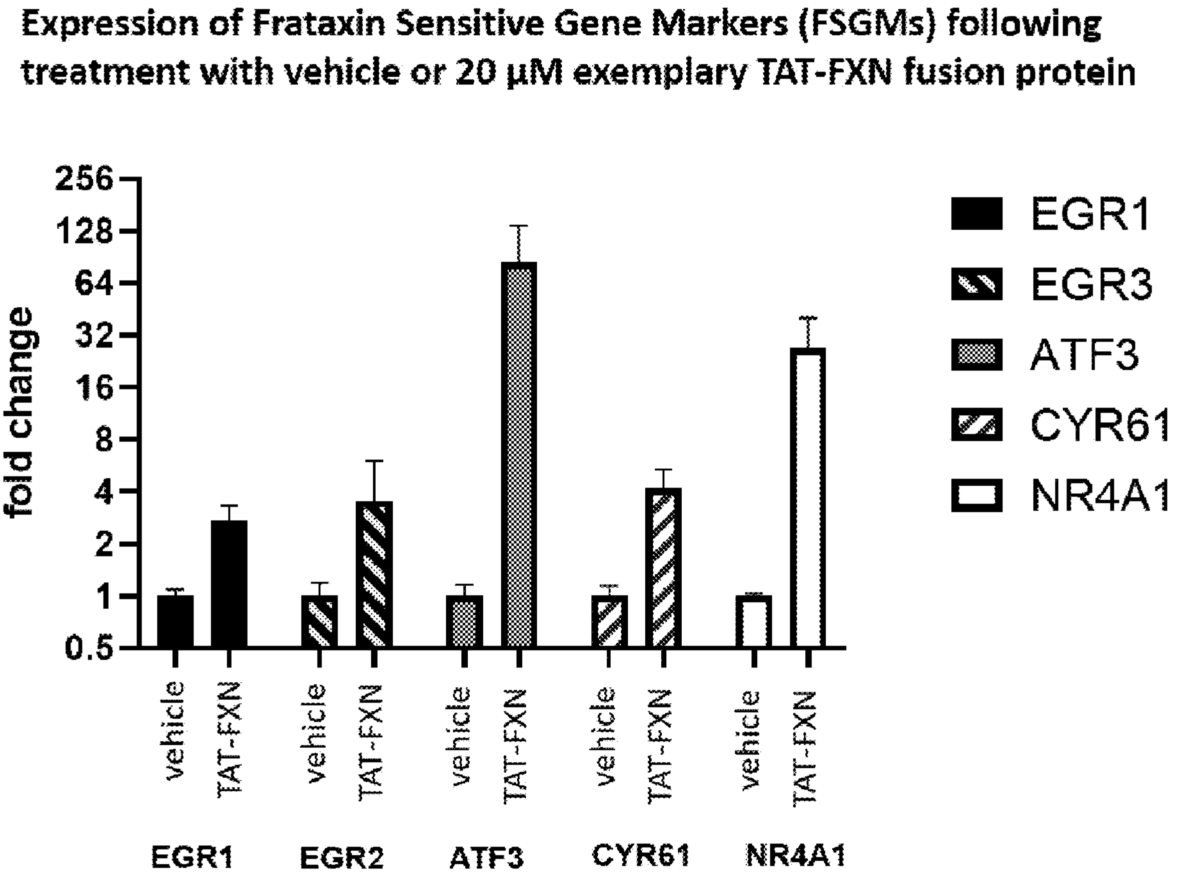
FIG. 9, panel A is bar graph showing relative expression levels of certain FSGMS in Schwann cells after treatment with vehicle or 20 μM exemplary TAT-hFXN fusion protein.
Figure 9:
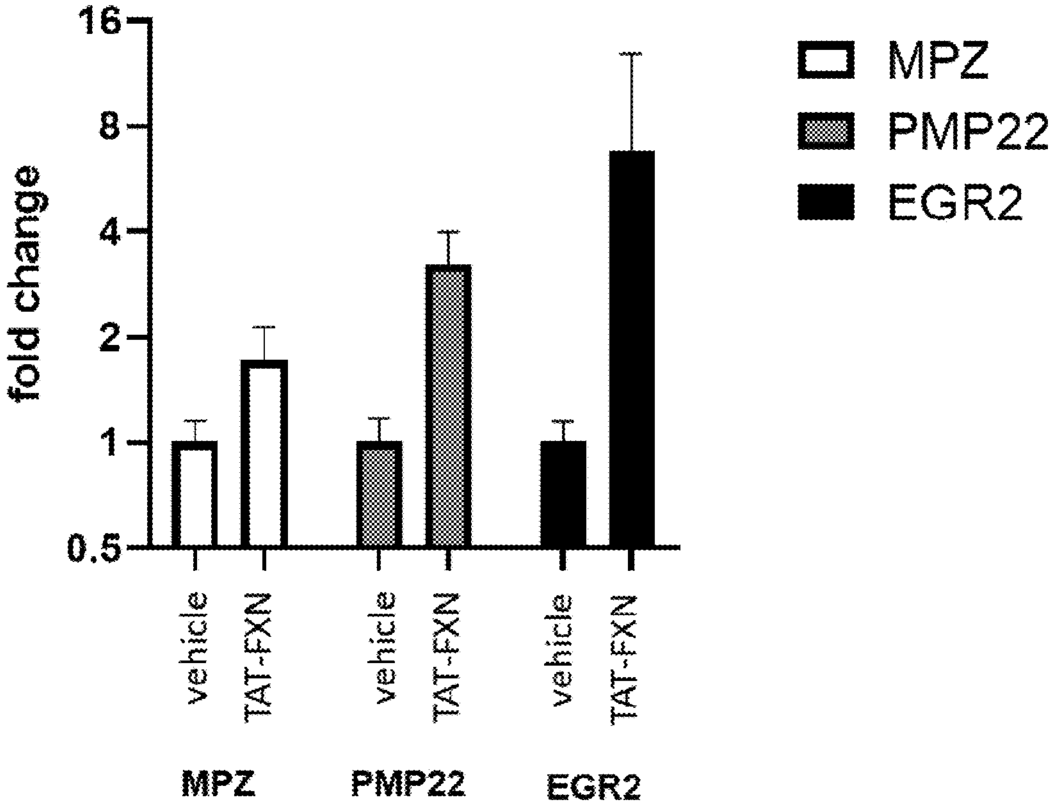

FIG. 9, panel A is bar graph showing relative expression levels of certain FSGMS in Schwann cells after treatment with vehicle or 20 μM exemplary TAT-hFXN fusion protein. The results presented in FIG. 9, panel A demonstrate that treatment with 20 μM exemplary TAT-hFXN fusion protein causes an increase in the relative levels of FSGMs in Schwann cells, and this effect is similar to the effect seen in oligodendrocytes described in Example 11 (see FIG. 8, panel A). These results indicate the presence of a possible regulatory connection between FXN and myelination of the peripheral nervous system.

FIG. 9, panel B is a bar graph showing relative expression levels in Schwann cells of certain Schwann cells gene markers after treatment with vehicle or 20 μM exemplary TAT-hFXN fusion protein. The results presented in FIG. 9, Panel B demonstrate that treatment with 20 μM exemplary TAT-hFXN fusion protein causes an increase in the relative levels of myelin-related gene markers. Specifically, treatment with the exemplary TAT-hFXN fusion protein caused an increase in expression levels of PMP22 and MPZ genes, both of which encode structural components of myelin. These results indicate that treatment of Schwann cells with a frataxin replacement therapeutic compound may increase myelination by Schwann cells. These results also indicate that administration a frataxin replacement therapeutic compound, such as the exemplary TAT-hFXN fusion protein, may be effective for the treatment of a myelin associated disease that is associated with myelination defects in the peripheral nervous system, e.g., CMT.

Example 13. Frataxin Replacement Therapeutic Compound Comprising TES Modulates FSGM Levels in Oligodendrocytes The goal of this experiment was to test the ability of various frataxin replacement therapeutic compound comprising TES to affect FSGM levels in undifferentiated oligodendrocytes. The experiment utilized ATF3 as FSGM, as this marker was previously shown to increase in response to treatment with the exemplary TAT-hFXN fusion protein (see FIG. 8, Panel B). The experiment also utilized three frataxin replacement therapeutic compounds: TAT-Calp-hFXN (SEQ ID NO: 54); TAT-Ub-hFX (SEQ ID NO: 52) and TAT-hFXN NES (SEQ ID NO: 56).

Immortalized immature human oligodendrocytes (MO3.13, CELLutions Biosystems, Inc.) were seeded onto 10 cm plates at 400,000 cells/plate in complete media that included DMEM (ThermoFisher 11995065), 10% FBS and 1% antibiotic/antimycotic. The cells were grown at 37° C. in 5% $CO_2$ for 24 hours. Subsequently, the cells were washed twice with PBS and then treated with TAT-Calp-hFXN at 0.25 μM, 0.5 μM and 1 μM; TAT-Ub-hFXN at 0.25 μM, 0.5 μM and 1 μM; and TAT-hFXN-NES at 0.125 μM, 0.25 μM or 0.5 μM or vehicle. The treatment was conducted by adding to each plate 5 mL transduction media containing DMEM, 1% heat inactivated FBS, 1% antibiotic/antimycotic and 20 mM glycerol. The cells were incubated with the frataxin replacement therapeutic compounds for 3 hours, and 5 mL of complete media was added, and the cells were inducated overnight. The next day, the cell media was removed, and the cells were once again treated with the frataxin replacement therapeutic compounds as described above. After an overnight incubation, the cells were collected, subjected to RNA isolation, and the levels of ATF3 expression were determined by qPCR using standard procedures.

Figure 10:
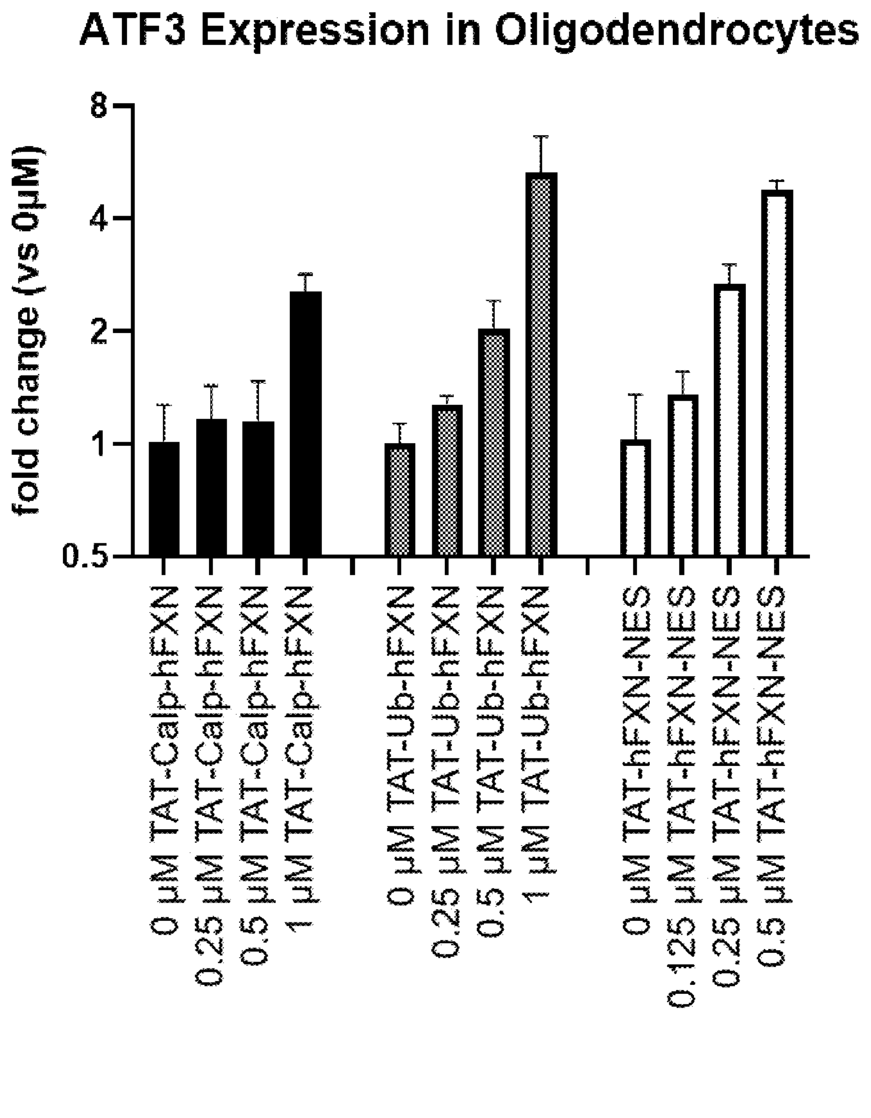
FIG. 10 is a bar graph showing the expression levels of ATF3 in immature oligodendrocytes after treatment with vehicle or TAT-Calp-hFXN at 0.25 μM, 0.5 μM and 1 μM; TAT-Ub-hFXN at 0.25 μM, 0.5 μM and 1 μM; and TAT-hFXN-NES at 0.125 μM, 0.25 μM or 0.5 μM.

The results of the experiment are shown in FIG. 10. Specifically, FIG. 10 is a bar graph showing the expression levels of ATF3 in immature oligodendrocytes after treatment with vehicle or TAT-Calp-hFXN at 0.25 μM, 0.5 μM and 1 μM; TAT-Ub-hFXN at 0.25 μM, 0.5 μM and 1 μM; and TAT-hFXN-NES at 0.125 μM, 0.25 μM or 0.5 μM. The results shown in FIG. 10 demonstrate that treatment of oligodendrocytes with all three tested frataxin replacement therapeutic compounds results in a dose-dependent increase in the levels of ATF3.

Example 14: Testing the Ability of a Frataxin Replacement Therapeutic Compound to Affect Myelination in a Mouse Model of Demyelination The goal of this experiment is to test the ability of a frataxin replacement therapeutic compound, e.g., the exemplary TAT-hFXN fusion protein or frataxin replacement therapeutic compounds comprising TES, to affect myelination in a mouse model of demyelination. To this end, mice are fed with cuprizone and treated with rapamycin for 12 weeks to induce demyelination as described in Example 9. Subsequently, mice are treated with the exemplary TAT-hFXN fusion protein and/or or frataxin replacement therapeutic compounds comprising TES, such as frataxin fusion proteins of SEQ ID NOS. 52, 54 and 56, or vehicle control for 3 weeks or 6 weeks. Myelination in the treated mice is assessed by determining the expression of PLP, Iba1, CD44 and GFAP in the cortex, hippocampus and corpus callosum using immunohistochemistry.

The amount of myelination in mice treated with the exemplary TAT-hFXN fusion protein and/or frataxin replacement therapeutic compounds comprising TES will be compared to the amount of myelination in mice treated with vehicle. It is expected that the amount of myelination in mice treated with the exemplary TAT-hFXN fusion protein and/or frataxin replacement therapeutic compounds comprising TES will be higher than the amount of myelination in mice treated with vehicle.

Example 15: Testing the Ability of a Frataxin Replacement Therapeutic Compound to Affect Myelination in a Mouse Model of Demyelination The goal of this experiment is to test the ability of a frataxin replacement therapeutic compound, e.g., the exemplary TAT-hFXN fusion protein or frataxin replacement therapeutic compounds comprising TES, to affect myelination in a mouse model of demyelination. This experiment utilizes the Ndufs4 KO mouse model of myelination and Leigh Syndrome. The mice are treated with the exemplary TAT-hFXN fusion protein and/or frataxin replacement therapeutic compounds comprising TES, such as frataxin fusion proteins of SEQ ID NOS. 52, 54 and 56, or vehicle control for 3 weeks or 6 weeks. Myelination in the treated mice is assessed by determining the amount and/or distribution of myelination markers in the brain by using myelin staining, including, e.g., Luxol Fast Blue or paraphenylenediamine (PPD), as well as immunohistochemistry and, specifically, myelin proteolipid protein (PLP) staining. The amount myelination in mice treated with the exemplary TAT-hFXN fusion protein and/or frataxin replacement therapeutic compounds comprising TES will be compared to the amount of myelination in mice treated with vehicle. It is expected that the amount of myelination in mice treated with the exemplary TAT-hFXN fusion protein and/or frataxin replacement therapeutic compounds comprising TES will be higher than the amount of myelination in mice treated with vehicle.

What is claimed is:

1. A method of treating a myelin associated disease, said method comprising administering to a subject in need thereof an effective amount of a frataxin (FXN) fusion protein, such that said myelin associated disease in said subject is treated;

wherein said FXN fusion protein consists of SEQ ID NO: 22; and wherein said myelin associated disease is not Friedreich's Ataxia and Leigh Syndrome, French Canadian Type (LSFC).

2. The method of claim 1, wherein administration of the FXN fusion protein causes modulation of at least one protein in said subject, wherein said at least one protein is selected from the group consisting of ABCE1, EIF1A, EGR 1, EGR2 (KROX20), EGR3, SERPINE1, CCN1 (CYR61), THBS1, NR41(Nurr77), RTN4 (NOGO), RTN4IP1 and TMEM126A.

3. The method of claim 1, wherein said myelin associated disease is a dysmyelination disease characterized by a malformed and/or defective myelin sheath present in the subject.

4. The method of claim 3, wherein said dysmyelination disease is a leukodystrophy.

5. The method of claim 4, wherein said leukodystrophy is selected from the group consisting of Vanishing White Matter Disease (VWMD) and X-Linked adrenoleukodystrophy (ALD).

6. The method of claim 1, wherein said myelin associated disease is a demyelination disease characterized by the destruction of previously normal myelin in the subject.

7. The method of claim 6, wherein said demyelination disease is a central demyelination disease.

8. The method of claim 7, wherein said central demyelination disease is an inflammatory or an immune central demyelination disease.

9. The method of claim 8, wherein said inflammatory or said immune central demyelination disease is selected from the group consisting of multiple sclerosis (MS), myelinoclastic diffuse sclerosis (Schilder's Disease), optic neuritis, acute disseminated encephalomyelitis (ADEM), acute hemorrhagic leucoencephalitis (AHL), paraneoplastic encephalomyelitis, rheumatoid arthritis, systemic lupus erythematosus, Behçet's disease and Sjörgen disease.

10. The method of claim 7, wherein said central demyelination disease is a toxic or metabolic central demyelination disease.

11. The method of claim 10, wherein said toxic or metabolic central demyelination disease is selected from the group consisting of: a disorder associated with a vitamin B12 deficiency; central pontine myelinolysis; and posterior reversible encephalopathy syndrome (PRES).

12. The method of claim 6, wherein said demyelination disease is a peripheral demyelination disease.

13. The method of claim 12, wherein said peripheral demyelination disease is selected from the group consisting of: Guillain-Barré Syndrome, chronic inflammatory demyelinating polyradiculoneuropathy (CIDP), paraproteinemic demyelinating neuropathy, progressive inflammatory neuropathy (PIN), Anti-Myelin Associated Glycoprotein (MAG) neuropathy, POEMS Syndrome, Charcot Marie Tooth Disease, and a copper deficiency associated disorder.

14. The method of claim 1, wherein at least one symptom of the myelin associated disease is alleviated in the subject, wherein said at least one symptom is selected from the group consisting of ataxia, blurred vision, muscle weakness, muscle stiffness, muscle spasms, heart palpitations, dizziness, uncoordinated movements, and fatigue.

15. The method of claim 1, wherein said subject is a human.

16. A method of increasing the amount of myelin in a subject with a myelin associated disease, said method comprising administering to said subject an effective amount of a frataxin (FXN) fusion protein, such that the amount of myelin in said subject is increased;

wherein said FXN fusion protein consists of SEQ ID NO: 22; and wherein said myelin associated disease is not Friedreich's Ataxia and Leigh Syndrome, French Canadian Type (LSFC).

17. A method of promoting oligodendrocyte maturation in a subject with a myelin associated disease, said method comprising administering to said subject an effective amount of a frataxin (FXN) fusion protein, such that oligodendrocyte maturation in said subject is increased;

wherein said FXN fusion protein consists of SEQ ID NO: 22; and wherein said myelin associated disease is not Friedreich's Ataxia and Leigh Syndrome, French Canadian Type (LSFC).

* * * * *

SEQUENCE LISTING

```
Sequence total quantity: 57
SEQ ID NO: 1            moltype = AA  length = 210
FEATURE                 Location/Qualifiers
source                  1..210
                        mol_type = protein
                        organism = Homo sapiens
SEQUENCE: 1
MWTLGRRAVA GLLASPSPAQ AQTLTRVPRP AELAPLCGRR GLRTDIDATC TPRRASSNQR  60
GLNQIWNVKK QSVYLMNLRK SGTLGHPGSL DETTYERLAE ETLDSLAEFF EDLADKPYTF  120
EDYDVSFGSG VLTVKLGGDL GTYVINKQTP NKQIWLSSPS SGPKRYDWTG KNWVYSHDGV  180
SLHELLAAEL TKALKTKLDL SSLAYSGKDA                                   210

SEQ ID NO: 2            moltype = AA  length = 130
FEATURE                 Location/Qualifiers
source                  1..130
                        mol_type = protein
                        organism = Homo sapiens
SEQUENCE: 2
SGTLGHPGSL DETTYERLAE ETLDSLAEFF EDLADKPYTF EDYDVSFGSG VLTVKLGGDL  60
GTYVINKQTP NKQIWLSSPS SGPKRYDWTG KNWVYSHDGV SLHELLAAEL TKALKTKLDL  120
SSLAYSGKDA                                                         130

SEQ ID NO: 3            moltype = AA  length = 11
FEATURE                 Location/Qualifiers
source                  1..11
                        mol_type = protein
                        organism = Human immunodeficiency virus
SEQUENCE: 3
YGRKKRRQRR R                                                       11

SEQ ID NO: 4            moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 4
MYGRKKRRQR RR                                                      12
```

```
SEQ ID NO: 5            moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 5
GWTLNSAGYL LGPHAVGNHR SFSDKNGLTS                                      30

SEQ ID NO: 6            moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 6
INLKALAALA KKIL                                                       14

SEQ ID NO: 7            moltype = AA  length = 27
FEATURE                 Location/Qualifiers
REGION                  1..27
                        note = Description of Artificial Sequence: Synthetic peptide
source                  1..27
                        mol_type = protein
                        organism = synthetic construct
SEQUENCE: 7
GWTLNSAGYL LGKINLKALA ALAKKIL                                         27

SEQ ID NO: 8            moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 8
RQIKIWFQNR RMKWKK                                                     16

SEQ ID NO: 9            moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 9
RRRRRRRRR                                                             9

SEQ ID NO: 10           moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 10
DAATATRGRS AASRPTERPR APARSASRPR RPVE                                 34

SEQ ID NO: 11           moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 11
GGGGSLVPRG SGGGGS                                                     16

SEQ ID NO: 12           moltype = AA  length = 6
FEATURE                 Location/Qualifiers
REGION                  1..6
                        note = Description of Artificial Sequence: Synthetic peptide
source                  1..6
                        mol_type = protein
```

```
                          organism = synthetic construct
SEQUENCE: 12
GSGSGS                                                                 6

SEQ ID NO: 13             moltype = AA  length = 8
FEATURE                   Location/Qualifiers
REGION                    1..8
                          note = Description of Artificial Sequence: Synthetic peptide
source                    1..8
                          mol_type = protein
                          organism = synthetic construct
SEQUENCE: 13
GSGSGSGS                                                               8

SEQ ID NO: 14             moltype = AA  length = 11
FEATURE                   Location/Qualifiers
REGION                    1..11
                          note = Description of Artificial Sequence: Synthetic peptide
source                    1..11
                          mol_type = protein
                          organism = synthetic construct
SEQUENCE: 14
GGSGGHMGSG G                                                           11

SEQ ID NO: 15             moltype = AA  length = 11
FEATURE                   Location/Qualifiers
REGION                    1..11
                          note = Description of Artificial Sequence: Synthetic peptide
source                    1..11
                          mol_type = protein
                          organism = synthetic construct
SEQUENCE: 15
GGSGGSGGSG G                                                           11

SEQ ID NO: 16             moltype = AA  length = 5
FEATURE                   Location/Qualifiers
REGION                    1..5
                          note = Description of Artificial Sequence: Synthetic peptide
source                    1..5
                          mol_type = protein
                          organism = synthetic construct
SEQUENCE: 16
GGSGG                                                                  5

SEQ ID NO: 17             moltype = AA  length = 18
FEATURE                   Location/Qualifiers
REGION                    1..18
                          note = Description of Artificial Sequence: Synthetic peptide
source                    1..18
                          mol_type = protein
                          organism = synthetic construct
SEQUENCE: 17
GGGSEGGGSE GGGSEGGG                                                    18

SEQ ID NO: 18             moltype = AA  length = 8
FEATURE                   Location/Qualifiers
REGION                    1..8
                          note = Description of Artificial Sequence: Synthetic peptide
source                    1..8
                          mol_type = protein
                          organism = synthetic construct
SEQUENCE: 18
AAGAATAA                                                               8

SEQ ID NO: 19             moltype = AA  length = 5
FEATURE                   Location/Qualifiers
REGION                    1..5
                          note = Description of Artificial Sequence: Synthetic peptide
source                    1..5
                          mol_type = protein
                          organism = synthetic construct
SEQUENCE: 19
GGGGG                                                                  5

SEQ ID NO: 20             moltype = AA  length = 5
FEATURE                   Location/Qualifiers
REGION                    1..5
                          note = Description of Artificial Sequence: Synthetic peptide
source                    1..5
```

```
                        mol_type = protein
                        organism = synthetic construct
SEQUENCE: 20
GGSSG                                                                5

SEQ ID NO: 21           moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 21
GSGGGTGGGS G                                                         11

SEQ ID NO: 22           moltype = AA  length = 224
FEATURE                 Location/Qualifiers
REGION                  1..224
                        note = Description of Artificial Sequence: Synthetic
                         polypeptide
source                  1..224
                        mol_type = protein
                        organism = synthetic construct
SEQUENCE: 22
MYGRKKRRQR RRGGMWTLGR RAVAGLLASP SPAQAQTLTR VPRPAELAPL CGRRGLRTDI  60
DATCTPRRAS SNQRGLNQIW NVKKQSVYLM NLRKSGTLGH PGSLDETTYE RLAEETLDSL  120
AEFFEDLADK PYTFEDYDVS FGSGVLTVKL GGDLGTYVIN KQTPNKQIWL SSPSSGPKRY  180
DWTGKNWVYS HDGVSLHELL AAELTKALKT KLDLSSLAYS GKDA                     224

SEQ ID NO: 23           moltype = AA  length = 76
FEATURE                 Location/Qualifiers
source                  1..76
                        mol_type = protein
                        organism = Homo sapiens
SEQUENCE: 23
MQIFVKTLTG KTITLEVEPS DTIENVKAKI QDKEGIPPDQ QRLIFAGKQL EDGRTLSDYN  60
IQKESTLHLV LRLRGG                                                    76

SEQ ID NO: 24           moltype = AA  length = 4
FEATURE                 Location/Qualifiers
REGION                  1..4
                        note = Description of Unknown: Caspase cleavage domain
                         sequence
source                  1..4
                        mol_type = protein
                        organism = unidentified
SEQUENCE: 24
DEVD                                                                 4

SEQ ID NO: 25           moltype = AA  length = 8
FEATURE                 Location/Qualifiers
REGION                  1..8
                        note = Description of Unknown: Calpain cleavage domain
                         sequence
source                  1..8
                        mol_type = protein
                        organism = unidentified
SEQUENCE: 25
EPLFAERK                                                             8

SEQ ID NO: 26           moltype = AA  length = 4
FEATURE                 Location/Qualifiers
REGION                  1..4
                        note = Description of Unknown: Calpain cleavage domain
                         sequence
source                  1..4
                        mol_type = protein
                        organism = unidentified
SEQUENCE: 26
LLVY                                                                 4

SEQ ID NO: 27           moltype = AA  length = 5
FEATURE                 Location/Qualifiers
REGION                  1..5
                        note = Description of Unknown: Enterokinase (light
                         chain)/Enteropeptidase cleavage site sequence
source                  1..5
                        mol_type = protein
                        organism = unidentified
```

```
SEQUENCE: 27
DDDDK                                                                5

SEQ ID NO: 28           moltype = AA  length = 7
FEATURE                 Location/Qualifiers
REGION                  1..7
                        note = Description of Unknown: PreScission Protease/human
                         Rhinovirus protease (HRV 3C) cleavage site sequence
source                  1..7
                        mol_type = protein
                        organism = unidentified
SEQUENCE: 28
LEVLFQP                                                              7

SEQ ID NO: 29           moltype = AA  length = 7
FEATURE                 Location/Qualifiers
REGION                  1..7
                        note = Description of Unknown: TEV protease cleavage site
                         sequence
source                  1..7
                        mol_type = protein
                        organism = unidentified
SEQUENCE: 29
LEVLFGP                                                              7

SEQ ID NO: 30           moltype = AA  length = 7
FEATURE                 Location/Qualifiers
REGION                  1..7
                        note = Description of Unknown: TEV protease cleavage site
                         sequence
source                  1..7
                        mol_type = protein
                        organism = unidentified
SEQUENCE: 30
ENLYFQS                                                              7

SEQ ID NO: 31           moltype = AA  length = 7
FEATURE                 Location/Qualifiers
REGION                  1..7
                        note = Description of Artificial Sequence: Synthetic peptide
VARIANT                 2..3
                        note = Any amino acid
VARIANT                 5
                        note = Any amino acid
source                  1..7
                        mol_type = protein
                        organism = synthetic construct
SEQUENCE: 31
EXXYXQG                                                              7

SEQ ID NO: 32           moltype = AA  length = 7
FEATURE                 Location/Qualifiers
REGION                  1..7
                        note = Description of Artificial Sequence: Synthetic peptide
VARIANT                 2..3
                        note = Any amino acid
VARIANT                 5
                        note = Any amino acid
source                  1..7
                        mol_type = protein
                        organism = synthetic construct
SEQUENCE: 32
EXXYXQS                                                              7

SEQ ID NO: 33           moltype = AA  length = 7
FEATURE                 Location/Qualifiers
REGION                  1..7
                        note = Description of Unknown: TVMV protease cleavage site
                         sequence
source                  1..7
                        mol_type = protein
                        organism = unidentified
SEQUENCE: 33
ETVRFQS                                                              7

SEQ ID NO: 34           moltype = AA  length = 4
FEATURE                 Location/Qualifiers
REGION                  1..4
                        note = Description of Unknown: Factor Xa protease cleavage
```

```
                     site sequence
source               1..4
                     mol_type = protein
                     organism = unidentified
SEQUENCE: 34
IEGR                                                          4

SEQ ID NO: 35        moltype = AA  length = 4
FEATURE              Location/Qualifiers
REGION               1..4
                     note = Description of Unknown: Factor Xa protease cleavage
                      site sequence
source               1..4
                     mol_type = protein
                     organism = unidentified
SEQUENCE: 35
IDGR                                                          4

SEQ ID NO: 36        moltype = AA  length = 5
FEATURE              Location/Qualifiers
REGION               1..5
                     note = Description of Unknown: Thrombin cleavage site
                      sequence
source               1..5
                     mol_type = protein
                     organism = unidentified
SEQUENCE: 36
LVPRS                                                         5

SEQ ID NO: 37        moltype = AA  length = 5
FEATURE              Location/Qualifiers
REGION               1..5
                     note = Description of Unknown: Thrombin cleavage site
                      sequence
source               1..5
                     mol_type = protein
                     organism = unidentified
SEQUENCE: 37
LVPGS                                                         5

SEQ ID NO: 38        moltype = AA  length = 97
FEATURE              Location/Qualifiers
REGION               1..97
                     note = Description of Unknown: SUMO1 sequence
source               1..97
                     mol_type = protein
                     organism = unidentified
SEQUENCE: 38
MSDQEAKPST EDLGDKKEGE YIKLKVIGQD SSEIHFKVKM TTHLKKLKES YCQRQGVPMN  60
SLRFLFEGQR IADNHTPKEL GMEEEDVIEV YQEQTGG                          97

SEQ ID NO: 39        moltype = AA  length = 95
FEATURE              Location/Qualifiers
REGION               1..95
                     note = Description of Unknown: SUMO2 sequence
source               1..95
                     mol_type = protein
                     organism = unidentified
SEQUENCE: 39
MADEKPKEGV KTENNDHINL KVAGQDGSVV QFKIKRHTPL SKLMKAYCER QGLSMRQIRF  60
RFDGQPINET DTPAQLEMED EDTIDVFQQQ TGGVY                            95

SEQ ID NO: 40        moltype = AA  length = 103
FEATURE              Location/Qualifiers
REGION               1..103
                     note = Description of Unknown: SUMO3 sequence
source               1..103
                     mol_type = protein
                     organism = unidentified
SEQUENCE: 40
MSEEKPKEGV KTENDHINLK VAGQDGSVVQ FKIKRHTPLS KLMKAYCERQ GLSMRQIRFR  60
FDGQPINETD TPAQLEMEDE DTIDVFQQQT GGVPESSLAG HSF                   103

SEQ ID NO: 41        moltype = AA  length = 95
FEATURE              Location/Qualifiers
REGION               1..95
                     note = Description of Unknown: SUMO4 sequence
source               1..95
                     mol_type = protein
```

```
                       organism = unidentified
SEQUENCE: 41
MANEKPTEEV KTENNNHINL KVAGQDGSVV QFKIKRQTPL SKLMKAYCEP RGLSMKQIRF  60
RFGGQPISGT DKPAQLEMED EDTIDVFQQP TGGVY                             95

SEQ ID NO: 42          moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 42
LALKLAGLDL                                                         10

SEQ ID NO: 43          moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 43
LQKKLEELEL                                                         10

SEQ ID NO: 44          moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 44
MQELSNILNL                                                         10

SEQ ID NO: 45          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 45
LPPLERLTL                                                          9

SEQ ID NO: 46          moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 46
LCQAFSDVIL                                                         10

SEQ ID NO: 47          moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 47
RTFDMHSLES SLIDIMR                                                 17

SEQ ID NO: 48          moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 48
TNLEALQKKL EELELDE                                                 17

SEQ ID NO: 49          moltype = AA  length = 17
FEATURE                Location/Qualifiers
REGION                 1..17
                       note = Description of Artificial Sequence: Synthetic peptide
```

```
source                  1..17
                        mol_type = protein
                        organism = synthetic construct
SEQUENCE: 49
RSFEMTEFNQ ALEEIKG                                              17

SEQ ID NO: 50           moltype = AA  length = 321
FEATURE                 Location/Qualifiers
REGION                  1..321
                        note = Description of Artificial Sequence: Synthetic
                         polypeptide
source                  1..321
                        mol_type = protein
                        organism = synthetic construct
SEQUENCE: 50
MYGRKKRRQR RRGGMSDQEA KPSTEDLGDK KEGEYIKLKV IGQDSSEIHF KVKMTTHLKK  60
LKESYCQRQG VPMNSLRFLF EGQRIADNHT PKELGMEEED VIEVYQEQTG GMWTLGRRAV  120
AGLLASPSPA QAQTLTRVPR PAELAPLCGR RGLRTDIDAT CTPRRASSNQ RGLNQIWNVK  180
KQSVYLMNLR KSGTLGHPGS LDETTYERLA EETLDSLAEF FEDLADKPYT FEDYDVSFGS  240
GVLTVKLGGD LGTYVINKQT PNKQIWLSSP SSGPKRYDWT GKNWVYSHDG VSLHELLAAE  300
LTKALKTKLD LSSLAYSGKD A                                         321

SEQ ID NO: 51           moltype = AA  length = 321
FEATURE                 Location/Qualifiers
REGION                  1..321
                        note = Description of Artificial Sequence: Synthetic
                         polypeptide
source                  1..321
                        mol_type = protein
                        organism = synthetic construct
SEQUENCE: 51
MYGRKKRRQR RRGGSDSEVN QEAKPEVKPE VKPETHINLK VSDGSSEIFF KIKKTTPLRR  60
LMEAFAKRQG KEMDSLRFLY DGIRIQADQT PEDLDMEDND IIEAHREQIG GMWTLGRRAV  120
AGLLASPSPA QAQTLTRVPR PAELAPLCGR RGLRTDIDAT CTPRRASSNQ RGLNQIWNVK  180
KQSVYLMNLR KSGTLGHPGS LDETTYERLA EETLDSLAEF FEDLADKPYT FEDYDVSFGS  240
GVLTVKLGGD LGTYVINKQT PNKQIWLSSP SSGPKRYDWT GKNWVYSHDG VSLHELLAAE  300
LTKALKTKLD LSSLAYSGKD A                                         321

SEQ ID NO: 52           moltype = AA  length = 300
FEATURE                 Location/Qualifiers
REGION                  1..300
                        note = Description of Artificial Sequence: Synthetic
                         polypeptide
source                  1..300
                        mol_type = protein
                        organism = synthetic construct
SEQUENCE: 52
MYGRKKRRQR RRGGMQIFVK TLTGKTITLE VEPSDTIENV KAKIQDKEGI PPDQQRLIFA  60
GKQLEDGRTL SDYNIQKEST LHLVLRLRGG MWTLGRRAVA GLLASPSPAQ AQTLTRVPRP  120
AELAPLCGRR GLRTDIDATC TPRRASSNQR GLNQIWNVKK QSVYLMNLRK SGTLGHPGSL  180
DETTYERLAE ETLDSLAEFF EDLADKPYTF EDYDVSFGSG VLTVKLGGDL GTYVINKQTP  240
NKQIWLSSPS SGPKRYDWTG KNWVYSHDGV SLHELLAAEL TKALKTKLDL SSLAYSGKDA  300

SEQ ID NO: 53           moltype = AA  length = 228
FEATURE                 Location/Qualifiers
REGION                  1..228
                        note = Description of Artificial Sequence: Synthetic
                         polypeptide
source                  1..228
                        mol_type = protein
                        organism = synthetic construct
SEQUENCE: 53
MYGRKKRRQR RRGGDEVDMW TLGRRAVAGL LASPSPAQAQ TLTRVPRPAE LAPLCGRRGL  60
RTDIDATCTP RRASSNQRGL NQIWNVKKQS VYLMNLRKSG TLGHPGSLDE TTYERLAEET  120
LDSLAEFFED LADKPYTFED YDVSFGSGVL TVKLGGDLGT YVINKQTPNK QIWLSSPSSG  180
PKRYDWTGKN WVYSHDGVSL HELLAAELTK ALKTKLDLSS LAYSGKDA            228

SEQ ID NO: 54           moltype = AA  length = 232
FEATURE                 Location/Qualifiers
REGION                  1..232
                        note = Description of Artificial Sequence: Synthetic
                         polypeptide
source                  1..232
                        mol_type = protein
                        organism = synthetic construct
SEQUENCE: 54
MYGRKKRRQR RRGGEPLFAE RKMWTLGRRA VAGLLASPSP AQAQTLTRVP RPAELAPLCG  60
RRGLRTDIDA TCTPRRASSN QRGLNQIWNV KKQSVYLMNL RKSGTLGHPG SLDETTYERL  120
AEETLDSLAE FFEDLADKPY TFEDYDVSFG SGVLTVKLGG DLGTYVINKQ TPNKQIWLSS  180
```

-continued

```
PSSGPKRYDW TGKNWVYSHD GVSLHELLAA ELTKALKTKL DLSSLAYSGK DA         232

SEQ ID NO: 55          moltype = AA  length = 228
FEATURE                Location/Qualifiers
REGION                 1..228
                       note = Description of Artificial Sequence: Synthetic
                        polypeptide
source                 1..228
                       mol_type = protein
                       organism = synthetic construct
SEQUENCE: 55
MYGRKKRRQR RRGGLLVYMW TLGRRAVAGL LASPSPAQAQ TLTRVPRPAE LAPLCGRRGL  60
RTDIDATCTP RRASSNQRGL NQIWNVKKQS VYLMNLRKSG TLGHPGSLDE TTYERLAEET  120
LDSLAEFFED LADKPYTFED YDVSFGSGVL TVKLGGDLGT YVINKQTPNK QIWLSSPSSG  180
PKRYDWTGKN WVYSHDGVSL HELLAAELTK ALKTKLDLSS LAYSGKDA              228

SEQ ID NO: 56          moltype = AA  length = 234
FEATURE                Location/Qualifiers
REGION                 1..234
                       note = Description of Artificial Sequence: Synthetic
                        polypeptide
source                 1..234
                       mol_type = protein
                       organism = synthetic construct
SEQUENCE: 56
MYGRKKRRQR RRGGMWTLGR RAVAGLLASP SPAQAQTLTR VPRPAELAPL CGRRGLRTDI  60
DATCTPRRAS SNQRGLNQIW NVKKQSVYLM NLRKSGTLGH PGSLDETTYE RLAEETLDSL  120
AEFFEDLADK PYTFEDYDVS FGSGVLTVKL GGDLGTYVIN KQTPNKQIWL SSPSSGPKRY  180
DWTGKNWVYS HDGVSLHELL AAELTKALKT KLDLSSLAYS GKDALALKLA GLDL        234

SEQ ID NO: 57          moltype = AA  length = 234
FEATURE                Location/Qualifiers
REGION                 1..234
                       note = Description of Artificial Sequence: Synthetic
                        polypeptide
source                 1..234
                       mol_type = protein
                       organism = synthetic construct
SEQUENCE: 57
MYGRKKRRQR RRGGMWTLGR RAVAGLLASP SPAQAQTLTR VPRPAELAPL CGRRGLRTDI  60
DATCTPRRAS SNQRGLNQIW NVKKQSVYLM NLRKSGTLGH PGSLDETTYE RLAEETLDSL  120
AEFFEDLADK PYTFEDYDVS FGSGVLTVKL GGDLGTYVIN KQTPNKQIWL SSPSSGPKRY  180
DWTGKNWVYS HDGVSLHELL AAELTKALKT KLDLSSLAYS GKDALQKKLE ELEL        234
```